(12) United States Patent
Cunnac et al.

(10) Patent No.: US 9,689,012 B2
(45) Date of Patent: Jun. 27, 2017

(54) METHOD OF DUAL-ADAPTER RECOMBINATION FOR EFFICIENT CONCATENATION OF MULTIPLE DNA FRAGMENTS IN SHUFFLED OR SPECIFIED ARRANGEMENTS

(75) Inventors: Sébastien Cunnac, Montpellier (FR); Alan Collmer, Ithaca, NY (US)

(73) Assignee: Cornell University, Ithaca, NY (US)

( * ) Notice: Subject to any disclaimer, the term of this patent is extended or adjusted under 35 U.S.C. 154(b) by 109 days.

(21) Appl. No.: 13/879,290

(22) PCT Filed: Oct. 12, 2011

(86) PCT No.: PCT/US2011/055998
§ 371 (c)(1),
(2), (4) Date: Jul. 17, 2013

(87) PCT Pub. No.: WO2012/051327
PCT Pub. Date: Apr. 19, 2012

(65) Prior Publication Data
US 2013/0298265 A1     Nov. 7, 2013

Related U.S. Application Data

(60) Provisional application No. 61/392,209, filed on Oct. 12, 2010.

(51) Int. Cl.
 *C12N 15/10* (2006.01)
 *C12P 19/34* (2006.01)
 *C12N 15/66* (2006.01)

(52) U.S. Cl.
 CPC .............. *C12P 19/34* (2013.01); *C12N 15/10* (2013.01); *C12N 15/1027* (2013.01); *C12N 15/1034* (2013.01); *C12N 15/1041* (2013.01); *C12N 15/66* (2013.01)

(58) Field of Classification Search
 None
 See application file for complete search history.

(56) References Cited

U.S. PATENT DOCUMENTS

| | | | |
|---|---|---|---|
| 7,244,560 B2 * | 7/2007 | Chestnut et al. ............ 435/6.18 |
| 2005/0048514 A1 | 3/2005 | Bennett et al. |
| 2006/0141626 A1 | 6/2006 | Hauge et al. |
| 2007/0292954 A1 | 12/2007 | Elledge |
| 2008/0182296 A1 | 7/2008 | Chanda et al. |
| 2009/0011959 A1 | 1/2009 | Costa et al. |
| 2009/0075276 A1 | 3/2009 | Lee et al. |
| 2009/0275086 A1 | 11/2009 | Gibson et al. |
| 2010/0035768 A1 | 2/2010 | Gibson et al. |
| 2010/0184187 A1 | 7/2010 | Young et al. |

OTHER PUBLICATIONS

Hobert, Biotechniques, 2002, vol. 32, pp. 728-730.*
Cunnac et al. "Genetic Disassembly and Combinatorial Reassembly Identify a Minimal Functional Repertoire of Type III Effectors in Pseudomonas Syringae," PNAS 108(7):2975-2980 (2011) (with supporting information).
Engler et al. "Golden Gate Shuffling: A One-Pot DNA Shuffling Method Based on Type IIs Restriction Enzymes," PLOS One 4(5):1-9 (2009).
Raymond et al. "Linker-Mediated Recombinational Subcloning of Large DNA Fragments Using Yeast," Genome Research 12:190-197 (2002).
Sleight et al. "In-Fusion BioBrick Assembly and Re-engineering," Nucleic Acids Research 38(8):2624-2636 (2010).
Shao et al. "DNA Assembler, an In Vivo Genetic Method for Rapid Construction of Biochemical Pathways," Nucleic Acids Research 37(2):1-10 (2009).
International Search Report and Written Opinion for PCT/US2011/055998, filed Oct. 12, 2011.
Katzen F., "Gateway Recombinational Cloning: A Biological Operating System," Expert Opinion Drug Discovery 2 (4):571-589 (2007).
Alberts et al., "General Recombination," Molecular Biology of the Cell 4th Ed., New York: Garland Science (2002).

* cited by examiner

*Primary Examiner* — Mindy G Brown
(74) *Attorney, Agent, or Firm* — LeClairRyan, a Professional Corporation

(57) ABSTRACT

The present invention relates to methods of assembling a plurality of genetic units to form synthetic genetic constructs. This method involves appending universal adapter oligonucleotides and flexible adapter oligonucleotides to the 5' and 3' ends of separate genetic units to be assembled to form separate dual extended genetic units. The dual extended genetic units are assembled together via homologous recombination between the flexible adapter oligonucleotide portions of the dual extended units to form synthetic genetic constructs. The present invention further relates to synthetic genetic constructs formed using the methods of the present invention, and vectors, cells, and organisms containing such synthetic genetic constructs.

28 Claims, 37 Drawing Sheets

Figure 1:
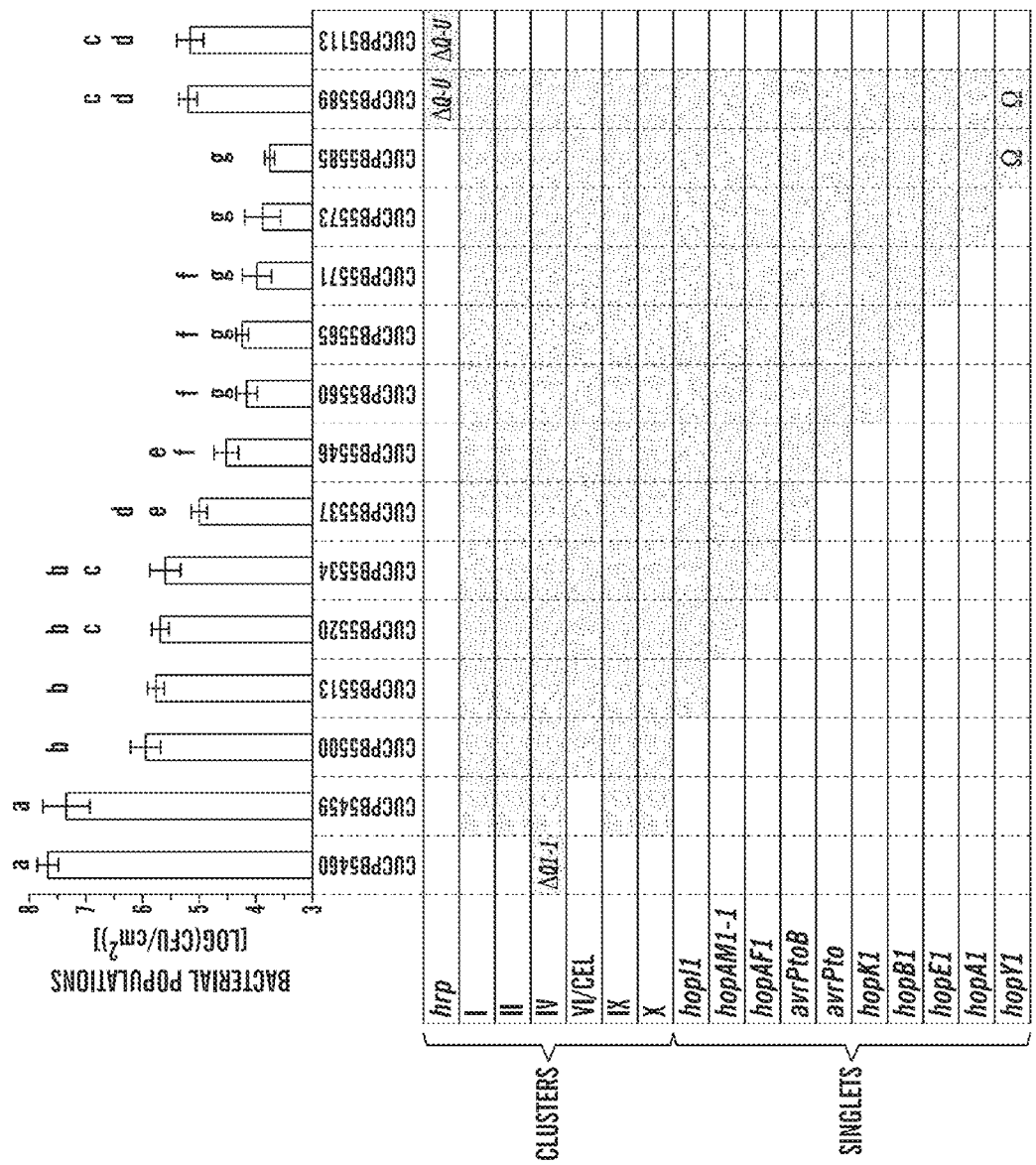

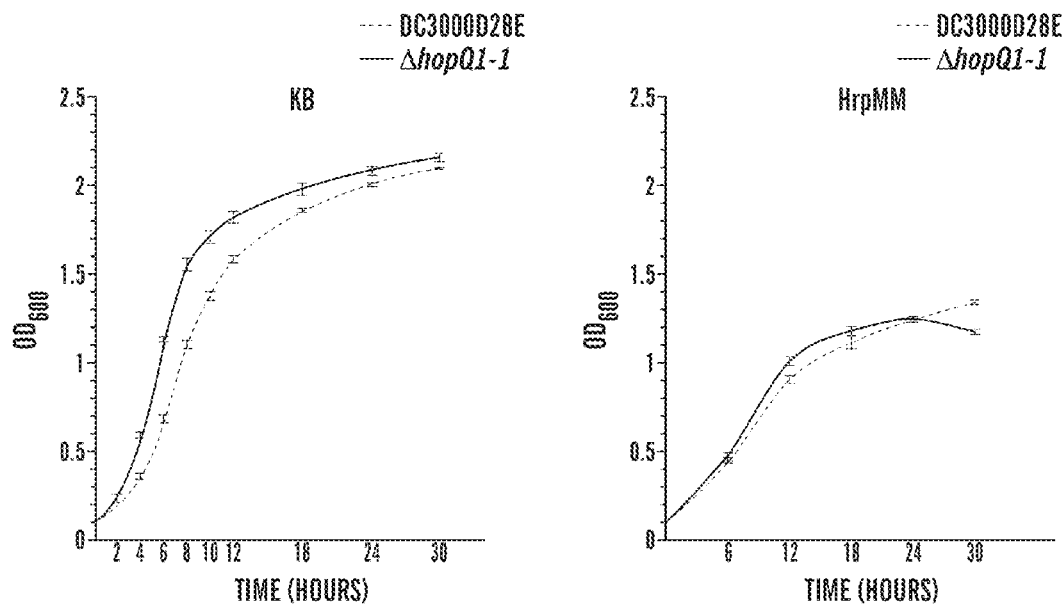
FIG. 4A
FIG. 4B
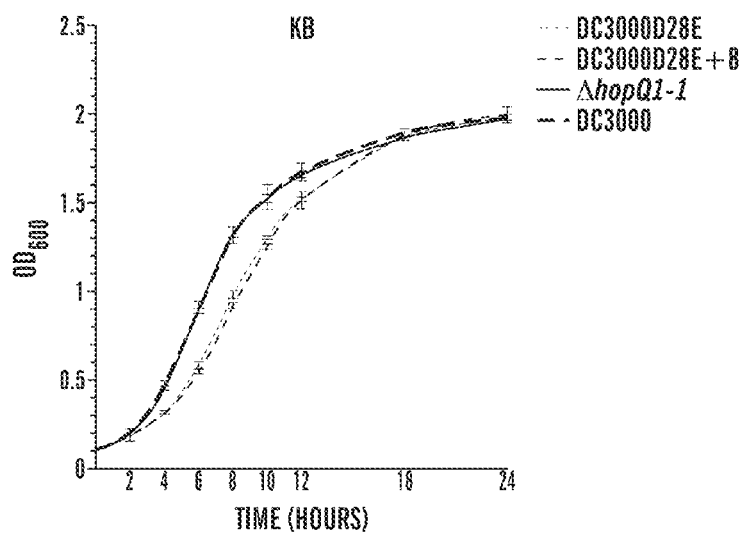
FIG. 4C

FIG. 8B

| STRAIN ID | SPECIFIED ASSEMBLY SIZE | hopAI | hopAF1 | hopAM1-1 | hopAO1 | hopC1 | hopE1 | hopF2 | hopG1 | hopH1 | hopI1 | hopK1 | hopO1-1 | hopX1 | hopY1 | avrPtoB | NOT AVAILABLE[1] | UNSPECIFIC[2] | POPULATION AT 6dpi IN LOG (cfu/cm$^2$) | STANDARD DEVIATION | EXPERIMENT ID |
|---|---|---|---|---|---|---|---|---|---|---|---|---|---|---|---|---|---|---|---|---|
| | | | | | | | | | | | | | | | | INTERMEDIATE GROWTH WITHOUT avrPtoB | | | | |
| ACED0141 | 5 | | | | | | | | | | | | | | | | ▓ | | 6.57 | 0.33 | D |
| ACED0129 | 5 | | | | | | | | | | | | | | | | ▓ | | 6.36 | 0.03 | D |
| ACED0136 | 5 | | | ▓ | | | | | | | | | | ▓ | | | | | 6.58 | 0.27 | C |
| ACED0016 | 5 | | | | | | | | | | | | | | | | | | 6.16 | 0.30 | A |
| ACED0014 | 5 | | | | | | | | | | | | | | | | | | 6.16 | 0.05 | A |
| ACED0142 | 5 | | | | | | | | | | | | | | | | | | 6.59 | 0.22 | D |
| ACED0137 | 5 | ▓ | ▓ | ▓ | | ▓ | | | | ▓ | | | ▓ | ▓ | | | | ▓ | 6.47 | 0.19 | C |
| ACED0160 | 3 | | | | | | | | | | | | | | | | | | 6.32 | 0.01 | C |

FIG. 8B (cont.)

FIG. 8B (cont.)

| STRAIN ID | SPECIFIED ASSEMBLY SIZE | hopAI | hopAF1 | hopAM1-1 | hopAO1 | hopC1 | hopE1 | hopF2 | hopG1 | hopH1 | hopI1 | hopK1 | hopQ1-1 | hopX1 | hopY1 | avrPtoB | NOT AVAILABLE? | UNSPECIFIC? | POPULATION AT 6dpi IN LOG (cfu/cm²) | STANDARD DEVIATION | EXPERIMENT ID |
|---|---|---|---|---|---|---|---|---|---|---|---|---|---|---|---|---|---|---|---|---|---|
| ACED0026 | 5 | | | | | | | | | | | | | | | | 2 | | 5.08 | 0.04 | A |
| ACED0149 | 3 | | | | | | | | | | | | | | | | | | 5.42 | 0.12 | C |
| ACED0158 | 3 | | | | | | | | | | | | | | | | | | 5.32 | 0.10 | C |
| ACED0013 | 5 | | | | | | | | | | | | | | | | | | 5.16 | 0.07 | A |
| ACED0024 | 5 | | | | | | | | | | | | | | b | | 2 | | 5.35 | 0.29 | B |
| ACED0181 | 3 | | | | | | | | | | | | | | | | | | 5.34 | 0.32 | C |
| ACED0115 | 5 | | | | | | | | | | | | | | | | | | 5.22 | 0.30 | D |
| ACED0130 | 5 | | | | | | | | | | | | | | | | | | 5.39 | 0.04 | D |
| ACED0143 | 5 | | | | | | | | | | | | | | | | | | 5.24 | 0.06 | D |
| ACED0170 | 3 | | | | | | | | | | | | | | | | | | 5.22 | 0.10 | C |
| ACED0066 | 3 | | | | | | | | | | | | | | | | | | 5.10 | 0.19 | A |
| ACED0086 | 3 | | | | | | | | | | | | | | | | | | 5.06 | 0.01 | A |
| ACED0167 | 3 | | | | | | | | | | | | | | | | | | 5.41 | 0.01 | D |
| ACED0172 | 3 | | | | | | | | | | | | | | | | 2 | | 5.39 | 0.21 | C |
| ACED0192 | 3 | | | | | | | | | | | | | | | | | | 5.38 | 0.13 | D |
| ACED0092 | 3 | | | | | | | | | | | | | | | | | | 5.28 | 0.45 | B |
| ACED0097 | 5 | | | | | | | | | | | | | | | | | | 5.26 | 0.24 | C |
| ACED0156 | 3 | | | | | | | | | | | | | | | | | | 5.19 | 0.32 | D |
| ACED0164 | 3 | | | | | | | | | | | | | | | | 4 | | 5.10 | 0.00 | B |
| ACED0037 | 5 | | | | | | | | | | | | | | | | | | 4.96 | 0.06 | A |
| ACED0085 | 3 | | | | | | | | | | | | | | c | | | | 4.89 | 0.03 | A |
| ACED0061 | 3 | | | | | | | | | | | | | | | | | 2 | 4.77 | 0.21 | A |
| COUNTS OF OCCURRENCES | | 18 | 20 | 7 | 2 | 10 | 20 | 19 | 7 | 17 | 4 | 13 | 6 | 14 | 9 | 26 | 13 | 14 | | | |

SEQUENCE LISTING

<160> NUMBER OF SEQ ID NOS: 165

<210> SEQ ID NO 1
<211> LENGTH: 35
<212> TYPE: DNA
<213> ORGANISM: Artificial
<220> FEATURE:
<223> OTHER INFORMATION: Oligonucleotide adapter sequence

```
<400> SEQUENCE: 1
tacgatgcca ggattgtgcg atcttcacgc tcagg                              35

<210> SEQ ID NO 2
<211> LENGTH: 35
<212> TYPE: DNA
<213> ORGANISM: Artificial
<220> FEATURE:
<223> OTHER INFORMATION: Oligonucleotide adapter sequence

<400> SEQUENCE: 2
tacgatgcca ggattgtgcg atcttcacgc tcagg                              35

<210> SEQ ID NO 3
<211> LENGTH: 35
<212> TYPE: DNA
<213> ORGANISM: Artificial
<220> FEATURE:
<223> OTHER INFORMATION: Oligonucleotide adapter sequence

<400> SEQUENCE: 3
cctgagcgtg aagatcgcac aatcctggca tcgta                              35

<210> SEQ ID NO 4
<211> LENGTH: 35
<212> TYPE: DNA
<213> ORGANISM: Artificial
<220> FEATURE:
<223> OTHER INFORMATION: Oligonucleotide adapter sequence

<400> SEQUENCE: 4
cctgagcgtg aagatcgcac aatcctggca tcgta                              35

<210> SEQ ID NO 5
<211> LENGTH: 35
<212> TYPE: DNA
<213> ORGANISM: Artificial
<220> FEATURE:
<223> OTHER INFORMATION: Oligonucleotide adapter sequence

<400> SEQUENCE: 5
acatctggct cacgatatgc caaactgcct cgcct                              35

<210> SEQ ID NO 6
<211> LENGTH: 35
<212> TYPE: DNA
<213> ORGANISM: Artificial
<220> FEATURE:
<223> OTHER INFORMATION: Oligonucleotide adapter sequence

<400> SEQUENCE: 6
acatctggct cacgatatgc caaactgcct cgcct                              35

<210> SEQ ID NO 7
<211> LENGTH: 35
<212> TYPE: DNA
<213> ORGANISM: Artificial
<220> FEATURE:
<223> OTHER INFORMATION: Oligonucleotide adapter sequence

<400> SEQUENCE: 7
aggcgaggca gtttggcata tcgtgagcca gatgt                              35
```

```
<210> SEQ ID NO 8
<211> LENGTH: 35
<212> TYPE: DNA
<213> ORGANISM: Artificial
<220> FEATURE:
<223> OTHER INFORMATION: Oligonucleotide adapter sequence

<400> SEQUENCE: 8
aggcgaggca gtttggcata tcgtgagcca gatgt                                35

<210> SEQ ID NO 9
<211> LENGTH: 36
<212> TYPE: DNA
<213> ORGANISM: Artificial
<220> FEATURE:
<223> OTHER INFORMATION: Oligonucleotide adapter sequence

<400> SEQUENCE: 9
tgggaagggc gatcggtgcg ggcctcttcg ctctcg                               36

<210> SEQ ID NO 10
<211> LENGTH: 36
<212> TYPE: DNA
<213> ORGANISM: Artificial
<220> FEATURE:
<223> OTHER INFORMATION: Oligonucleotide adapter sequence

<400> SEQUENCE: 10
tgggaagggc gatcggtgcg ggcctcttcg ctctcg                               36

<210> SEQ ID NO 11
<211> LENGTH: 35
<212> TYPE: DNA
<213> ORGANISM: Artificial
<220> FEATURE:
<223> OTHER INFORMATION: Oligonucleotide adapter sequence

<400> SEQUENCE: 11
acgtgtcatc ggttgcgtca tcggctggga gcatc                                35

<210> SEQ ID NO 12
<211> LENGTH: 35
<212> TYPE: DNA
<213> ORGANISM: Artificial
<220> FEATURE:
<223> OTHER INFORMATION: Oligonucleotide adapter sequence

<400> SEQUENCE: 12
acgtgtcatc ggttgcgtca tcggctggga gcatc                                35

<210> SEQ ID NO 13
<211> LENGTH: 36
<212> TYPE: DNA
<213> ORGANISM: Artificial
<220> FEATURE:
<223> OTHER INFORMATION: Oligonucleotide adapter sequence

<400> SEQUENCE: 13
gagtggacgt ttacaacatc gatcgcctcg aaccca                               36

<210> SEQ ID NO 14
<211> LENGTH: 36
<212> TYPE: DNA
<213> ORGANISM: Artificial
<220> FEATURE:
<223> OTHER INFORMATION: Oligonucleotide adapter sequence
```

<400> SEQUENCE: 14
gagtggacgt ttacaacatc gatcgcctcg aaccca                                     36

<210> SEQ ID NO 15
<211> LENGTH: 36
<212> TYPE: DNA
<213> ORGANISM: Artificial
<220> FEATURE:
<223> OTHER INFORMATION: Oligonucleotide adapter sequence

<400> SEQUENCE: 15
tgggttcgag gcgatcgatg ttgtaaacgt ccactc                                     36

<210> SEQ ID NO 16
<211> LENGTH: 36
<212> TYPE: DNA
<213> ORGANISM: Artificial
<220> FEATURE:
<223> OTHER INFORMATION: Oligonucleotide adapter sequence

<400> SEQUENCE: 16
tgggttcgag gcgatcgatg ttgtaaacgt ccactc                                     36

<210> SEQ ID NO 17
<211> LENGTH: 35
<212> TYPE: DNA
<213> ORGANISM: Artificial
<220> FEATURE:
<223> OTHER INFORMATION: Oligonucleotide adapter sequence

<400> SEQUENCE: 17
gcagtgttgg agttttgtac ctccagttgc ggcga                                      35

<210> SEQ ID NO 18
<211> LENGTH: 35
<212> TYPE: DNA
<213> ORGANISM: Artificial
<220> FEATURE:
<223> OTHER INFORMATION: Oligonucleotide adapter sequence

<400> SEQUENCE: 18
gcagtgttgg agttttgtac ctccagttgc ggcga                                      35

<210> SEQ ID NO 19
<211> LENGTH: 35
<212> TYPE: DNA
<213> ORGANISM: Artificial
<220> FEATURE:
<223> OTHER INFORMATION: Oligonucleotide adapter sequence

<400> SEQUENCE: 19
tcgccgcaac tggaggtaca aaactccaac actgc                                      35

<210> SEQ ID NO 20
<211> LENGTH: 35
<212> TYPE: DNA
<213> ORGANISM: Artificial
<220> FEATURE:
<223> OTHER INFORMATION: Oligonucleotide adapter sequence

<400> SEQUENCE: 20
tcgccgcaac tggaggtaca aaactccaac actgc                                      35

-continued

```
<210> SEQ ID NO 21
<211> LENGTH: 20
<212> TYPE: DNA
<213> ORGANISM: Artificial
<220> FEATURE:
<223> OTHER INFORMATION: Oligonucleotide adapter sequence

<400> SEQUENCE: 21
aacagggaga gggtggtggt                                              20

<210> SEQ ID NO 22
<211> LENGTH: 20
<212> TYPE: DNA
<213> ORGANISM: Artificial
<220> FEATURE:
<223> OTHER INFORMATION: Oligonucleotide adapter sequence

<400> SEQUENCE: 22
ggtggtagcg gtgcgtaagt                                              20

<210> SEQ ID NO 23
<211> LENGTH: 56
<212> TYPE: DNA
<213> ORGANISM: Artificial
<220> FEATURE:
<223> OTHER INFORMATION: Primer

<400> SEQUENCE: 23
ttaggtcttt ttttattgtg cgtaactaac ttgcccgagg ccctttcgtc ttcaag      56

<210> SEQ ID NO 24
<211> LENGTH: 58
<212> TYPE: DNA
<213> ORGANISM: Artificial
<220> FEATURE:
<223> OTHER INFORMATION: Primer

<400> SEQUENCE: 24
ctcggtaccc atcggcattt tcttttgcgt tttatttct gattatcaac cggggtgg    58

<210> SEQ ID NO 25
<211> LENGTH: 20
<212> TYPE: DNA
<213> ORGANISM: Artificial
<220> FEATURE:
<223> OTHER INFORMATION: Primer

<400> SEQUENCE: 25
ggaacaacag cacacacagg                                              20

<210> SEQ ID NO 26
<211> LENGTH: 20
<212> TYPE: DNA
<213> ORGANISM: Artificial
<220> FEATURE:
<223> OTHER INFORMATION: Primer

<400> SEQUENCE: 26
cagccaagag ggaaataagg                                              20

<210> SEQ ID NO 27
<211> LENGTH: 19
<212> TYPE: DNA
<213> ORGANISM: Artificial
<220> FEATURE:
<223> OTHER INFORMATION: Primer
```

```
<400> SEQUENCE: 27
gatactggct cggggtctg                                              19

<210> SEQ ID NO 28
<211> LENGTH: 17
<212> TYPE: DNA
<213> ORGANISM: Artificial
<220> FEATURE:
<223> OTHER INFORMATION: Primer

<400> SEQUENCE: 28
acggctctgg atggtcg                                                17

<210> SEQ ID NO 29
<211> LENGTH: 17
<212> TYPE: DNA
<213> ORGANISM: Artificial
<220> FEATURE:
<223> OTHER INFORMATION: Primer

<400> SEQUENCE: 29
ccgtttgtta ttgggcg                                                17

<210> SEQ ID NO 30
<211> LENGTH: 17
<212> TYPE: DNA
<213> ORGANISM: Artificial
<220> FEATURE:
<223> OTHER INFORMATION: Primer

<400> SEQUENCE: 30
agagcgattt gttgcga                                                17

<210> SEQ ID NO 31
<211> LENGTH: 20
<212> TYPE: DNA
<213> ORGANISM: Artificial
<220> FEATURE:
<223> OTHER INFORMATION: Primer

<400> SEQUENCE: 31
caggcgtatc aatcaaccag                                             20

<210> SEQ ID NO 32
<211> LENGTH: 20
<212> TYPE: DNA
<213> ORGANISM: Artificial
<220> FEATURE:
<223> OTHER INFORMATION: Primer

<400> SEQUENCE: 32
cgttatcttc gtcacccgag                                             20

<210> SEQ ID NO 33
<211> LENGTH: 62
<212> TYPE: DNA
<213> ORGANISM: Artificial
<220> FEATURE:
<223> OTHER INFORMATION: Primer

<400> SEQUENCE: 33
tgggaagggc gatcggtgcg ggcctcttcg ctctcgagac tagtaaagcc ttcgagcgtc    60
cc                                                                  62
```

```
<210> SEQ ID NO 34
<211> LENGTH: 43
<212> TYPE: DNA
<213> ORGANISM: Artificial
<220> FEATURE:
<223> OTHER INFORMATION: Primer

<400> SEQUENCE: 34
atgcattcgg atccatatgt gctaacaacc attttggaga ttc                    43

<210> SEQ ID NO 35
<211> LENGTH: 44
<212> TYPE: DNA
<213> ORGANISM: Artificial
<220> FEATURE:
<223> OTHER INFORMATION: Primer

<400> SEQUENCE: 35
atggttgtta gcacatatgg atccgaatgc attgccaact gatg                   44

<210> SEQ ID NO 36
<211> LENGTH: 55
<212> TYPE: DNA
<213> ORGANISM: Artificial
<220> FEATURE:
<223> OTHER INFORMATION: Primer

<400> SEQUENCE: 36
attaatgcag ctggcacgac aggtttcccg actacacagg atcgagcag aacgc        55

<210> SEQ ID NO 37
<211> LENGTH: 36
<212> TYPE: DNA
<213> ORGANISM: Artificial
<220> FEATURE:
<223> OTHER INFORMATION: Primer

<400> SEQUENCE: 37
gctctagagt tccttttttt atatgcccaa ccaacg                            36

<210> SEQ ID NO 38
<211> LENGTH: 34
<212> TYPE: DNA
<213> ORGANISM: Artificial
<220> FEATURE:
<223> OTHER INFORMATION: Primer

<400> SEQUENCE: 38
gctctagagt taaaacagca tgaagcatgc cgga                              34

<210> SEQ ID NO 39
<211> LENGTH: 18
<212> TYPE: DNA
<213> ORGANISM: Artificial
<220> FEATURE:
<223> OTHER INFORMATION: Primer

<400> SEQUENCE: 39
tgcggcagat caaaccctt                                               18

<210> SEQ ID NO 40
<211> LENGTH: 20
<212> TYPE: DNA
<213> ORGANISM: Artificial
<220> FEATURE:
<223> OTHER INFORMATION: Primer
```

```
<400> SEQUENCE: 40
cgaacaacac agaggcttgg                                                    20

<210> SEQ ID NO 41
<211> LENGTH: 20
<212> TYPE: DNA
<213> ORGANISM: Artificial
<220> FEATURE:
<223> OTHER INFORMATION: Primer

<400> SEQUENCE: 41
cgaacaacac agaggcttgg                                                    20

<210> SEQ ID NO 42
<211> LENGTH: 19
<212> TYPE: DNA
<213> ORGANISM: Artificial
<220> FEATURE:
<223> OTHER INFORMATION: Primer

<400> SEQUENCE: 42
ttcagcgatg gcaagataa                                                     19

<210> SEQ ID NO 43
<211> LENGTH: 24
<212> TYPE: DNA
<213> ORGANISM: Artificial
<220> FEATURE:
<223> OTHER INFORMATION: Primer

<400> SEQUENCE: 43
caccatgatg attcgtagcc taac                                               24

<210> SEQ ID NO 44
<211> LENGTH: 30
<212> TYPE: DNA
<213> ORGANISM: Artificial
<220> FEATURE:
<223> OTHER INFORMATION: Primer

<400> SEQUENCE: 44
agaaagctgg gtatcatcgc aagtgaaagt                                         30

<210> SEQ ID NO 45
<211> LENGTH: 23
<212> TYPE: DNA
<213> ORGANISM: Artificial
<220> FEATURE:
<223> OTHER INFORMATION: Primer

<400> SEQUENCE: 45
caccatgacc gcaccgatca aaa                                                23

<210> SEQ ID NO 46
<211> LENGTH: 30
<212> TYPE: DNA
<213> ORGANISM: Artificial
<220> FEATURE:
<223> OTHER INFORMATION: Primer

<400> SEQUENCE: 46
attaactagt gtgtaggctg gagctgcttc                                         30
```

```
<210> SEQ ID NO 47
<211> LENGTH: 29
<212> TYPE: DNA
<213> ORGANISM: Artificial
<220> FEATURE:
<223> OTHER INFORMATION: Primer

<400> SEQUENCE: 47
attaactagt catatgaata tcctcctta                                    29

<210> SEQ ID NO 48
<211> LENGTH: 30
<212> TYPE: DNA
<213> ORGANISM: Artificial
<220> FEATURE:
<223> OTHER INFORMATION: Primer

<400> SEQUENCE: 48
attacccggg gtgtaggctg gagctgcttc                                   30

<210> SEQ ID NO 49
<211> LENGTH: 29
<212> TYPE: DNA
<213> ORGANISM: Artificial
<220> FEATURE:
<223> OTHER INFORMATION: Primer

<400> SEQUENCE: 49
attacccggg catatgaata tcctcctta                                    29

<210> SEQ ID NO 50
<211> LENGTH: 32
<212> TYPE: DNA
<213> ORGANISM: Artificial
<220> FEATURE:
<223> OTHER INFORMATION: Primer

<400> SEQUENCE: 50
attaactagt aaaattacgg tgcaggagca gg                                32

<210> SEQ ID NO 51
<211> LENGTH: 30
<212> TYPE: DNA
<213> ORGANISM: Artificial
<220> FEATURE:
<223> OTHER INFORMATION: Primer

<400> SEQUENCE: 51
taattctaga tcaagccgaa gacgacagac                                   30

<210> SEQ ID NO 52
<211> LENGTH: 30
<212> TYPE: DNA
<213> ORGANISM: Artificial
<220> FEATURE:
<223> OTHER INFORMATION: Primer

<400> SEQUENCE: 52
cacctctaga tctattcccc gattgagcta                                   30

<210> SEQ ID NO 53
<211> LENGTH: 32
<212> TYPE: DNA
<213> ORGANISM: Artificial
<220> FEATURE:
<223> OTHER INFORMATION: Primer
```

```
<400> SEQUENCE: 53
taatactagt ggtacctggt cagattcagt gc                              32

<210> SEQ ID NO 54
<211> LENGTH: 20
<212> TYPE: DNA
<213> ORGANISM: Artificial
<220> FEATURE:
<223> OTHER INFORMATION: Primer

<400> SEQUENCE: 54
ctgcgaattc gagcccaacg                                            20

<210> SEQ ID NO 55
<211> LENGTH: 36
<212> TYPE: DNA
<213> ORGANISM: Artificial
<220> FEATURE:
<223> OTHER INFORMATION: Primer

<400> SEQUENCE: 55
taattctaga gctcatcagc ctgctcatca acgggg                          36

<210> SEQ ID NO 56
<211> LENGTH: 37
<212> TYPE: DNA
<213> ORGANISM: Artificial
<220> FEATURE:
<223> OTHER INFORMATION: Primer

<400> SEQUENCE: 56
taattctaga aaatgaaagc agcgttcggc gtaagtg                         37

<210> SEQ ID NO 57
<211> LENGTH: 22
<212> TYPE: DNA
<213> ORGANISM: Artificial
<220> FEATURE:
<223> OTHER INFORMATION: Primer

<400> SEQUENCE: 57
cggcgaattc gagttctggt tt                                         22

<210> SEQ ID NO 58
<211> LENGTH: 29
<212> TYPE: DNA
<213> ORGANISM: Artificial
<220> FEATURE:
<223> OTHER INFORMATION: Primer

<400> SEQUENCE: 58
atctctagag tgcgcggcca gagaatatc                                  29

<210> SEQ ID NO 59
<211> LENGTH: 31
<212> TYPE: DNA
<213> ORGANISM: Artificial
<220> FEATURE:
<223> OTHER INFORMATION: Primer

<400> SEQUENCE: 59
gcctcgaatt ctcacaccctt tccctataca c                              31
```

<210> SEQ ID NO 60
<211> LENGTH: 33
<212> TYPE: DNA
<213> ORGANISM: Artificial
<220> FEATURE:
<223> OTHER INFORMATION: Primer

<400> SEQUENCE: 60
atagaattcc cgcgctgaca gctaaaagcc cat                33

<210> SEQ ID NO 61
<211> LENGTH: 31
<212> TYPE: DNA
<213> ORGANISM: Artificial
<220> FEATURE:
<223> OTHER INFORMATION: Primer

<400> SEQUENCE: 61
taatatctag aggacaggcc ggactcgatc t                  31

<210> SEQ ID NO 62
<211> LENGTH: 28
<212> TYPE: DNA
<213> ORGANISM: Artificial
<220> FEATURE:
<223> OTHER INFORMATION: Primer

<400> SEQUENCE: 62
taatggatcc tctggatgct gggtatgt                      28

<210> SEQ ID NO 63
<211> LENGTH: 31
<212> TYPE: DNA
<213> ORGANISM: Artificial
<220> FEATURE:
<223> OTHER INFORMATION: Primer

<400> SEQUENCE: 63
taattctaga ccccatgacg gttctctctt t                  31

<210> SEQ ID NO 64
<211> LENGTH: 30
<212> TYPE: DNA
<213> ORGANISM: Artificial
<220> FEATURE:
<223> OTHER INFORMATION: Primer

<400> SEQUENCE: 64
taattctaga caataattca ataaagcgct                    30

<210> SEQ ID NO 65
<211> LENGTH: 27
<212> TYPE: DNA
<213> ORGANISM: Artificial
<220> FEATURE:
<223> OTHER INFORMATION: Primer

<400> SEQUENCE: 65
taatctgcag aaaactctac ctctacg                       27

<210> SEQ ID NO 66
<211> LENGTH: 24
<212> TYPE: DNA
<213> ORGANISM: Artificial
<220> FEATURE:
<223> OTHER INFORMATION: Primer

```
<400> SEQUENCE: 66
ctaaccagat ggctgtatgc atcc                                              24

<210> SEQ ID NO 67
<211> LENGTH: 22
<212> TYPE: DNA
<213> ORGANISM: Artificial
<220> FEATURE:
<223> OTHER INFORMATION: Primer

<400> SEQUENCE: 67
ctgggcttcg ataaagcgat tc                                                22

<210> SEQ ID NO 68
<211> LENGTH: 36
<212> TYPE: DNA
<213> ORGANISM: Artificial
<220> FEATURE:
<223> OTHER INFORMATION: Primer

<400> SEQUENCE: 68
taatgaattc cggaaattcg cacctgatcc agcagc                                 36

<210> SEQ ID NO 69
<211> LENGTH: 32
<212> TYPE: DNA
<213> ORGANISM: Artificial
<220> FEATURE:
<223> OTHER INFORMATION: Primer

<400> SEQUENCE: 69
taattctaga attcatgctg attgcacccc ta                                     32

<210> SEQ ID NO 70
<211> LENGTH: 34
<212> TYPE: DNA
<213> ORGANISM: Artificial
<220> FEATURE:
<223> OTHER INFORMATION: Primer

<400> SEQUENCE: 70
taattctaga gactgaatcc taggctctgt acga                                   34

<210> SEQ ID NO 71
<211> LENGTH: 36
<212> TYPE: DNA
<213> ORGANISM: Artificial
<220> FEATURE:
<223> OTHER INFORMATION: Primer

<400> SEQUENCE: 71
taatgcatgc tcgaccactt ctcggtcacg gtcatt                                 36

<210> SEQ ID NO 72
<211> LENGTH: 24
<212> TYPE: DNA
<213> ORGANISM: Artificial
<220> FEATURE:
<223> OTHER INFORMATION: Primer

<400> SEQUENCE: 72
gtgttctgcg tcatagcctt tgtc                                              24
```

```
<210> SEQ ID NO 73
<211> LENGTH: 22
<212> TYPE: DNA
<213> ORGANISM: Artificial
<220> FEATURE:
<223> OTHER INFORMATION: Primer

<400> SEQUENCE: 73
cgatccagtt ctccacaggc ac                                              22

<210> SEQ ID NO 74
<211> LENGTH: 31
<212> TYPE: DNA
<213> ORGANISM: Artificial
<220> FEATURE:
<223> OTHER INFORMATION: Primer

<400> SEQUENCE: 74
tcctagaatt ccttggtcga gaccgccaag g                                    31

<210> SEQ ID NO 75
<211> LENGTH: 28
<212> TYPE: DNA
<213> ORGANISM: Artificial
<220> FEATURE:
<223> OTHER INFORMATION: Primer

<400> SEQUENCE: 75
taatgaattc gcagcgtaga acgacaat                                        28

<210> SEQ ID NO 76
<211> LENGTH: 34
<212> TYPE: DNA
<213> ORGANISM: Artificial
<220> FEATURE:
<223> OTHER INFORMATION: Primer

<400> SEQUENCE: 76
taatactagt tcccattcgt atacctctt tagt                                  34

<210> SEQ ID NO 77
<211> LENGTH: 33
<212> TYPE: DNA
<213> ORGANISM: Artificial
<220> FEATURE:
<223> OTHER INFORMATION: Primer

<400> SEQUENCE: 77
taatactagt caatgatgtc aagccgtgtg tgg                                  33

<210> SEQ ID NO 78
<211> LENGTH: 20
<212> TYPE: DNA
<213> ORGANISM: Artificial
<220> FEATURE:
<223> OTHER INFORMATION: Primer

<400> SEQUENCE: 78
cagcgccacc tacgatgagt                                                 20

<210> SEQ ID NO 79
<211> LENGTH: 22
<212> TYPE: DNA
<213> ORGANISM: Artificial
<220> FEATURE:
<223> OTHER INFORMATION: Primer
```

<400> SEQUENCE: 79
aactcactga agcagcgcct tg                                    22

<210> SEQ ID NO 80
<211> LENGTH: 22
<212> TYPE: DNA
<213> ORGANISM: Artificial
<220> FEATURE:
<223> OTHER INFORMATION: Primer

<400> SEQUENCE: 80
caggactggg gctctggttt ca                                    22

<210> SEQ ID NO 81
<211> LENGTH: 36
<212> TYPE: DNA
<213> ORGANISM: Artificial
<220> FEATURE:
<223> OTHER INFORMATION: Primer

<400> SEQUENCE: 81
taatgctagc cgggcaacgc atgccttcaa tcagaa                     36

<210> SEQ ID NO 82
<211> LENGTH: 36
<212> TYPE: DNA
<213> ORGANISM: Artificial
<220> FEATURE:
<223> OTHER INFORMATION: Primer

<400> SEQUENCE: 82
taatcccggg atgaggctgg taatagggca tgagta                     36

<210> SEQ ID NO 83
<211> LENGTH: 22
<212> TYPE: DNA
<213> ORGANISM: Artificial
<220> FEATURE:
<223> OTHER INFORMATION: Primer

<400> SEQUENCE: 83
cttccccggg aactgatatc gc                                    22

<210> SEQ ID NO 84
<211> LENGTH: 22
<212> TYPE: DNA
<213> ORGANISM: Artificial
<220> FEATURE:
<223> OTHER INFORMATION: Primer

<400> SEQUENCE: 84
gcctgaattc acggcactga at                                    22

<210> SEQ ID NO 85
<211> LENGTH: 30
<212> TYPE: DNA
<213> ORGANISM: Artificial
<220> FEATURE:
<223> OTHER INFORMATION: Primer

<400> SEQUENCE: 85
taatgaattc tactggagag gttgccactt                            30

<210> SEQ ID NO 86
<211> LENGTH: 35
<212> TYPE: DNA
<213> ORGANISM: Artificial
<220> FEATURE:
<223> OTHER INFORMATION: Primer

<400> SEQUENCE: 86
taattctaga gactaaaaaa ctcaaatcag agtgc                                    35

<210> SEQ ID NO 87
<211> LENGTH: 32
<212> TYPE: DNA
<213> ORGANISM: Artificial
<220> FEATURE:
<223> OTHER INFORMATION: Primer

<400> SEQUENCE: 87
taattctaga gtgcatgtat gcctccagac gt                                       32

<210> SEQ ID NO 88
<211> LENGTH: 28
<212> TYPE: DNA
<213> ORGANISM: Artificial
<220> FEATURE:
<223> OTHER INFORMATION: Primer

<400> SEQUENCE: 88
cggaaagctt caagccttc tcttccag                                             28

<210> SEQ ID NO 89
<211> LENGTH: 22
<212> TYPE: DNA
<213> ORGANISM: Artificial
<220> FEATURE:
<223> OTHER INFORMATION: Primer

<400> SEQUENCE: 89
cccaccaagc tggctgcatc at                                                  22

<210> SEQ ID NO 90
<211> LENGTH: 22
<212> TYPE: DNA
<213> ORGANISM: Artificial
<220> FEATURE:
<223> OTHER INFORMATION: Primer

<400> SEQUENCE: 90
gtcaacggcc aggagcccta ta                                                  22

<210> SEQ ID NO 91
<211> LENGTH: 20
<212> TYPE: DNA
<213> ORGANISM: Artificial
<220> FEATURE:
<223> OTHER INFORMATION: Primer

<400> SEQUENCE: 91
ccgcaagcgt tcaagggtct                                                     20

<210> SEQ ID NO 92
<211> LENGTH: 22
<212> TYPE: DNA
<213> ORGANISM: Artificial
<220> FEATURE:
<223> OTHER INFORMATION: Primer

```
<400> SEQUENCE: 92
gcgctctgtc gcactaaagg ca                                              22

<210> SEQ ID NO 93
<211> LENGTH: 20
<212> TYPE: DNA
<213> ORGANISM: Artificial
<220> FEATURE:
<223> OTHER INFORMATION: Primer

<400> SEQUENCE: 93
atcctcgcgc ggcatttgag                                                 20

<210> SEQ ID NO 94
<211> LENGTH: 22
<212> TYPE: DNA
<213> ORGANISM: Artificial
<220> FEATURE:
<223> OTHER INFORMATION: Primer

<400> SEQUENCE: 94
gacggcccaa agagtcggtg aa                                              22

<210> SEQ ID NO 95
<211> LENGTH: 20
<212> TYPE: DNA
<213> ORGANISM: Artificial
<220> FEATURE:
<223> OTHER INFORMATION: Primer

<400> SEQUENCE: 95
agatcggccc gatgatgctc                                                 20

<210> SEQ ID NO 96
<211> LENGTH: 29
<212> TYPE: DNA
<213> ORGANISM: Artificial
<220> FEATURE:
<223> OTHER INFORMATION: Primer

<400> SEQUENCE: 96
taatggtacc ctgagtgcgg tgcggagca                                       29

<210> SEQ ID NO 97
<211> LENGTH: 20
<212> TYPE: DNA
<213> ORGANISM: Artificial
<220> FEATURE:
<223> OTHER INFORMATION: Primer

<400> SEQUENCE: 97
ccgtttgtta ttgggcgcaa                                                 20

<210> SEQ ID NO 98
<211> LENGTH: 20
<212> TYPE: DNA
<213> ORGANISM: Artificial
<220> FEATURE:
<223> OTHER INFORMATION: Primer

<400> SEQUENCE: 98
gcgtatcaat caaccagggc                                                 20
```

<210> SEQ ID NO 99
<211> LENGTH: 20
<212> TYPE: DNA
<213> ORGANISM: Artificial
<220> FEATURE:
<223> OTHER INFORMATION: Primer

<400> SEQUENCE: 99
gctcgaagtc agcgtcaatg                                          20

<210> SEQ ID NO 100
<211> LENGTH: 20
<212> TYPE: DNA
<213> ORGANISM: Artificial
<220> FEATURE:
<223> OTHER INFORMATION: Primer

<400> SEQUENCE: 100
cggtgaagtc atccagcact                                          20

<210> SEQ ID NO 101
<211> LENGTH: 22
<212> TYPE: DNA
<213> ORGANISM: Artificial
<220> FEATURE:
<223> OTHER INFORMATION: Primer

<400> SEQUENCE: 101
agcgctgcag actgatatgg ac                                       22

<210> SEQ ID NO 102
<211> LENGTH: 27
<212> TYPE: DNA
<213> ORGANISM: Artificial
<220> FEATURE:
<223> OTHER INFORMATION: Primer

<400> SEQUENCE: 102
taattctaga tctcatgatt gaatctc                                  27

<210> SEQ ID NO 103
<211> LENGTH: 26
<212> TYPE: DNA
<213> ORGANISM: Artificial
<220> FEATURE:
<223> OTHER INFORMATION: Primer

<400> SEQUENCE: 103
taattctaga gtctgagcgc ttgaac                                   26

<210> SEQ ID NO 104
<211> LENGTH: 26
<212> TYPE: DNA
<213> ORGANISM: Artificial
<220> FEATURE:
<223> OTHER INFORMATION: Primer

<400> SEQUENCE: 104
taatgaattc ggcgtacagc aggtcg                                   26

<210> SEQ ID NO 105
<211> LENGTH: 20
<212> TYPE: DNA
<213> ORGANISM: Artificial
<220> FEATURE:
<223> OTHER INFORMATION: Primer

<400> SEQUENCE: 105
aaaggcagtc gtcgagcaga                                              20

<210> SEQ ID NO 106
<211> LENGTH: 19
<212> TYPE: DNA
<213> ORGANISM: Artificial
<220> FEATURE:
<223> OTHER INFORMATION: Primer

<400> SEQUENCE: 106
catggcgtga tacaagcgg                                               19

<210> SEQ ID NO 107
<211> LENGTH: 39
<212> TYPE: DNA
<213> ORGANISM: Artificial
<220> FEATURE:
<223> OTHER INFORMATION: Primer

<400> SEQUENCE: 107
aacagggaga gggtggtggt cggacaggtc atcgtgcag                         39

<210> SEQ ID NO 108
<211> LENGTH: 41
<212> TYPE: DNA
<213> ORGANISM: Artificial
<220> FEATURE:
<223> OTHER INFORMATION: Primer

<400> SEQUENCE: 108
ggtggtagcg gtgcgtaagt cgagcggttc tgtttagcct t                      41

<210> SEQ ID NO 109
<211> LENGTH: 47
<212> TYPE: DNA
<213> ORGANISM: Artificial
<220> FEATURE:
<223> OTHER INFORMATION: Primer

<400> SEQUENCE: 109
aacagggaga gggtggtggt tgcagtatgt aggcttttg gagacga                 47

<210> SEQ ID NO 110
<211> LENGTH: 42
<212> TYPE: DNA
<213> ORGANISM: Artificial
<220> FEATURE:
<223> OTHER INFORMATION: Primer

<400> SEQUENCE: 110
ggtggtagcg gtgcgtaagt tcggggcgtt tgcttgggcc tt                     42

<210> SEQ ID NO 111
<211> LENGTH: 41
<212> TYPE: DNA
<213> ORGANISM: Artificial
<220> FEATURE:
<223> OTHER INFORMATION: Primer

<400> SEQUENCE: 111
aacagggaga gggtggtggt cgatggcggc gtttatgtgg a                      41

```
<210> SEQ ID NO 112
<211> LENGTH: 41
<212> TYPE: DNA
<213> ORGANISM: Artificial
<220> FEATURE:
<223> OTHER INFORMATION: Primer

<400> SEQUENCE: 112
ggtggtagcg gtgcgtaagt gcgggctatt gttgaaggtg a                41

<210> SEQ ID NO 113
<211> LENGTH: 42
<212> TYPE: DNA
<213> ORGANISM: Artificial
<220> FEATURE:
<223> OTHER INFORMATION: Primer

<400> SEQUENCE: 113
aacagggaga gggtggtggt gccttgtggc gggcttggtg gt               42

<210> SEQ ID NO 114
<211> LENGTH: 52
<212> TYPE: DNA
<213> ORGANISM: Artificial
<220> FEATURE:
<223> OTHER INFORMATION: Primer

<400> SEQUENCE: 114
ggtggtagcg gtgcgtaagt tcagaccctc cctatacatt tactttctat cc    52

<210> SEQ ID NO 115
<211> LENGTH: 43
<212> TYPE: DNA
<213> ORGANISM: Artificial
<220> FEATURE:
<223> OTHER INFORMATION: Primer

<400> SEQUENCE: 115
aacagggaga gggtggtggt gctttgccgt cttggcctac tga              43

<210> SEQ ID NO 116
<211> LENGTH: 44
<212> TYPE: DNA
<213> ORGANISM: Artificial
<220> FEATURE:
<223> OTHER INFORMATION: Primer

<400> SEQUENCE: 116
ggtggtagcg gtgcgtaagt tccgatctca ggcgatgcaa tcct             44

<210> SEQ ID NO 117
<211> LENGTH: 41
<212> TYPE: DNA
<213> ORGANISM: Artificial
<220> FEATURE:
<223> OTHER INFORMATION: Primer

<400> SEQUENCE: 117
aacagggaga gggtggtggt gcaacctgct ttcattccgc t                41

<210> SEQ ID NO 118
<211> LENGTH: 39
<212> TYPE: DNA
<213> ORGANISM: Artificial
<220> FEATURE:
<223> OTHER INFORMATION: Primer
```

<400> SEQUENCE: 118
ggtggtagcg gtgcgtaagt cgctcggtga tgctgcgtt                                39

<210> SEQ ID NO 119
<211> LENGTH: 43
<212> TYPE: DNA
<213> ORGANISM: Artificial
<220> FEATURE:
<223> OTHER INFORMATION: Primer

<400> SEQUENCE: 119
aacagggaga gggtggtggt gccccttcgt taccttccag cgt                           43

<210> SEQ ID NO 120
<211> LENGTH: 41
<212> TYPE: DNA
<213> ORGANISM: Artificial
<220> FEATURE:
<223> OTHER INFORMATION: Primer

<400> SEQUENCE: 120
ggtggtagcg gtgcgtaagt ggatgcgttt tggcggatga c                             41

<210> SEQ ID NO 121
<211> LENGTH: 40
<212> TYPE: DNA
<213> ORGANISM: Artificial
<220> FEATURE:
<223> OTHER INFORMATION: Primer

<400> SEQUENCE: 121
aacagggaga gggtggtggt accgtccaga gcgtcggcaa                               40

<210> SEQ ID NO 122
<211> LENGTH: 42
<212> TYPE: DNA
<213> ORGANISM: Artificial
<220> FEATURE:
<223> OTHER INFORMATION: Primer

<400> SEQUENCE: 122
ggtggtagcg gtgcgtaagt acgaggagcg gccaagcggg ta                            42

<210> SEQ ID NO 123
<211> LENGTH: 41
<212> TYPE: DNA
<213> ORGANISM: Artificial
<220> FEATURE:
<223> OTHER INFORMATION: Primer

<400> SEQUENCE: 123
aacagggaga gggtggtggt cctcgcgttt tgcgatagtg a                             41

<210> SEQ ID NO 124
<211> LENGTH: 42
<212> TYPE: DNA
<213> ORGANISM: Artificial
<220> FEATURE:
<223> OTHER INFORMATION: Primer

<400> SEQUENCE: 124
ggtggtagcg gtgcgtaagt cggcgtttgt cttaattcct tc                            42

<210> SEQ ID NO 125
<211> LENGTH: 44
<212> TYPE: DNA
<213> ORGANISM: Artificial
<220> FEATURE:
<223> OTHER INFORMATION: Primer

<400> SEQUENCE: 125
aacagggaga gggtggtggt aggctgaaga tttgtgacgc agag         44

<210> SEQ ID NO 126
<211> LENGTH: 43
<212> TYPE: DNA
<213> ORGANISM: Artificial
<220> FEATURE:
<223> OTHER INFORMATION: Primer

<400> SEQUENCE: 126
ggtggtagcg gtgcgtaagt acgcattttt ccgaggcagt gga          43

<210> SEQ ID NO 127
<211> LENGTH: 39
<212> TYPE: DNA
<213> ORGANISM: Artificial
<220> FEATURE:
<223> OTHER INFORMATION: Primer

<400> SEQUENCE: 127
aacagggaga gggtggtggt cgcataagtg gcaatcggt              39

<210> SEQ ID NO 128
<211> LENGTH: 40
<212> TYPE: DNA
<213> ORGANISM: Artificial
<220> FEATURE:
<223> OTHER INFORMATION: Primer

<400> SEQUENCE: 128
ggtggtagcg gtgcgtaagt tcaatcgtac ctgcctgtgg             40

<210> SEQ ID NO 129
<211> LENGTH: 49
<212> TYPE: DNA
<213> ORGANISM: Artificial
<220> FEATURE:
<223> OTHER INFORMATION: Primer

<400> SEQUENCE: 129
aacagggaga gggtggtggt agttcctttt tttatatgcc caaccaacg   49

<210> SEQ ID NO 130
<211> LENGTH: 44
<212> TYPE: DNA
<213> ORGANISM: Artificial
<220> FEATURE:
<223> OTHER INFORMATION: Primer

<400> SEQUENCE: 130
ggtggtagcg gtgcgtaagt taaaacagca tgaagcatgc cgga        44

<210> SEQ ID NO 131
<211> LENGTH: 41
<212> TYPE: DNA
<213> ORGANISM: Artificial
<220> FEATURE:
<223> OTHER INFORMATION: Primer

<400> SEQUENCE: 131
aacagggaga gggtggtggt ggaaggcgac aacatgcaga g          41

<210> SEQ ID NO 132
<211> LENGTH: 44
<212> TYPE: DNA
<213> ORGANISM: Artificial
<220> FEATURE:
<223> OTHER INFORMATION: Primer

<400> SEQUENCE: 132
ggtggtagcg gtgcgtaagt tgcggattga taggtatttt cact          44

<210> SEQ ID NO 133
<211> LENGTH: 41
<212> TYPE: DNA
<213> ORGANISM: Artificial
<220> FEATURE:
<223> OTHER INFORMATION: Primer

<400> SEQUENCE: 133
aacagggaga gggtggtggt ggggtcgcct cagaaaacgg a          41

<210> SEQ ID NO 134
<211> LENGTH: 40
<212> TYPE: DNA
<213> ORGANISM: Artificial
<220> FEATURE:
<223> OTHER INFORMATION: Primer

<400> SEQUENCE: 134
ggtggtagcg gtgcgtaagt agccaaggcc aagggcgtga          40

<210> SEQ ID NO 135
<211> LENGTH: 40
<212> TYPE: DNA
<213> ORGANISM: Artificial
<220> FEATURE:
<223> OTHER INFORMATION: Primer

<400> SEQUENCE: 135
aacagggaga gggtggtggt gccaatgcgt ttctcgatct          40

<210> SEQ ID NO 136
<211> LENGTH: 40
<212> TYPE: DNA
<213> ORGANISM: Artificial
<220> FEATURE:
<223> OTHER INFORMATION: Primer

<400> SEQUENCE: 136
ggtggtagcg gtgcgtaagt gcgctgctga tgggtatctt          40

<210> SEQ ID NO 137
<211> LENGTH: 41
<212> TYPE: DNA
<213> ORGANISM: Artificial
<220> FEATURE:
<223> OTHER INFORMATION: Primer

<400> SEQUENCE: 137
aacagggaga gggtggtggt ccgtattctt atggaagggc a          41

```
<210> SEQ ID NO 138
<211> LENGTH: 38
<212> TYPE: DNA
<213> ORGANISM: Artificial
<220> FEATURE:
<223> OTHER INFORMATION: Primer

<400> SEQUENCE: 138
ggtggtagcg gtgcgtaagt caggtgcgaa gtccgtga                                38

<210> SEQ ID NO 139
<211> LENGTH: 55
<212> TYPE: DNA
<213> ORGANISM: Artificial
<220> FEATURE:
<223> OTHER INFORMATION: Primer

<400> SEQUENCE: 139
tacgatgcca ggattgtgcg atcttcacgc tcaggaacag ggagagggtg gtggt             55

<210> SEQ ID NO 140
<211> LENGTH: 55
<212> TYPE: DNA
<213> ORGANISM: Artificial
<220> FEATURE:
<223> OTHER INFORMATION: Primer

<400> SEQUENCE: 140
tacgatgcca ggattgtgcg atcttcacgc tcaggggtgg tagcggtgcg taagt             55

<210> SEQ ID NO 141
<211> LENGTH: 55
<212> TYPE: DNA
<213> ORGANISM: Artificial
<220> FEATURE:
<223> OTHER INFORMATION: Primer

<400> SEQUENCE: 141
cctgagcgtg aagatcgcac aatcctggca tcgtaaacag ggagagggtg gtggt             55

<210> SEQ ID NO 142
<211> LENGTH: 55
<212> TYPE: DNA
<213> ORGANISM: Artificial
<220> FEATURE:
<223> OTHER INFORMATION: Primer

<400> SEQUENCE: 142
cctgagcgtg aagatcgcac aatcctggca tcgtaggtgg tagcggtgcg taagt             55

<210> SEQ ID NO 143
<211> LENGTH: 55
<212> TYPE: DNA
<213> ORGANISM: Artificial
<220> FEATURE:
<223> OTHER INFORMATION: Primer

<400> SEQUENCE: 143
acatctggct cacgatatgc caaactgcct cgcctaacag ggagagggtg gtggt             55

<210> SEQ ID NO 144
<211> LENGTH: 55
<212> TYPE: DNA
<213> ORGANISM: Artificial
<220> FEATURE:
<223> OTHER INFORMATION: Primer
```

<400> SEQUENCE: 144
acatctggct cacgatatgc caaactgcct cgcctggtgg tagcggtgcg taagt    55

<210> SEQ ID NO 145
<211> LENGTH: 55
<212> TYPE: DNA
<213> ORGANISM: Artificial
<220> FEATURE:
<223> OTHER INFORMATION: Primer

<400> SEQUENCE: 145
aggcgaggca gtttggcata tcgtgagcca gatgtaacag ggagagggtg gtggt    55

<210> SEQ ID NO 146
<211> LENGTH: 55
<212> TYPE: DNA
<213> ORGANISM: Artificial
<220> FEATURE:
<223> OTHER INFORMATION: Primer

<400> SEQUENCE: 146
aggcgaggca gtttggcata tcgtgagcca gatgtggtgg tagcggtgcg taagt    55

<210> SEQ ID NO 147
<211> LENGTH: 56
<212> TYPE: DNA
<213> ORGANISM: Artificial
<220> FEATURE:
<223> OTHER INFORMATION: Primer

<400> SEQUENCE: 147
tgggaagggc gatcggtgcg ggcctcttcg ctctcgaaca gggagagggt ggtggt    56

<210> SEQ ID NO 148
<211> LENGTH: 56
<212> TYPE: DNA
<213> ORGANISM: Artificial
<220> FEATURE:
<223> OTHER INFORMATION: Primer

<400> SEQUENCE: 148
tgggaagggc gatcggtgcg ggcctcttcg ctctcgggtg gtagcggtgc gtaagt    56

<210> SEQ ID NO 149
<211> LENGTH: 55
<212> TYPE: DNA
<213> ORGANISM: Artificial
<220> FEATURE:
<223> OTHER INFORMATION: Primer

<400> SEQUENCE: 149
acgtgtcatc ggttgcgtca tcggctggga gcatcaacag ggagagggtg gtggt    55

<210> SEQ ID NO 150
<211> LENGTH: 55
<212> TYPE: DNA
<213> ORGANISM: Artificial
<220> FEATURE:
<223> OTHER INFORMATION: Primer

<400> SEQUENCE: 150
acgtgtcatc ggttgcgtca tcggctggga gcatcggtgg tagcggtgcg taagt    55

<210> SEQ ID NO 151
<211> LENGTH: 56
<212> TYPE: DNA
<213> ORGANISM: Artificial
<220> FEATURE:
<223> OTHER INFORMATION: Primer

<400> SEQUENCE: 151
gagtggacgt ttacaacatc gatcgcctcg aacccaaaca gggagagggt ggtggt      56

<210> SEQ ID NO 152
<211> LENGTH: 56
<212> TYPE: DNA
<213> ORGANISM: Artificial
<220> FEATURE:
<223> OTHER INFORMATION: Primer

<400> SEQUENCE: 152
gagtggacgt ttacaacatc gatcgcctcg aacccaggtg gtagcggtgc gtaagt      56

<210> SEQ ID NO 153
<211> LENGTH: 56
<212> TYPE: DNA
<213> ORGANISM: Artificial
<220> FEATURE:
<223> OTHER INFORMATION: Primer

<400> SEQUENCE: 153
tgggttcgag gcgatcgatg ttgtaaacgt ccactcaaca gggagagggt ggtggt      56

<210> SEQ ID NO 154
<211> LENGTH: 56
<212> TYPE: DNA
<213> ORGANISM: Artificial
<220> FEATURE:
<223> OTHER INFORMATION: Primer

<400> SEQUENCE: 154
tgggttcgag gcgatcgatg ttgtaaacgt ccactcggtg gtagcggtgc gtaagt      56

<210> SEQ ID NO 155
<211> LENGTH: 55
<212> TYPE: DNA
<213> ORGANISM: Artificial
<220> FEATURE:
<223> OTHER INFORMATION: Primer

<400> SEQUENCE: 155
gcagtgttgg agttttgtac ctccagttgc ggcgaaacag ggagagggtg gtggt       55

<210> SEQ ID NO 156
<211> LENGTH: 55
<212> TYPE: DNA
<213> ORGANISM: Artificial
<220> FEATURE:
<223> OTHER INFORMATION: Primer

<400> SEQUENCE: 156
gcagtgttgg agttttgtac ctccagttgc ggcgaggtgg tagcggtgcg taagt       55

<210> SEQ ID NO 157
<211> LENGTH: 55
<212> TYPE: DNA
<213> ORGANISM: Artificial
<220> FEATURE:
<223> OTHER INFORMATION: Primer

<400> SEQUENCE: 157
tcgccgcaac tggaggtaca aaactccaac actgcaacag ggagagggtg gtggt    55

<210> SEQ ID NO 158
<211> LENGTH: 55
<212> TYPE: DNA
<213> ORGANISM: Artificial
<220> FEATURE:
<223> OTHER INFORMATION: Primer

<400> SEQUENCE: 158
tcgccgcaac tggaggtaca aaactccaac actgcggtgg tagcggtgcg taagt    55

<210> SEQ ID NO 159
<211> LENGTH: 23
<212> TYPE: DNA
<213> ORGANISM: Artificial
<220> FEATURE:
<223> OTHER INFORMATION: Primer

<400> SEQUENCE: 159
gctgctccat tccttcgaga tgc    23

<210> SEQ ID NO 160
<211> LENGTH: 27
<212> TYPE: DNA
<213> ORGANISM: Artificial
<220> FEATURE:
<223> OTHER INFORMATION: Primer

<400> SEQUENCE: 160
gctttctacg tgttccgctt cctttag    27

<210> SEQ ID NO 161
<211> LENGTH: 19
<212> TYPE: DNA
<213> ORGANISM: Artificial
<220> FEATURE:
<223> OTHER INFORMATION: Primer

<400> SEQUENCE: 161
acgtgtcatc ggttgcgtc    19

<210> SEQ ID NO 162
<211> LENGTH: 20
<212> TYPE: DNA
<213> ORGANISM: Artificial
<220> FEATURE:
<223> OTHER INFORMATION: Primer

<400> SEQUENCE: 162
tacgatgcca ggattgtgcg    20

<210> SEQ ID NO 163
<211> LENGTH: 20
<212> TYPE: DNA
<213> ORGANISM: Artificial
<220> FEATURE:
<223> OTHER INFORMATION: Primer

<400> SEQUENCE: 163
tcacgatatg ccaaactgcc    20

```
<210> SEQ ID NO 164
<211> LENGTH: 24
<212> TYPE: DNA
<213> ORGANISM: Artificial
<220> FEATURE:
<223> OTHER INFORMATION: Primer

<400> SEQUENCE: 164
gagtggacgt ttacaacatc gatc                                              24

<210> SEQ ID NO 165
<211> LENGTH: 23
<212> TYPE: DNA
<213> ORGANISM: Artificial
<220> FEATURE:
<223> OTHER INFORMATION: Primer

<400> SEQUENCE: 165
gcagtgttgg agttttgtac ctc                                               23
```

METHOD OF DUAL-ADAPTER RECOMBINATION FOR EFFICIENT CONCATENATION OF MULTIPLE DNA FRAGMENTS IN SHUFFLED OR SPECIFIED ARRANGEMENTS

This application is a national stage application under 35 U.S.C. 371 of PCT Application No. PCT/US2011/055998, filed Oct. 12, 2011, which claims the benefit of U.S. Provisional Patent Application Ser. No. 61/392,209, filed Oct. 12, 2010, which is hereby incorporated by reference in its entirety.

This application claims the benefit of U.S. Provisional Patent Application Ser. No. 61/392,209, filed Oct. 12, 2010, which is hereby incorporated by reference in its entirety.

FIELD OF THE INVENTION

The present invention relates to methods of assembling a plurality of genetic units (e.g., DNA fragments) to form synthetic genetic constructs. The present invention further relates to synthetic genetic constructs formed using the methods of the present invention, and vectors, cells, and organisms containing such synthetic genetic constructs.

BACKGROUND OF THE INVENTION

A general problem in molecular genetics and synthetic biology is the construction of concatenated sets of DNA fragments. The DNA fragments can represent genome segments, individual genes, domains within genes, etc. In some cases it is useful to shuffle the fragments (possibly from a large pool of input fragments) to generate random sets. In other cases it is useful to program the order in which DNA fragments are concatenated. In general, it is useful to have the ability to both shuffle and program the fragments and their arrangement as projects move from hypothesis generation to hypothesis testing phases. The DNA fragments assembled in such sets can be used in gain-of-function experiments to construct alternative metabolic pathways (Shao et al. 2008), multi-protein complexes, virulence systems that involve concerted attack on host defenses, or in loss-of-function experiments involving RNA interference where multiple genes redundantly contribute to a phenotype (Zhu et al., "A Versatile Approach to Multiple Gene RNA Interference Using MicroRNA-Based Short Hairpin RNAs," *BMC Mol. Biol.* 8:98 (2007)).

A general method for concatenating DNA fragments that lack sequence homology is to use various methods (primarily PCR) to attach short adapters to the ends of the DNA fragments to be concatenated (and typically inserted into a vector in the same process). These flanking "adapters" can recombine in yeast (Raymond et al., "General Method for Plasmid Construction Using Homologous Recombination," *Biotechniques* 26:134-8, 140-1 (1999)) or in bacterial strains expressing phage recombinases (Bieniossek et al. "Automated Unrestricted Multigene Recombineering for Multiprotein Complex Production," *Nat. Methods* 6:447-50 (2009)) that support recombination of such short (ca. 30 bp) adapters. This technology of adapter-driven recombination of DNA fragments in yeast is robust, and was used for example, to form a complete synthetic *Mycoplasma genitalium* genome (Gibson et al., "One-Step Assembly in Yeast of 25 Overlapping DNA Fragments to Form a Complete Synthetic *Mycoplasma Genitalium* Genome," *Proc. Nat'l. Acad. Sci. USA* 105:20404-9 (2008)). A disadvantage of this method is that DNA fragments can only assemble in the manner directed by attached adapters (i.e., programmed assembly) and alternative assemblies require the generation of DNA fragments with different adapter arrangements. In other words, each DNA fragment must be specialized to achieve a specific assembly. This approach becomes very laborious when trying to assemble several DNA fragments into several different genetic constructs.

In an extension of this approach, target DNA and vector fragments were electroporated into yeast along with 80-bp "linker" oligonucleotides carrying homology with the target fragment and the vector. Without further experimental manipulation, yeast recombined these into the desired construct (Raymond et al., "Linker-Mediated Recombinational Subcloning of Large DNA Fragments Using Yeast," *Genome Res.* 12:190-7 (2002)). Although this approach can be used to generate concatenated sets of DNA fragments in a designed arrangement, it is unlikely to work for shuffling fragments. Further, the DNA fragments can only assemble in the manner directed by the co-transfected linker oligonucleotides and alternative assemblies requires the generation and use of different linker oligonucleotides.

A particularly powerful, recent application of this general approach is the "Golden Gate Shuffling" method as described by Engler et al, "Golden Gate Shuffling: A One-Pot DNA Shuffling Method Based on Type IIs Restriction Enzymes" *PLoS One* 4:e5553 (2009), which involves constructing DNA fragments terminated with a unique sequence of four nucleotides followed by a BsaI cleavage site. Cleavage with BsaI exposes the four nucleotides as a single-stranded overhang that can hybridize with the overhang of another DNA fragment, as designed. A general limitation with golden gate shuffling (Engler et al., "Golden Gate Shuffling: a One-Pot DNA Shuffling Method Based on Type IIs Restriction Enzymes," *PLoS One* 4:e5553 (2009)), or in vitro sequence and ligation-independent cloning (SLIC) (Li and Elledge, "Harnessing Homologous Recombination in vitro to Generate Recombinant DNA Via SLIC," *Nat. Methods* 4:251-6 (2007)), or yeast-based recombination systems such as "DNAassembler" (Shao et al., "DNA Assembler, an in vivo Genetic Method for Rapid Construction of Biochemical Pathways," *Nucl. Acids Res.* (in press) (2008)), is that the generation of assemblies that are shuffled involves alternative arrangements of concatenated DNA fragments, which requires the generation and maintenance of multiple variants (differing in adapters) of each DNA fragment in the set.

The present invention is directed to overcoming these and other deficiencies in the art.

SUMMARY OF THE INVENTION

A first aspect of the present invention relates to a method of assembling synthetic genetic constructs comprising a plurality of genetic units. This method involves providing a plurality of separate genetic units, each having 5' and 3' ends, and appending universal adapter oligonucleotides to the 5' and 3' ends of each separate genetic unit to form separate extended genetic units each having 5' and 3' ends. This method further involves attaching a set of flexible adapter oligonucleotides to the 5' and 3' ends of separate extended genetic units to form separate dual extended genetic units, and assembling together the separate dual extended genetic units via homologous recombination between the flexible adapter oligonucleotides of the dual extended genetic units to form the synthetic genetic constructs.

Another aspect of the present invention relates to a synthetic genetic construct comprising a plurality of assembled separate genetic units. Each separate genetic unit comprises a gene specific portion, a pair of universal adapter oligonucleotides appended to the 5' and 3' ends of the gene specific portion, and a pair of flexible adapter oligonucleotides attached to the 5' and 3' ends of the universal adapter oligonucleotides appended to the gene specific portion. Other aspects of the present invention relate to vectors, host cells, and transgenic organisms comprising one or more synthetic genetic constructs of the present invention.

Another aspect of the present invention relates to a kit for assembling synthetic genetic constructs. This kit comprises one or more sets of universal adapter oligonucleotides, a collection of flexible adapter oligonucleotide sets, and reagents suitable for carrying out a homologous recombination reaction.

Described herein is a dual-adapter recombination (DAR) method for random, semi-random, or programmable assembly of genetic units that overcomes the above noted problems and limitations of current DNA assembly methods. This method exploits the ability of short, terminal adapters to direct recombination of unrelated DNA fragments in vivo or in vitro. The novel principle of the method is the use of a system of dual adapters enabling each unique DNA fragment in a set of interest to be flanked by a pair of hybrid universal-flexible adapters. Universal adapters (UAs) are first attached to the genetic units, such that all units in the set are flanked on one end by UA1 and the other by UA2. The flexible adapters (FAs) carry sequences complementary to a portion of the universal adapter sequences (such as UA1 or UA2), and they also carry unique sequences designed to support recombination among themselves and/or with vectors carrying recombination sites for FA1 and FAn (in a set involving FA1, FA2 ... FAn). Because the DNA fragments of interest have been universalized with UA1 and UA2 and the FAs from a separately maintained panel of oligonucleotides can be easily attached, a small number of starting reagents (the set of universalized DNA fragments and the set of FA oligonucleotides) can be used to generate infinitely complex random, semi-random, or programmed arrangements of concatenated products using any of a variety of in vitro or in vivo recombination methods. The method of the present invention is a universal technology infrastructure that is widely useful in the field of synthetic biology. The assembly of genetic fragments exists completely independent of the genetic information itself, allowing an infinite range of genetic units to be very easily assembled in any desired manner.

Figure 3A:
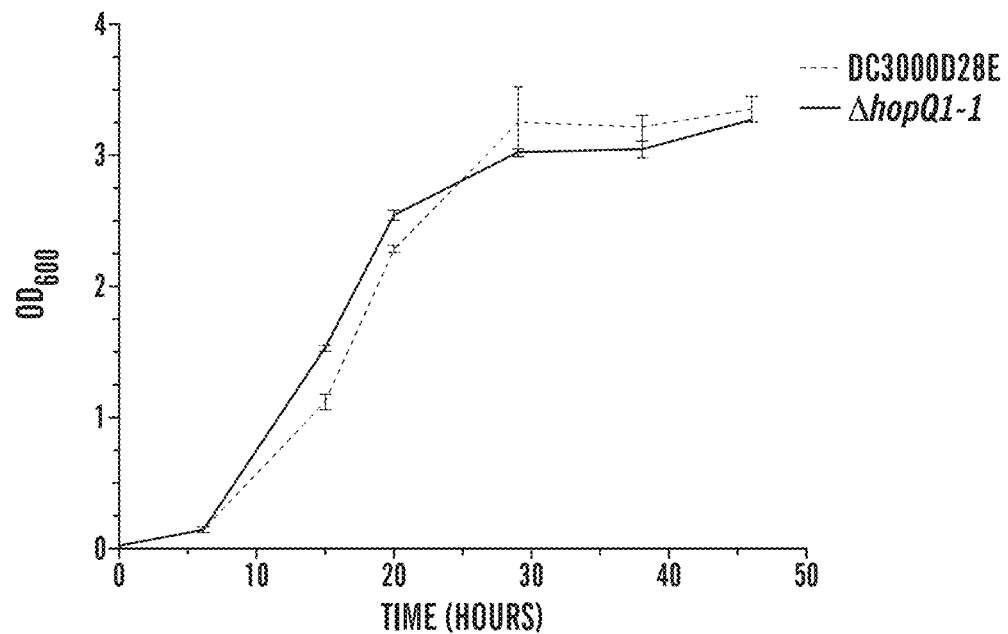
Figure 3B:
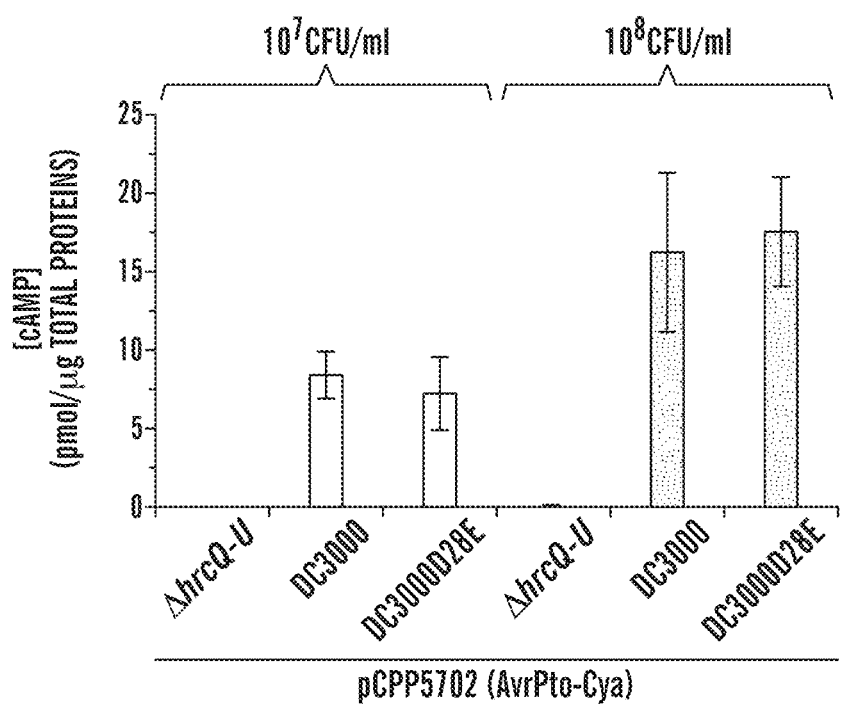
Figure 3C:
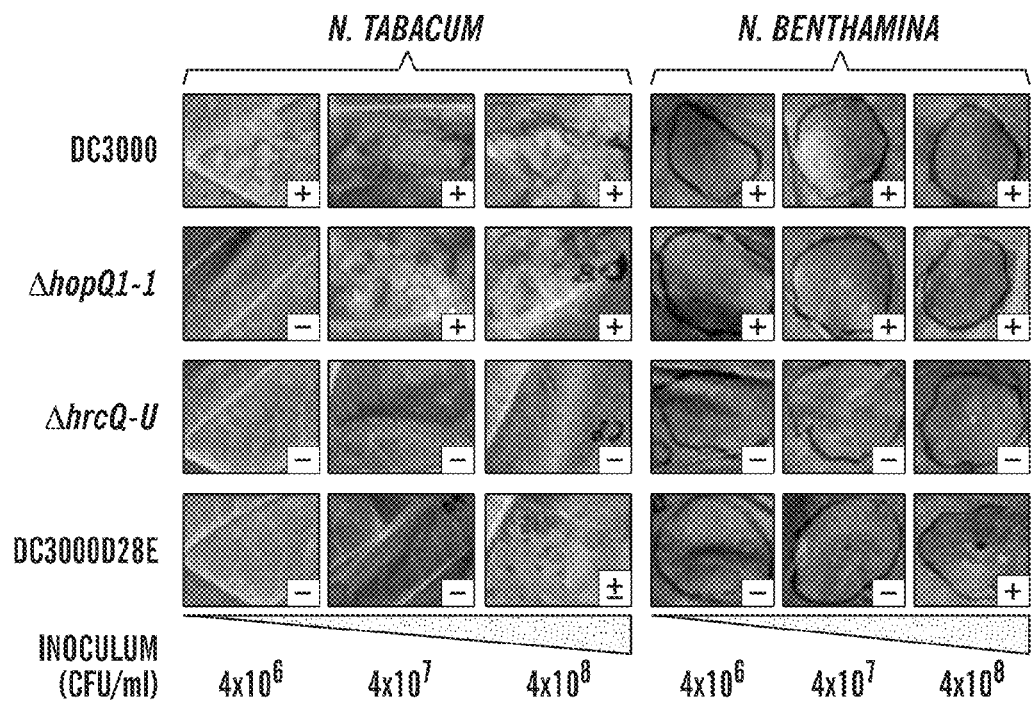
Figure 3D:
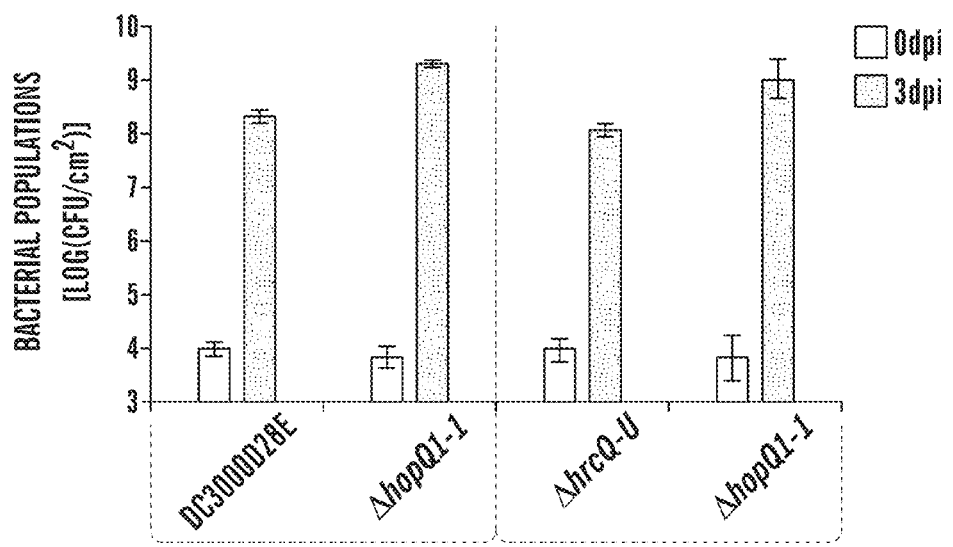

This dual adapter recombination method is used herein to support concatenation of T3E genes from *Pseudomonas syringe* via recombination in yeast. However, the DAR method of the invention has a wide variety of applications in the field of synthetic biology, permitting, for example, the design and easy generation of pathways for the synthesis of useful products, including, but not limited to, pharmaceuticals, biofuels, diagnostics, veterinary products, agricultural chemicals, growth factors, and the like, i.e., any molecule from a pathway or process that can be assembled in a cell culture or in a transgenic animal or plant. Thus the synthetic genetic constructs that result from the DAR method of the present invention may be employed in a wide variety of contexts to produce useful products.

BRIEF DESCRIPTION OF THE DRAWINGS

FIG. 1 shows that the deletion of 10 T3E genes in CUCPB5500, yielding DC3000D28E (CUCPB5585), strongly reduces *P. syringae* pv. *tomato* growth in *N. benthamiana*. Bacteria were inoculated with a blunt syringe at $3\times10^4$ CFU/ml in $MgCl_2$ buffer, and populations in three 0.8-cm leaf disks were determined at 6 dpi. The arithmetic mean of log transformed values of four replicate infiltrations from independent plants is displayed±SD. Strains with the same letter are not statistically different based on a Tukey's DSD (Honestly Significant Difference) test (α=0.05). The cells in the genotype grid are shadowed in dark grey if the corresponding strains carry a deletion of the matching genomic region, or left white if the locus is wild type. The "Ω" for hopY1 indicates that the gene was interrupted by insertion of a spectinomycin resistance cassette flanked by FRT sites. This experiment was repeated three times with similar results.

FIG. 2 shows an overview of the *P. syringae* pv. *tomato* DC3000 type III effector (T3E) gene repertoire and key steps and strains used in the disassembly of the repertoire and reassembly of a minimal functional repertoire for virulence in the model plant *N. benthamiana*. Wild-type DC3000 does not grow well or cause disease in *N. benthamiana*. Step 1: Deletion of the hopQ1-1 a virulence determinant enables DC3000 to become virulent on *N. benthamiana*, and all subsequent experiments employ strains lacking this gene (Wei et al. "A *Pseudomonas syringae* pv. *tomato* DC3000 Mutant Lacking the Type III Effector HopQ1-1 is Able to Cause Disease in the Model Plant *Nicotiana benthamiana*," *Plant J.* 51:32-46 (2007), which is hereby incorporated by reference in its entirety). Step 2: Redundant effector groups (REGs) are revealed by the strong reductions in growth observed with deletion of certain combinations of T3E genes, such as avrPto/avrPtoB or avrE/hopM1/hopR1, which contrasts with the weaker (if any) reductions attending mutation of any single effector gene or the deletion of many genes in other combinations (CUCPB5459) (Kvitko et al. "Deletions in the Repertoire of *Pseudomonas syringae* pv. *tomato* DC3000 type III Secretion Effector Genes Reveal Functional Overlap Among Effectors," *PLoS Pathogens* 5:e1000388 (2009), which is hereby incorporated by reference in its entirety). Step 3: Deletion of all clusters of well-expressed T3E genes strongly reduces, but does not abolish, growth relative to the $T3SS^-$ mutant (Kvitko et al. "Deletions in the Repertoire of *Pseudomonas syringae* pv. *tomato* DC3000 type III Secretion Effector Genes Reveal Functional Overlap Among Effectors," *PLoS Pathogens* 5:e1000388 (2009), which is hereby incorporated by reference in its entirety). Step 4: Deletion/disruption of the remaining well-expressed T3E genes produces DC3000D28E, which is functionally effectorless but otherwise wild type and grows worse than T3SS" derivatives of either DC3000 or DC3000D28E (FIGS. 1 and 3). Step 5: Integration into native loci of genes encoding the AvrPto and AvrE REGs reveals AvrPto and AvrPtoB function as early-acting effectors and potentiate the virulence contributions of AvrE REG effectors such as HopM1 (CUCPB6016) (FIG. 5). Step 6: Using the programmable or random in vivo assembly shuttle system (PRIVAS) in the random mode (FIG. 6), 18 T3E genes expressed from native promoters are assembled in groups of 3 or 5 in the exchangeable effector locus (EEL) of CUCPB6016, and multiple combinations are observed to stimulate growth in planta (FIG. 7). Step 7: PRIVAS operating in the programmed mode is used to assemble a minimal functional repertoire of T3E genes that enable near-wild-type growth and symptom production in *N. benthamiana* (CUCPB6032) (FIG. 9).

FIGS. 3A-3D demonstrate that DC3000D28E (CUCPB5585) is functionally effectorless but otherwise wild type in diagnostic assays. FIG. 3A is a growth curve showing equivalent growth of DC3000D28E and DC3000ΔhopQ1-1 in liquid mannitol glutamate minimal media supplemented with 50 μM iron citrate (means±SD of the absorbance of triplicate cultures). FIG. 3B shows equivalent translocation of an AvrPto-Cya fusion by DC3000D28E and DC3000. Plasmid pCPP5702 encoding the reporter gene under transcriptional control of the avrPto promoter was introduced into DC3000D28E, DC3000, and the ΔhrcQ-U T3SS⁻ mutant. The resulting strains were infiltrated into N. benthamiana leaves at two different densities ($10^7$ and $10^8$ CFU/ml) to control for assay saturation. cAMP concentrations were determined from tissues sampled from three independent leaves/treatment 7 h post-inoculation. Means±SD from one of two replicate experiments are shown. FIG. 3C depicts the reduced ability of DC3000D28E to elicit ETI-like rapid plant cell death in N. benthamiana and N. tabacum. DC3000D28E and controls DC3000 (incompatible on both Nicotiana spp.), ΔhopQ1-1 (incompatible on N. tabacum) and ΔhrcQ-U cell suspensions in $MgCl_2$ buffer, adjusted to three densities covering the dynamic range of the assay, were infiltrated into leaves and the plant response was photographed 48 h later. Cell death response: +, positive; −null; ±, partial. Each experiment was repeated at least three times with similar results. The ability of DC3000D28E to be trans complemented in mixed infections with virulent DC3000ΔhopQ1-1 is shown in the graphs of FIG. 3D. Equal volumes of DC3000D28E and ΔhopQ1-1 strains (left side) or ΔhrcQ-U and ΔhopQ1-1 strains (right side) standardized at $3\times10^6$ CFU/ml (an inoculum level high enough for DC3000ΔhopQ1-1 to produce conditions favoring bacterial growth throughout the inoculated tissue) were mixed and infiltrated into leaves of N. benthamiana. Values (means±SD of three samples) for the query strains and DC3000ΔhopQ1-1 were calculated by subtracting CFU counts on nonselective media (all strains) by CFUs on selective media (spectinomycin-resistant query strains). The experiment was repeated three times with similar results.

Figure 5:
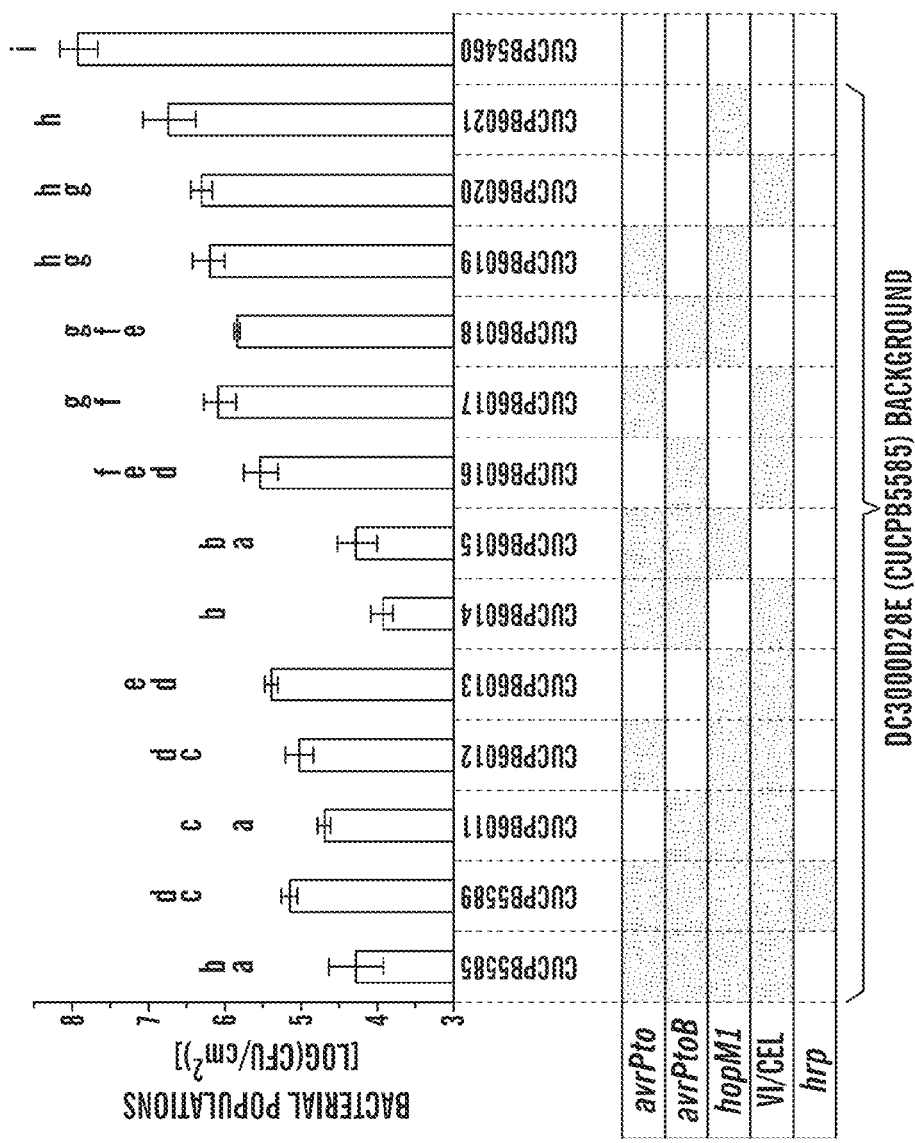

FIGS. 4A-4C show the growth of DC3000D28E and DC3000ΔhopQ1-1 in rich King's B medium (KB) (King et al., "Two Simple Media for the Demonstration of Pyocyanin and Fluorescin" J. Lab. Clin. Med. 44:301-307 (1954), which is hereby incorporated by reference in its entirety) and Hrp minimal medium (HrpMM) (Huynh et al., "Bacterial Blight of Soybean: Regulation of a Pathogen Gene Determining Host Cultivar Specificity," Science 245:1374-1377 (1989), which is hereby incorporated by reference in its entirety). Fresh plates were used to start seed cultures in liquid KB and then grown to log phase ($OD_{600}$≤1.0). The seed cultures were used to initiate 60 ml cultures in KB (FIG. 4A) or HrpMM (FIG. 4B) at a starting $OD_{600}$ of 0.1. The average $OD_{600}$±SD of triplicate cultures is shown. Growth of DC3000D28E and CUCPB6032 (DC3000D28E+8 effector genes) was also compared to DC3000 and DC3000ΔhopQ1-1 in KB (FIG. 4C). Cultures were prepared and analyzed in the same manner as described above. The experiment was repeated three times with similar results FIG. 5 shows that restoration of genes encoding the AvrPto and AvrE REGs to native loci in DC3000D28E suggests that AvrPto and AvrPtoB interfere at an early phase of the host immune response. White fill in the genotype grid indicates that the locus was restored (note, the CEL includes hopM1). Strains harboring combinations of multiple wild-type loci were constructed by sequential integrations. Growth assays were performed at 6 dpi as in FIG. 1 with means±SD of the bacterial populations calculated using values from three replicate leaves per strain. Means with the same letters are not statistically different based on a Tukey's HSD test (α=0.05). This experiment was repeated three times with similar results.

Figure 6A:
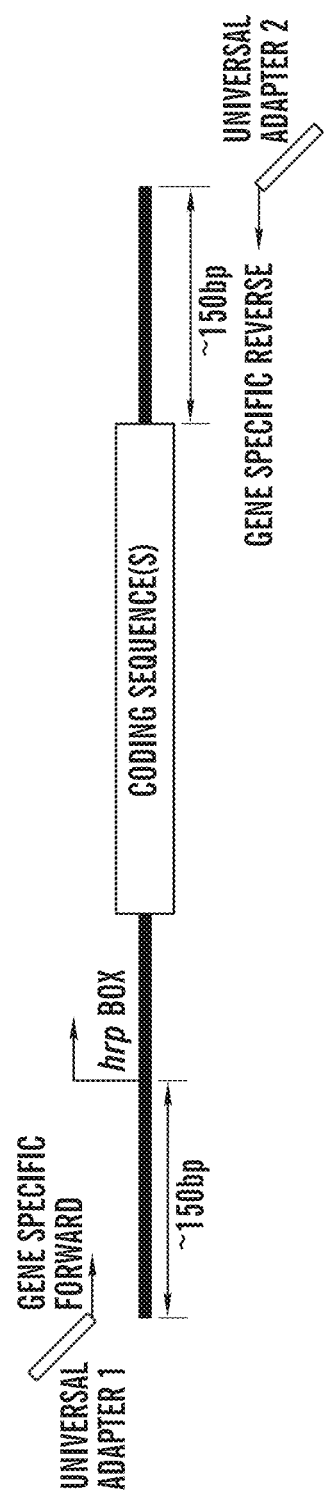
Figure 6B:
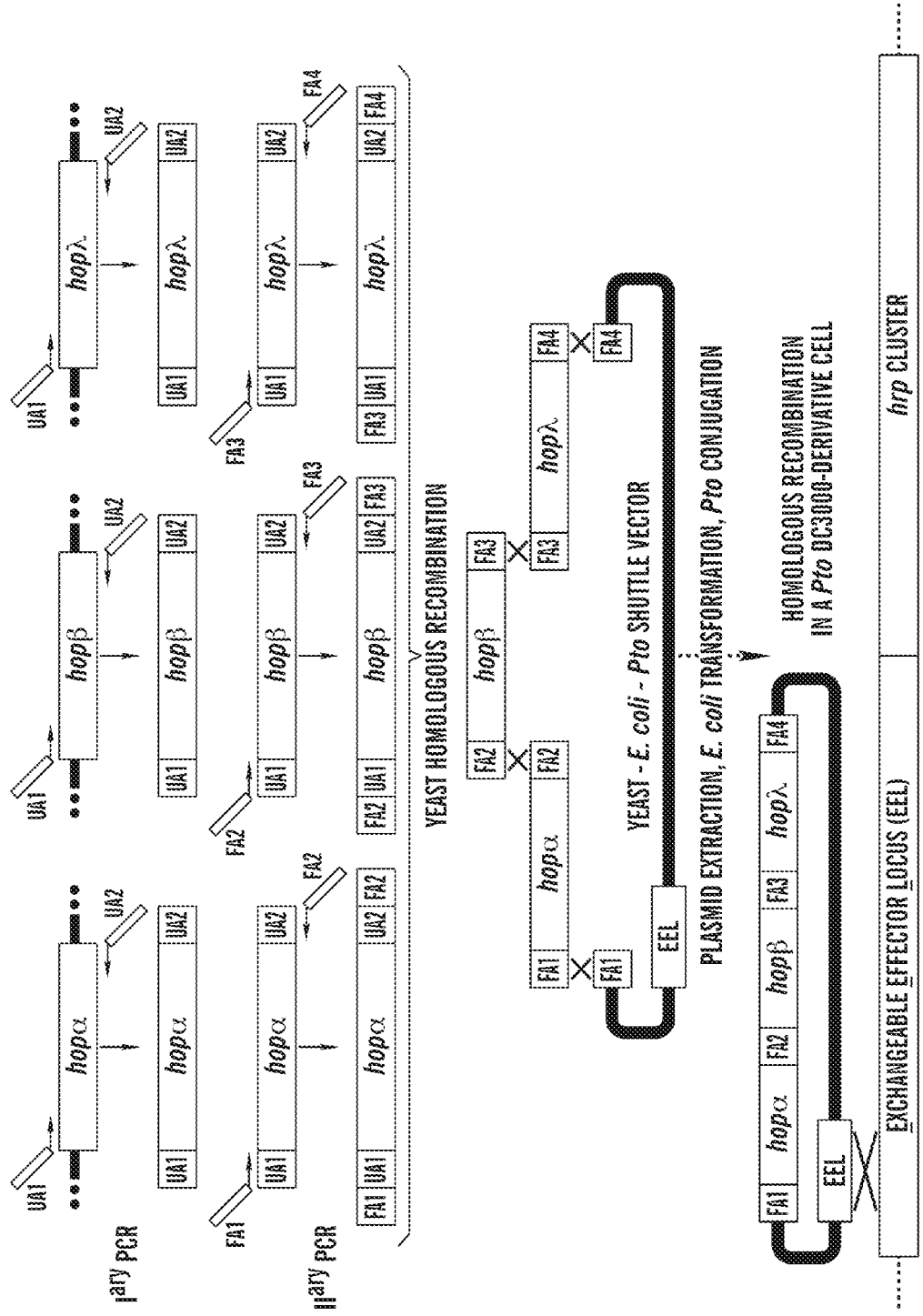
Figure 6C:
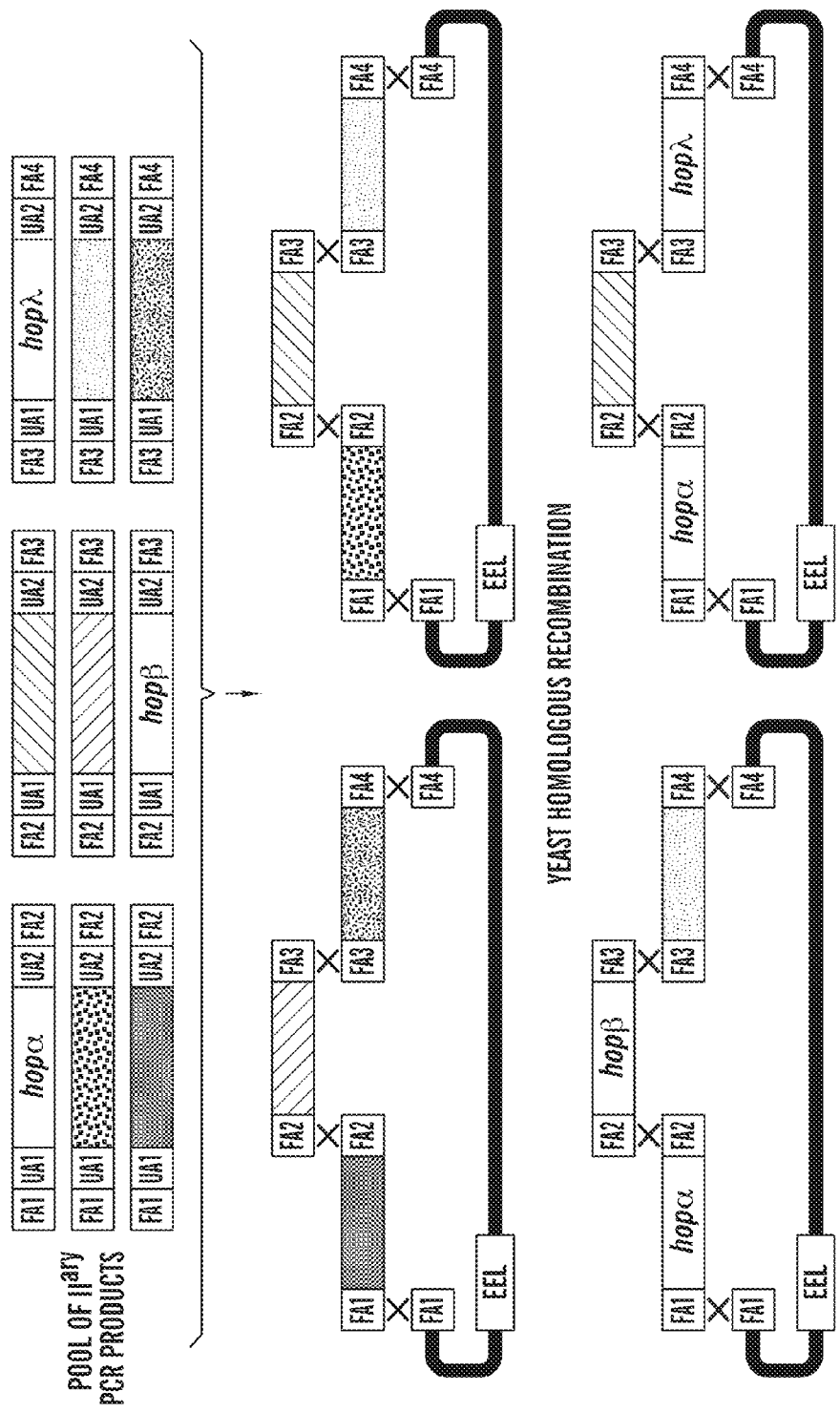

FIGS. 6A-6C depict the programmable or random in vivo assembly shuttle (PRIVAS) system that exploits dual adapter recombination for facile integration of combinatorial gene sets into the DC3000 exchangeable effector locus (EEL). FIG. 6A shows the structure of a typical T3E genetic unit (GU) for PRIVAS. Primary PCR reactions with gene-specific oligonucleotide primers harboring 20-bp 3' extensions amplify GUs flanked on each side by universal adapter (UA) regions 1 or 2. As shown in FIG. 6B, secondary PCR reactions use these primary products as templates and flexible adapter (FA) primers composed of UA-specific segments at their 3'-end and one of a set of ~35-bp FA-homology regions in their 5'-end to yield UA-FA dual adapter-flanked GUs that are used as the elementary building blocks for in vivo assembly in yeast. The configuration of the gene sets, including gene orientation, can be fully programmed during construction by designing FA-flanked GUs so that a unique combination of recombination events between FAs leads to the closure of a circular DNA molecule containing the sequences of the shuttle vector as depicted in FIG. 6B for 3 GUs. The shuttle vector's backbone provides the origins of replication and selection markers for yeast and E. coli well as an origin of transfer for conjugation into P. syringae. Following transformation with a suitable pool of GUs and the linearized shuttle vector, plasmid DNA is extracted from yeast cells surviving selection and transferred into E. coli for subsequent conjugation into a recipient P. syringae strain and single crossover integration into the EEL. PRIVAS also can be used in random mode, as shown in FIG. 6C, for the creation of complex combinatorial libraries of gene sets of variable configuration but of fixed size (equal to 3 in FIG. 6C). If several distinct GUs sharing the same pair of external FAs specifying a given position within the gene sets are included in the assembly reaction, identical FAs compete for recombination and hence incorporation in growing DNA molecules. The final circular products contain polymorphic sets composed of GUs drawn from distinct bins of GUs at desired positions as illustrated in FIG. 6C.

Figure 7A:
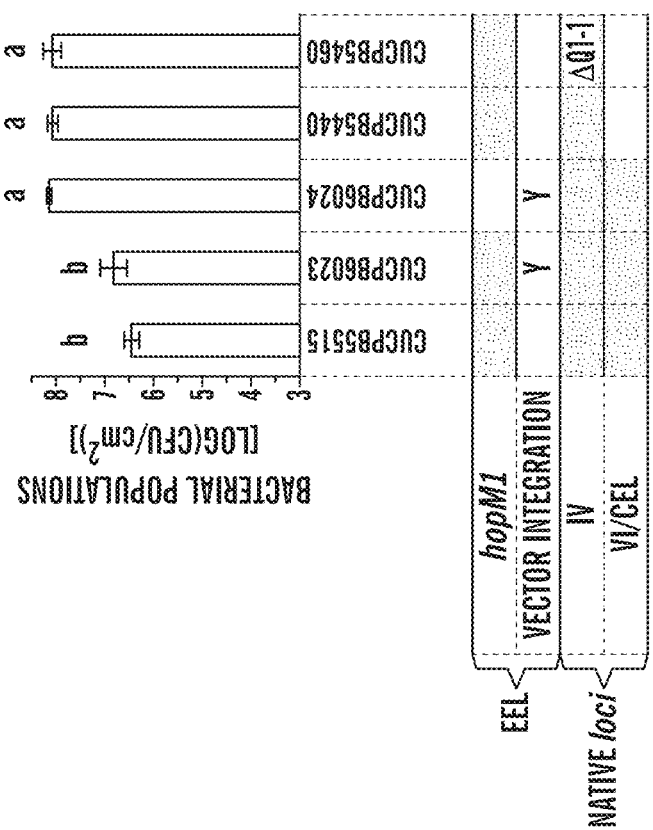
Figure 7B:
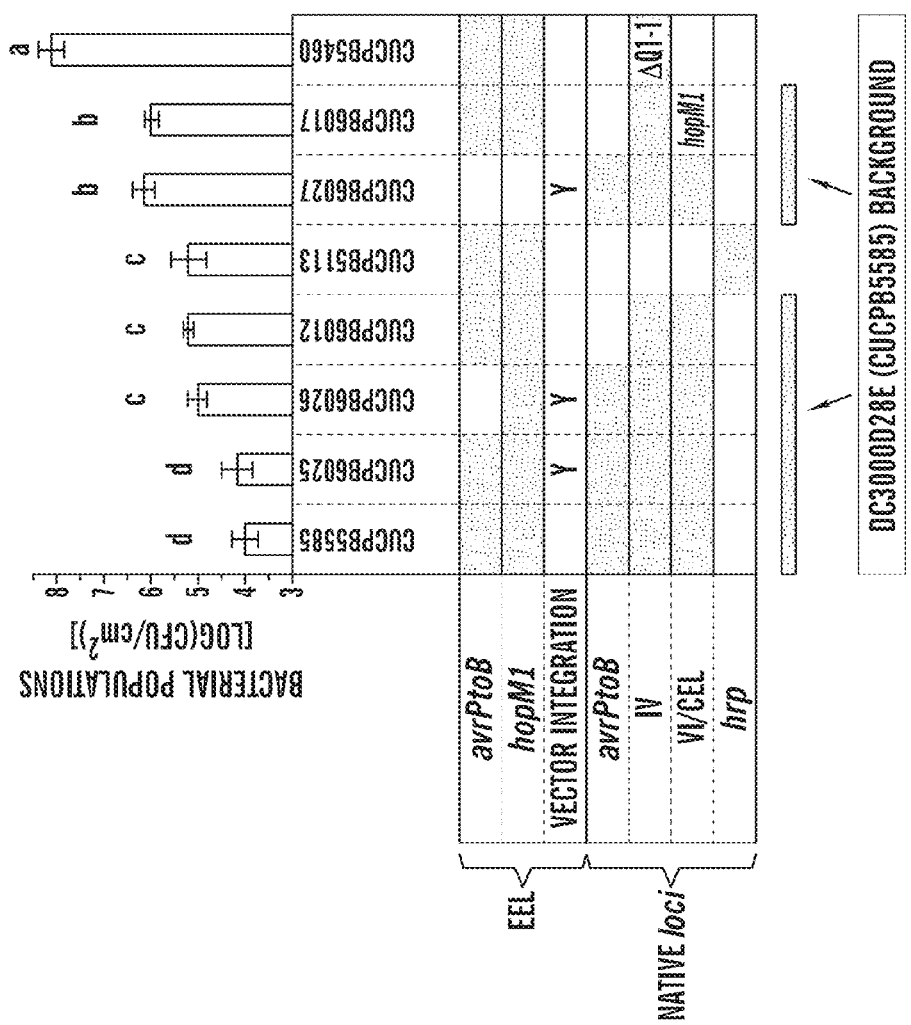

FIGS. 7A-7B show validation of the PRIVAS system using hopM1 and avrPtoB. Assays for growth of the indicated strains in N. benthamiana were performed as in FIGS. 1 and 5. The bars reflect the means and SD of CFU counts at 6 dpi calculated from 4 replicate leaves. Means with the same letters are not statistically different (α=0.05) based on a Tukey's HSD test. In both experiments, strains were inoculated by N. benthamiana leaf infiltration of $3\times10^4$ CFU/ml. The grid below the bar plot describes the genotype of the strains both at the EEL (upper half) and at native genomic loci (lower halt). A gray filled cell indicates that the corresponding locus is either absent (EEL) or deleted (genome) and a white fill signifies that the locus is either wild type (genome) or integrated at the EEL. A "Y" in the vector integration row denotes that the pCPP6219 plasmid or derivative was integrated at the EEL. In FIG. 7A, complementation of shcM-hopM1 at the EEL using PRIVAS fully restores the growth of the polymutant strain CUCPB5515 defective for the AvrE REG. Population levels of CUCPB6024 carrying the shcM-hopM1 at the EEL are not different from those of CUCPB5440, which harbors the entire native CEL and are about 1.5 logs higher than the AvrE REG-defective strains CUCPB5515 or CUCPB6023 (CUCPB5515+pCPP6219). CUCPB5460 serves as a reference for maximal growth in *N. benthamiana*. In FIG. 7B, complementation of avrPtoB alone or avrPtoB and shcM-hopM1 at the EEL using PRIVAS phenocopy wild-type restoration of the corresponding genes at their native genomic location. CUCPB6026 carrying avrPtoB at the EEL in a DC3000D28E background accumulates to the same extent as its natively restored counterpart CUCPB6012. Likewise, the growth of CUCPB6027 (avrPtoB and shcM-hopM1 at the EEL in DC3000D28E) is indistinguishable from CUCPB6017. CUCPB5460, CUCPB5113, and CUCPB5585 serve as references in *N. benthamiana* for respectively, maximal growth, T3SS-independent background growth, and minimal growth exhibited by DC3000D28E.

Figure 8A:
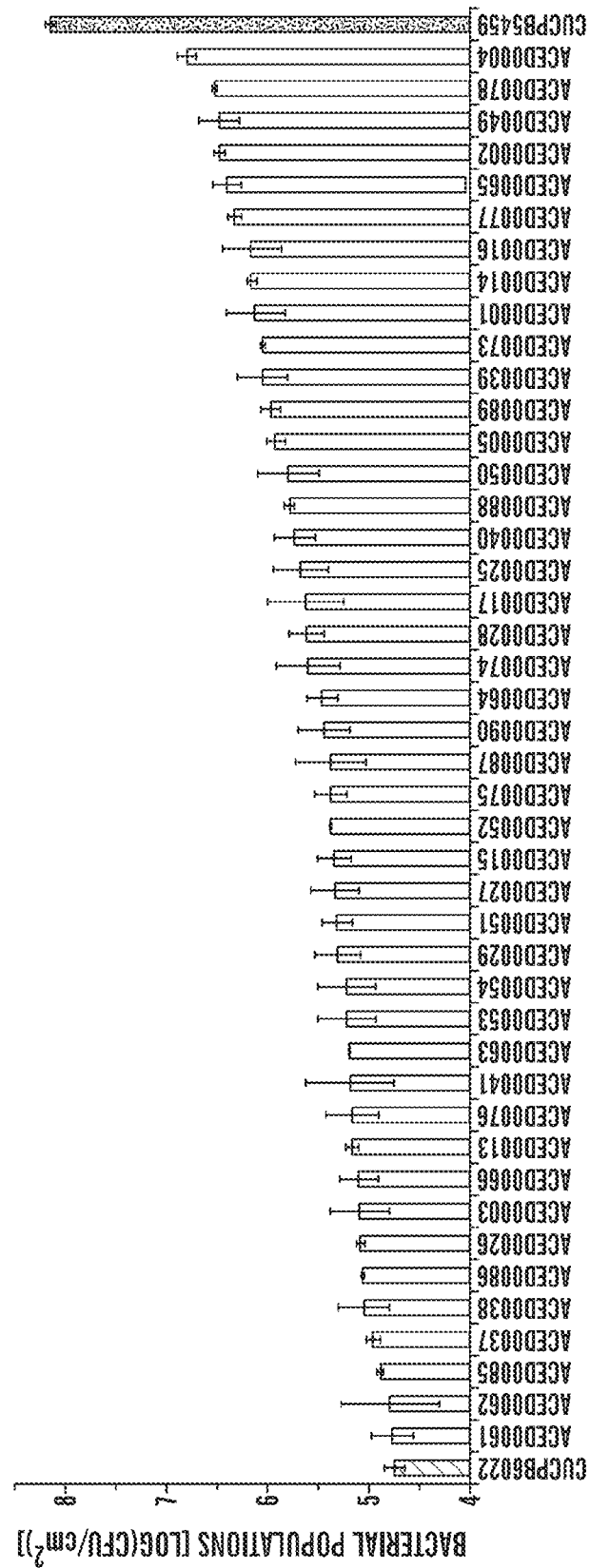
Figure 8B:
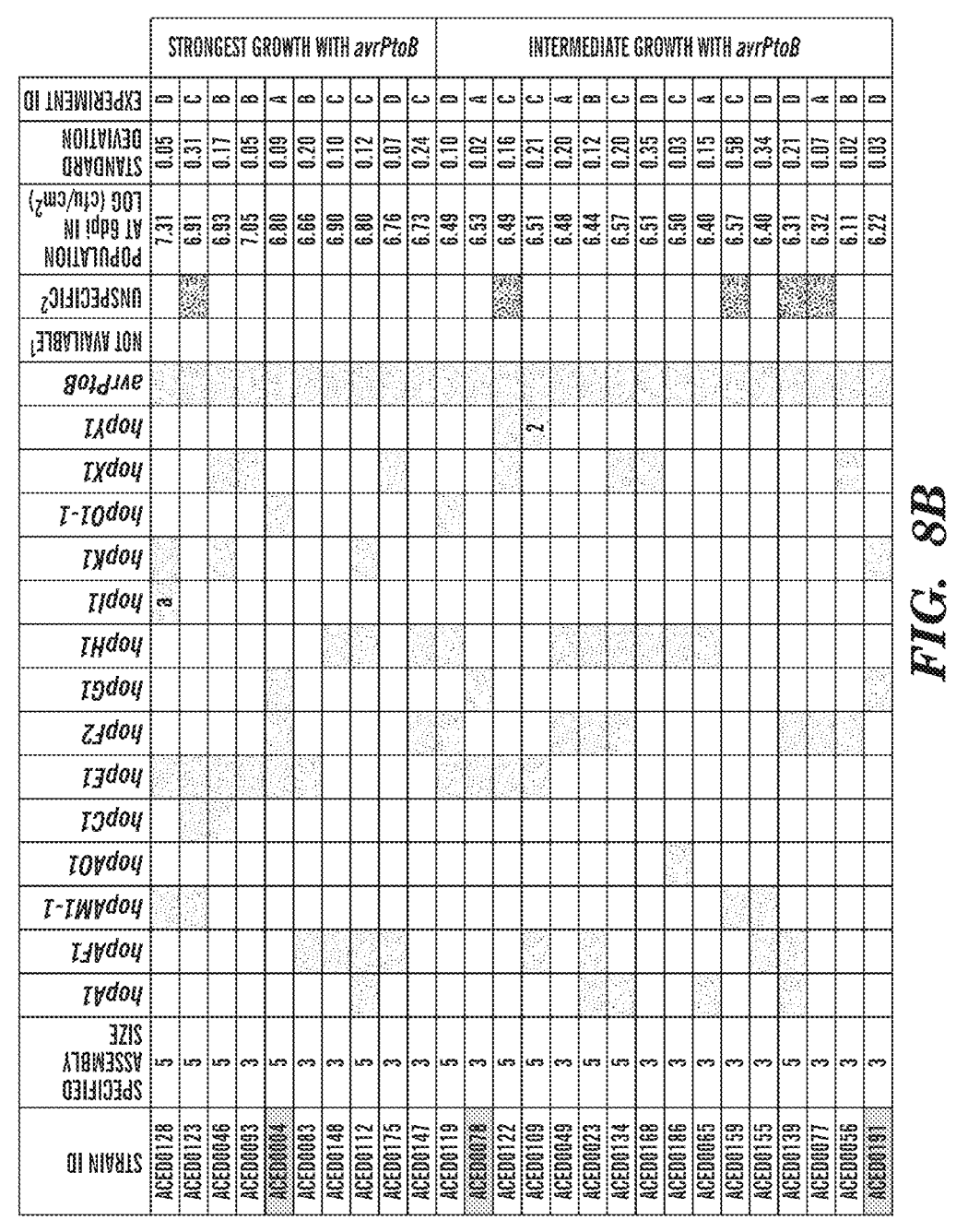

FIG. 8 shows the growth in *N. benthamiana* of CUCPB6016-PRIVAS strains containing GUs randomly assembled from a pool of 15 GUs and identification of effector genes underlying different growth phenotypes. FIG. 8A provides a representative example of the growth data obtained with one of the four batches of 44 strains from the CUCPB6016-PRIVAS library screened for enhanced growth at 6 dpi. Strains are ordered by increasing mean population levels (n=2) with error bars representing the SD. FIG. 8B shows the cluster composition and growth phenotypical classes of a subset of selected strains. Following growth profiling as illustrated in FIG. 8A for each of the four batches ("Experiment ID" column), approximately 10 strains from each tail of the distribution (least and best performing) were selected for PCR amplification of the entire engineered cluster. The table of FIG. 8B summarizes the composition in GUs and the in planta growth data for 56 of this set of selected strains whose clusters could be successfully PCR-amplified and the underlying GUs subsequently identified by partial sequencing. Strains that have their ID background shaded promoted a visible chlorosis in the inoculated leaf area at 10 dpi. Blue (GUs) or light salmon shading indicates that the feature in the corresponding column was detected in the cluster. For GUs that contain several effectors, the name of first effector gene of the operon is used in the column heading. Numbers indicate the number of times the feature was found on the cluster in distinct locations, and the bottom row shows the total number of occurrences of the feature across the set of clusters. (1) When sequencing reactions with FA-specific oligonucleotides failed to produce an exploitable sequence the nature of the downstream GU was deemed "Not available". (2) Sequencing reactions produced DC3000 sequences outside of the pool of GUs. These illegitimate GUs presumably derive from non-specific amplification at the primary PCR stage. (a) Partial internal deletion of the HopI1 CDS. (b) Chimeric hopA1-hopY1. (c) Complete HopY1 CDS deleted but flanking sequences appear unaffected.

Figure 9A:
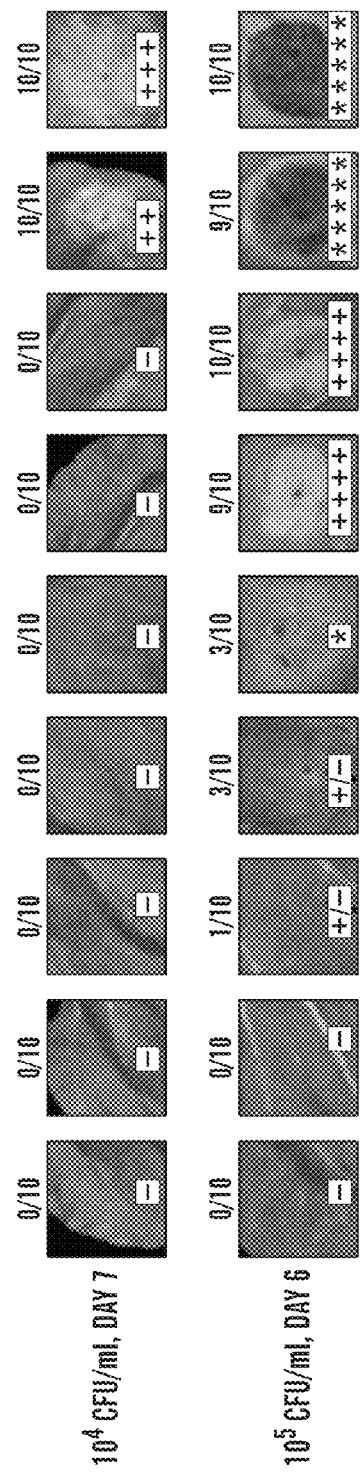
Figure 9B:
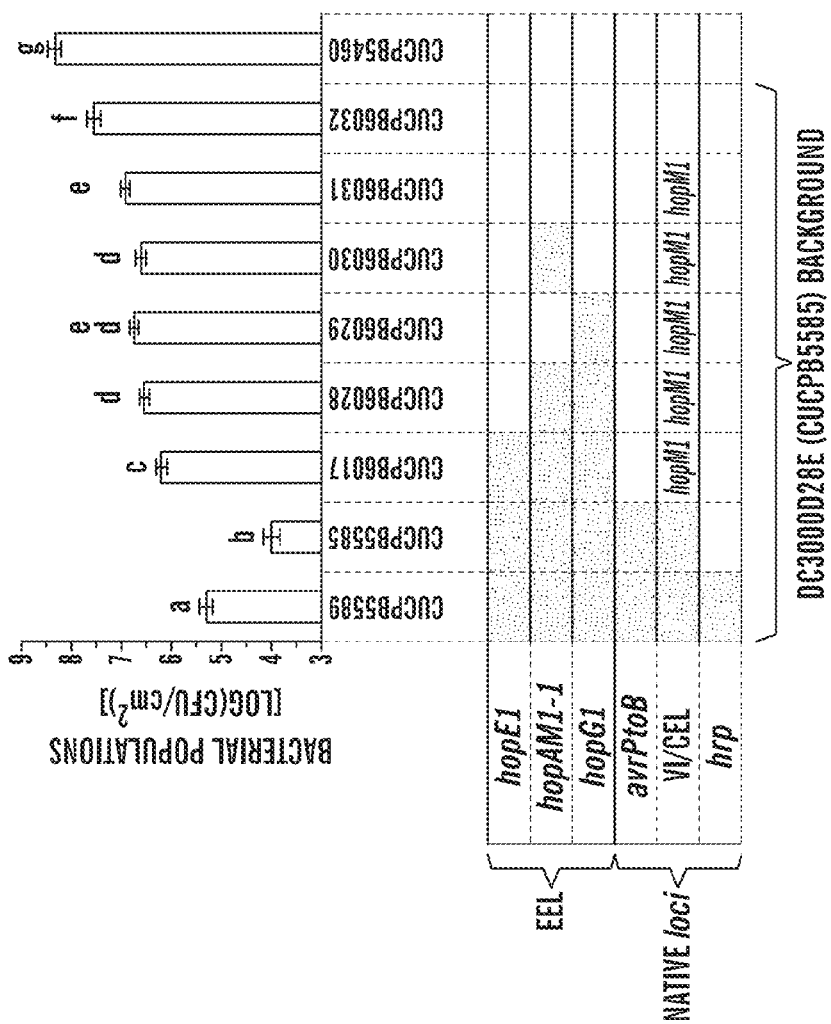

FIGS. 9A-9B show that successive PRIVAS-mediated integration of 8 T3Es into DC3000D28E reveals a hierarchy contributing to chlorosis, lesion formation, and near wild-type growth in *N. benthamiana*. PRIVAS was employed in programmed mode to create various combinations of hopE1, hopAM1-1 and hopG1. The resulting gene sets were integrated at the EEL of DC3000D28E derivatives CUCPB6017 or CUCPB6019, which had avrPtoB and, respectively, hopM1 or the entire CEL natively restored, as indicated by white-filled cells in the genotype grid. Symptoms in *N. benthamiana* leaves are depicted in the photomicrograph of FIG. 9A. Leaves were infiltrated with two levels of inoculum and the plants were kept in a chamber with 70-80% RH. The fraction of plants showing symptoms and the nature of symptoms scored is shown: '+' indicates chlorosis and '*' indicates cell death. FIG. 9B graphs bacterial growth in *N. benthamiana*. Bacteria were inoculated at $3\times10^4$ CFU/ml and populations measured 6 dpi. The least-squares means±SD of log ($CFU/cm^2$) is shown. Means with the same letter are not significantly different using the Tukey-Kramer multiple comparisons method ($\alpha=0.05$). Eight independent experiments were performed with different subsets of the 9 strains shown, with a minimum of 3 plants per strain in every experiment and a total of 213 data points. Randomized block design was used for data analysis using the statistical analysis program SAS.

Figure 10:
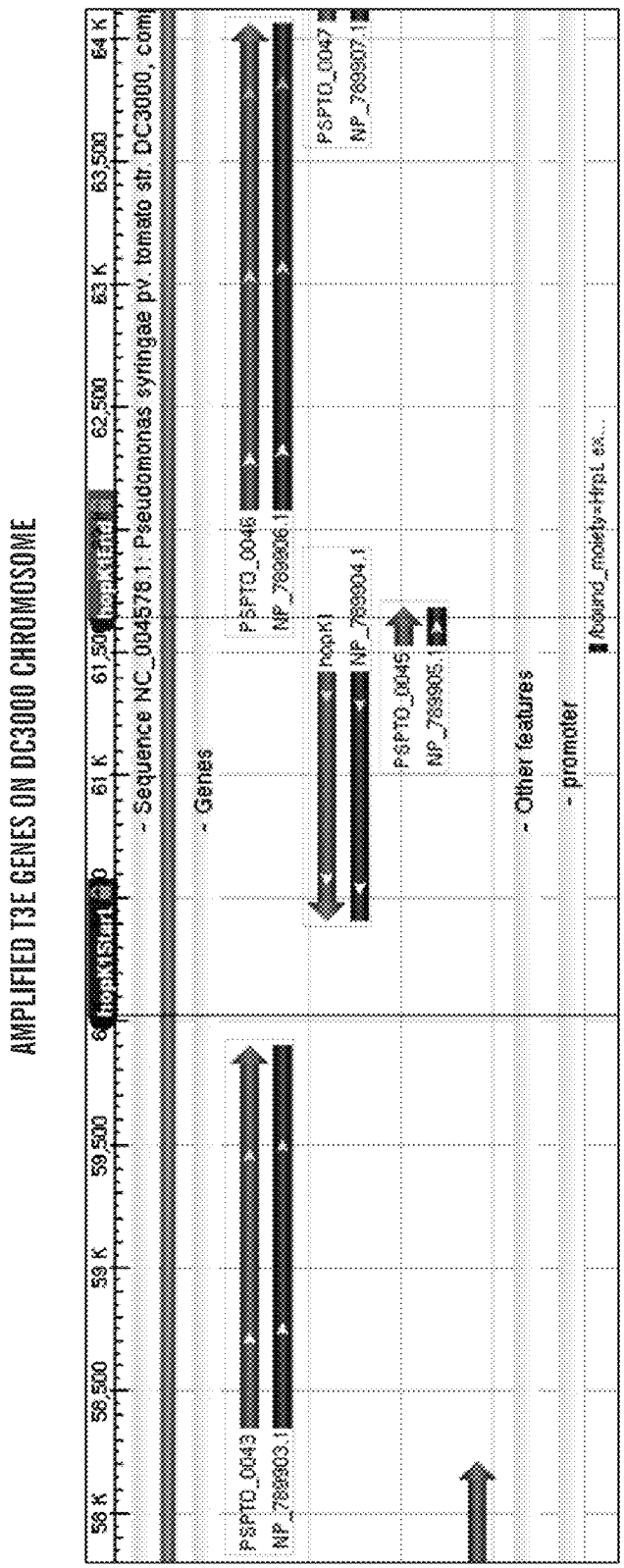
Figure 10:
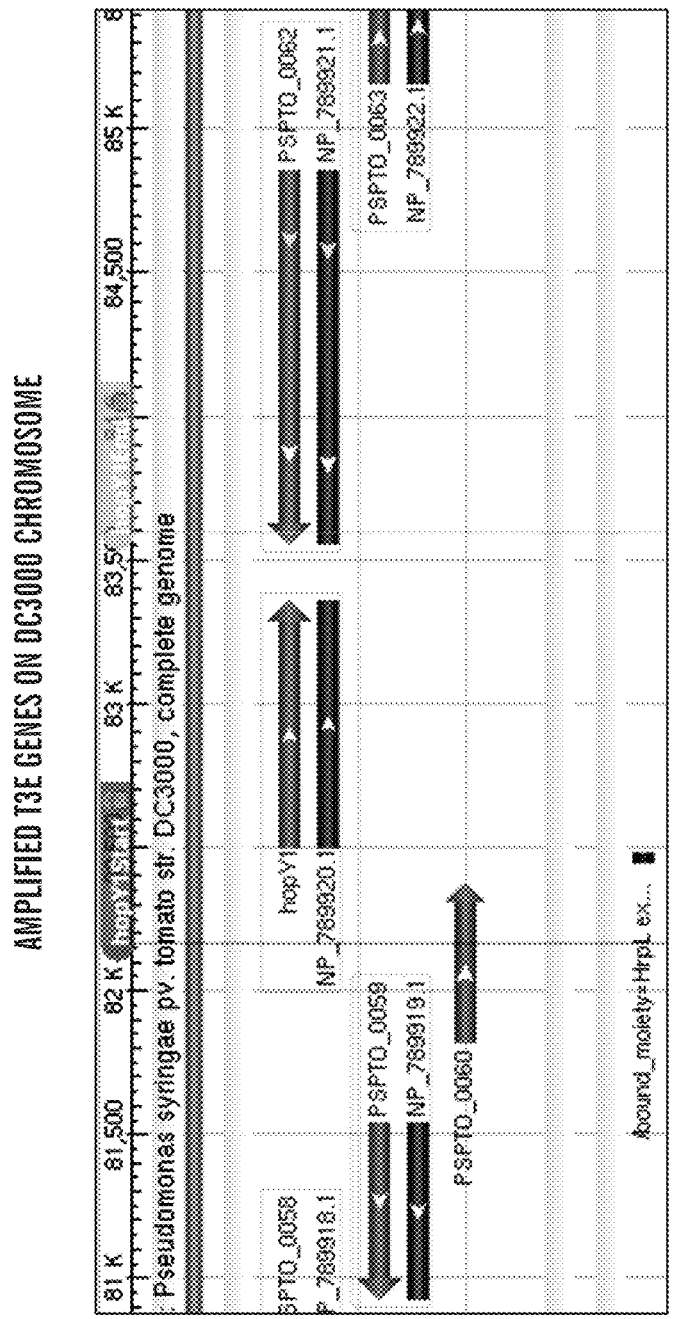
Figure 10:
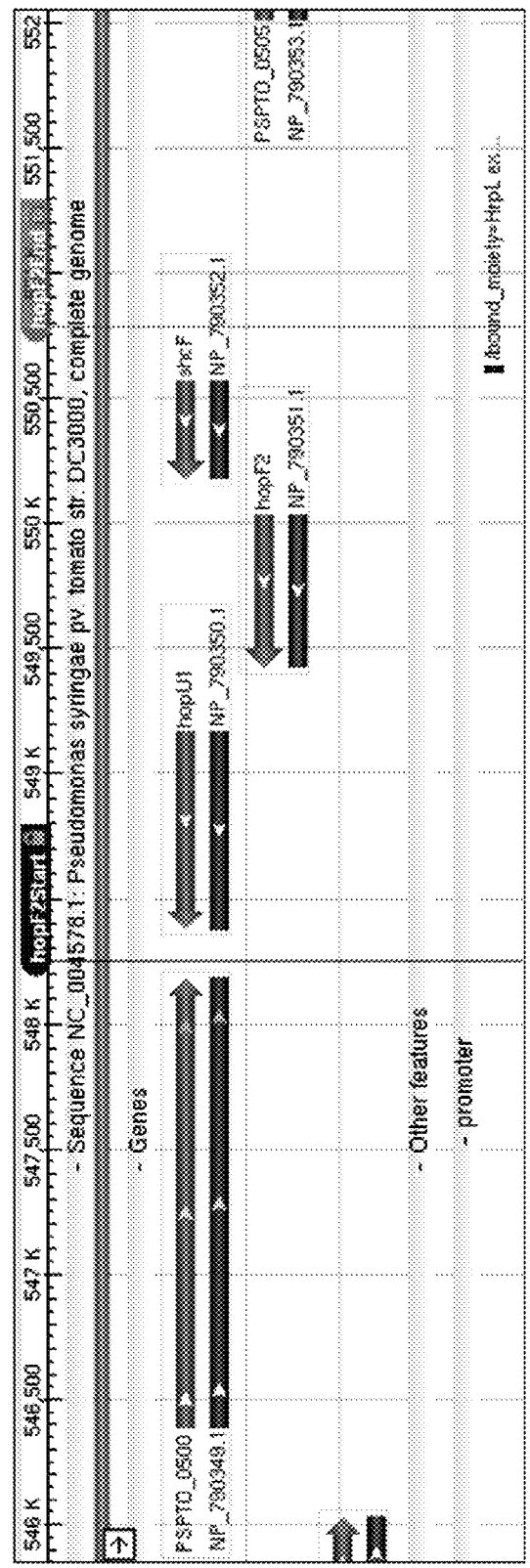
Figure 10:
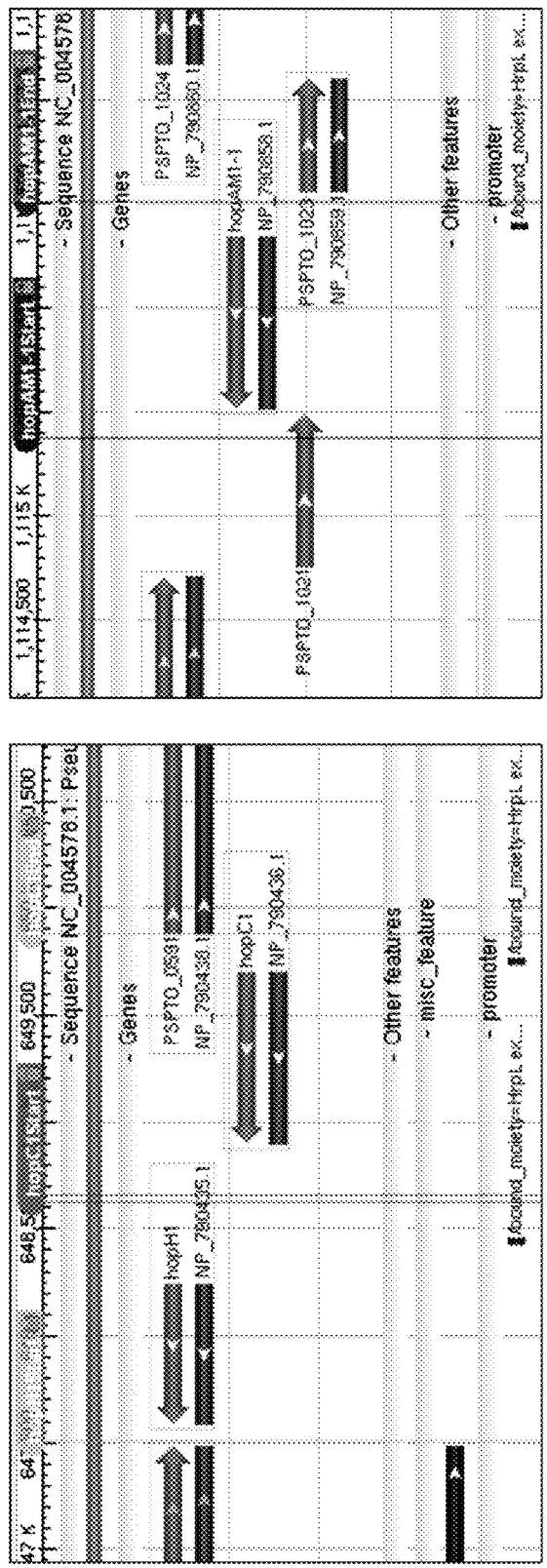
Figure 10:
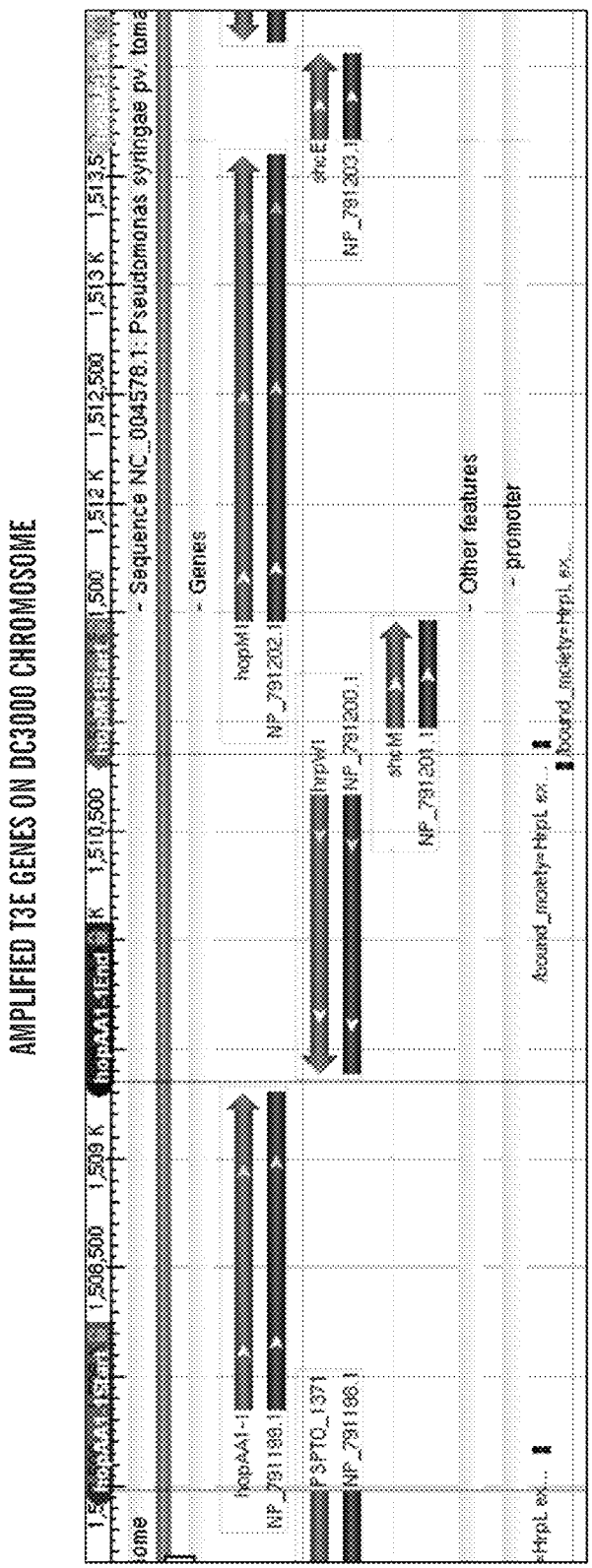
Figure 10:
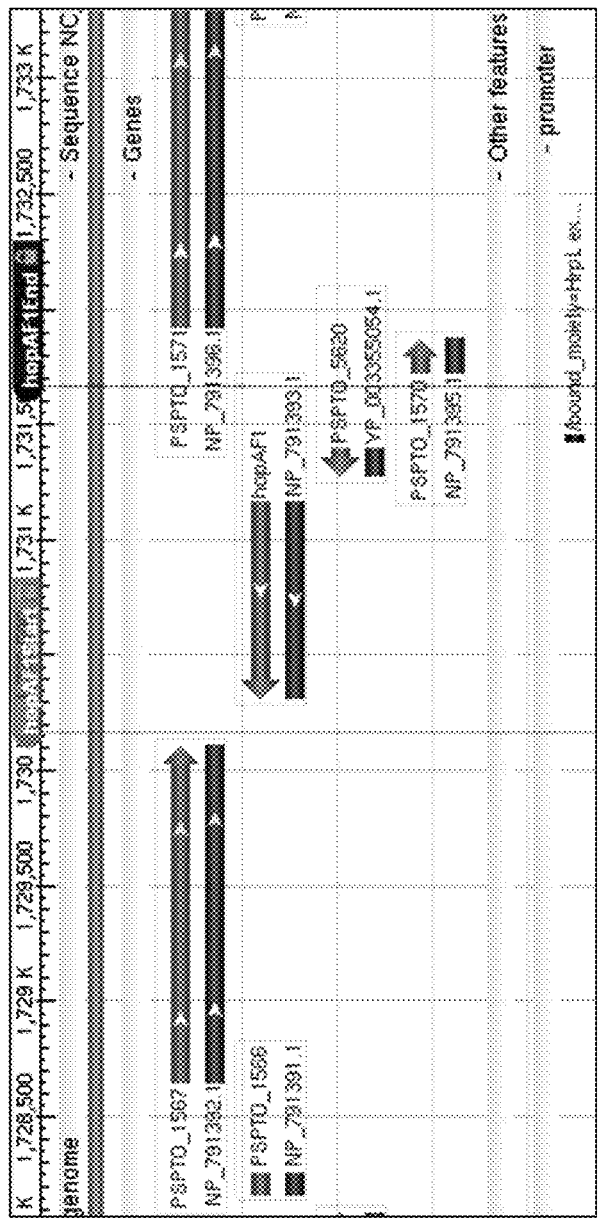
Figure 10:
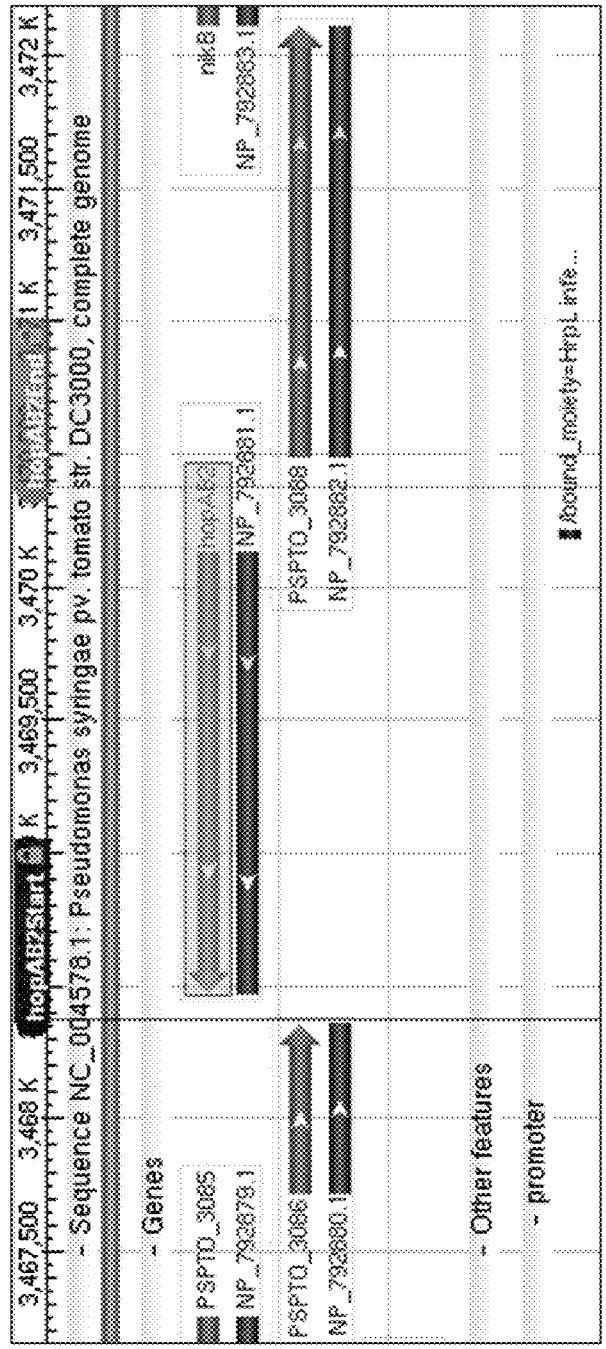
Figure 10:
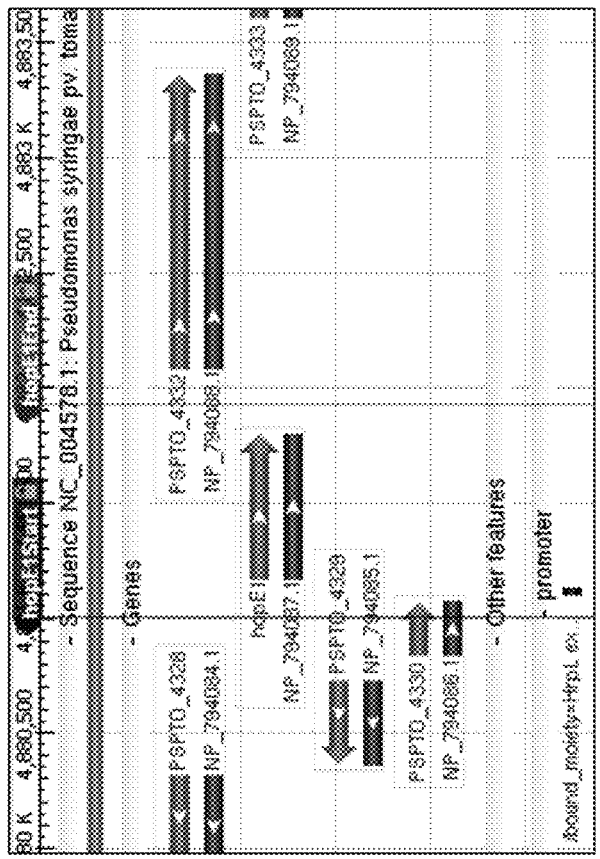
Figure 10:
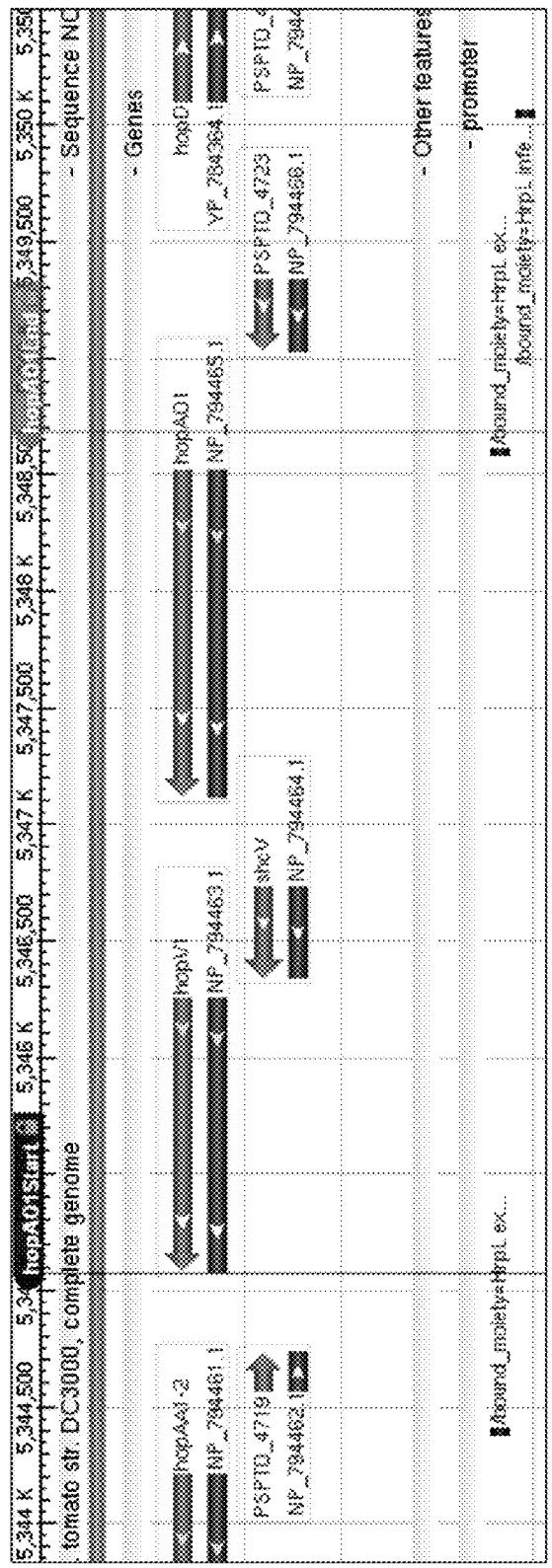
Figure 10:
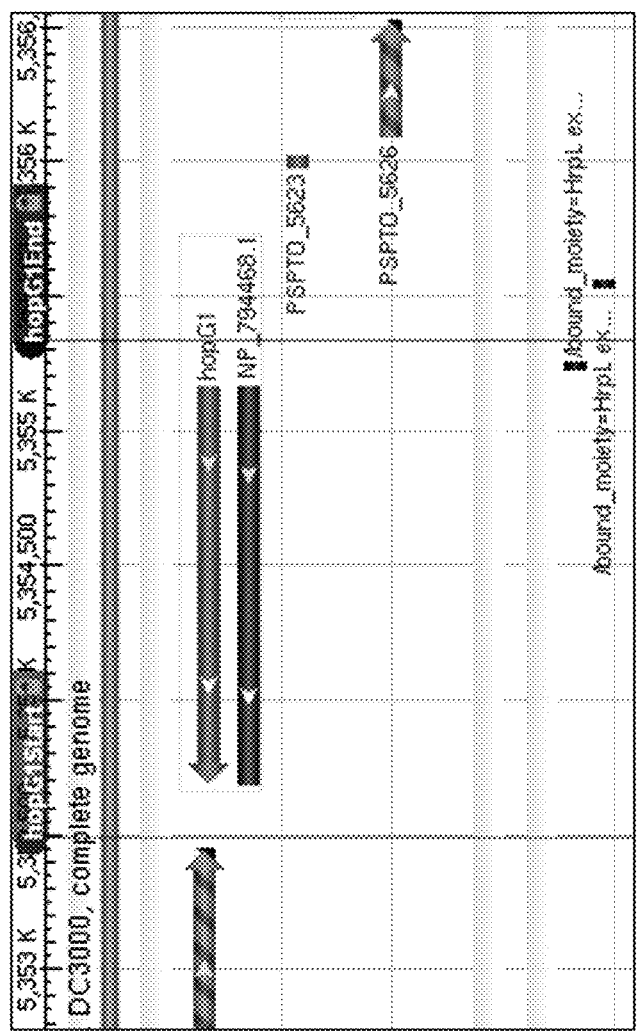
Figure 10:
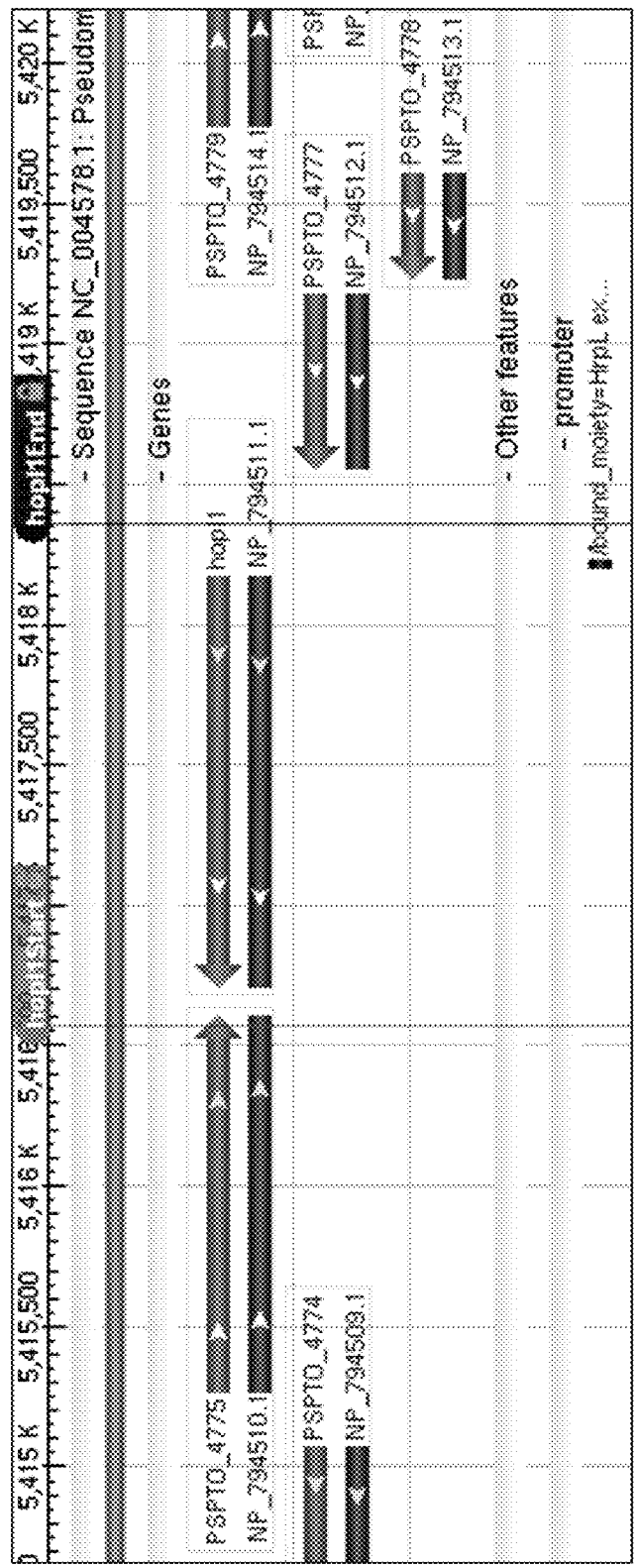
Figure 10:
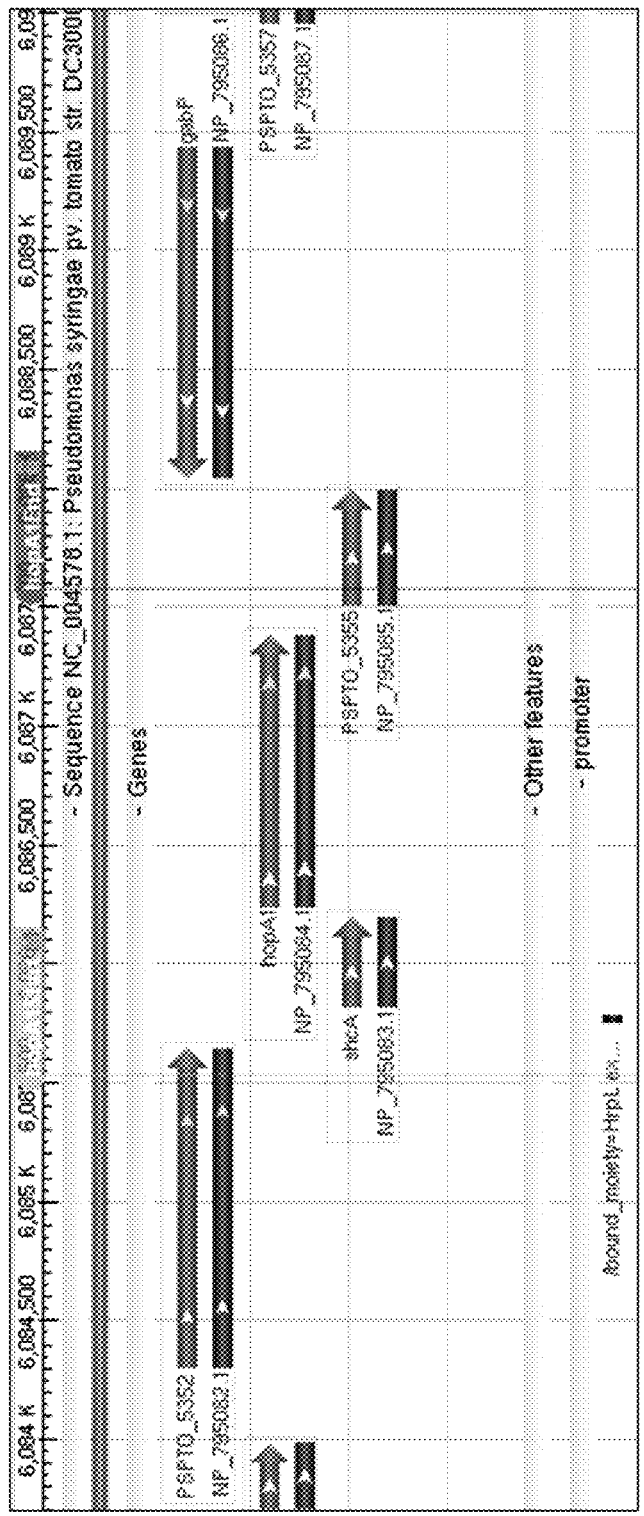
Figure 10:
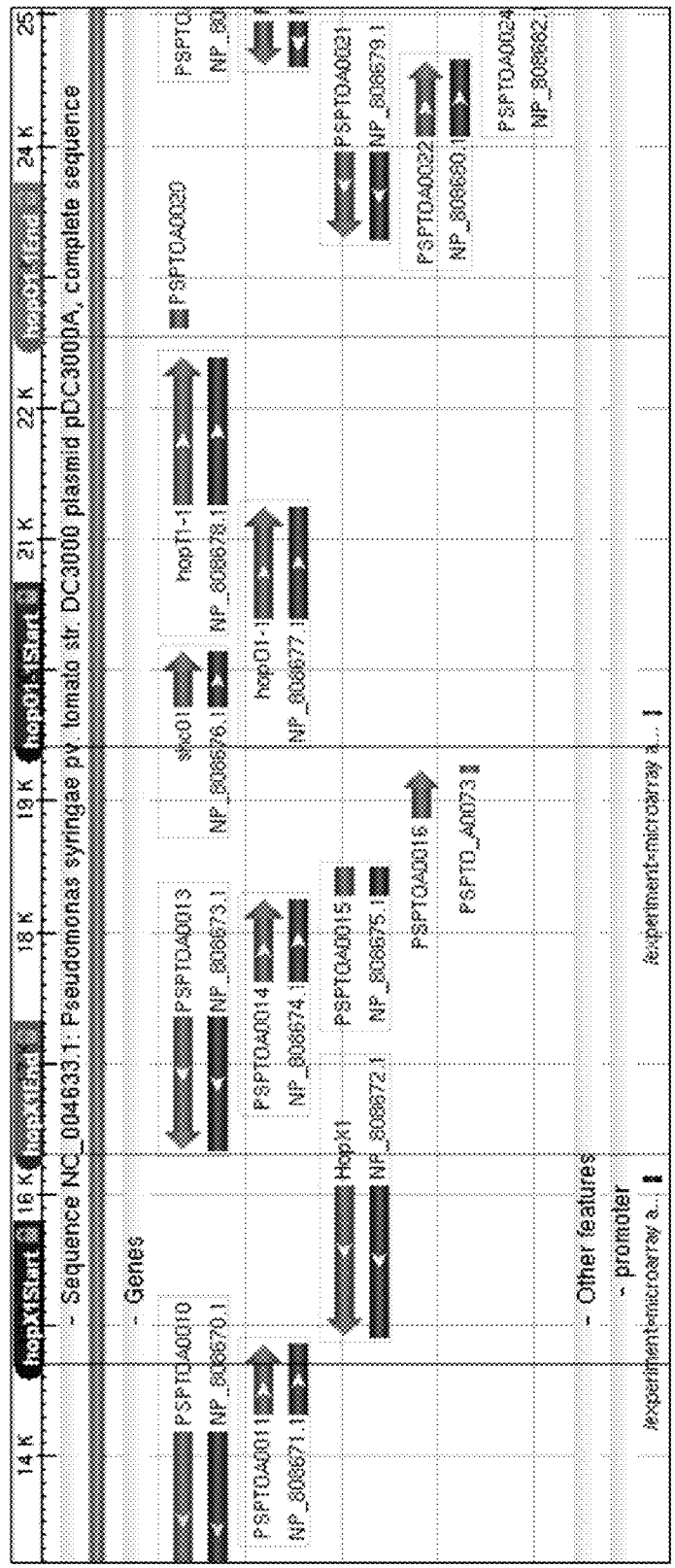

FIG. 10 provides an illustration of the amplified type III effector (T3E) genes of *P. syringae* pv. *tomato* DC3000 displayed in genomic context. The figure provides graphical displays for relevant T3E genes on the chromosome and on plasmid pDC3000A.

Figure 11A:
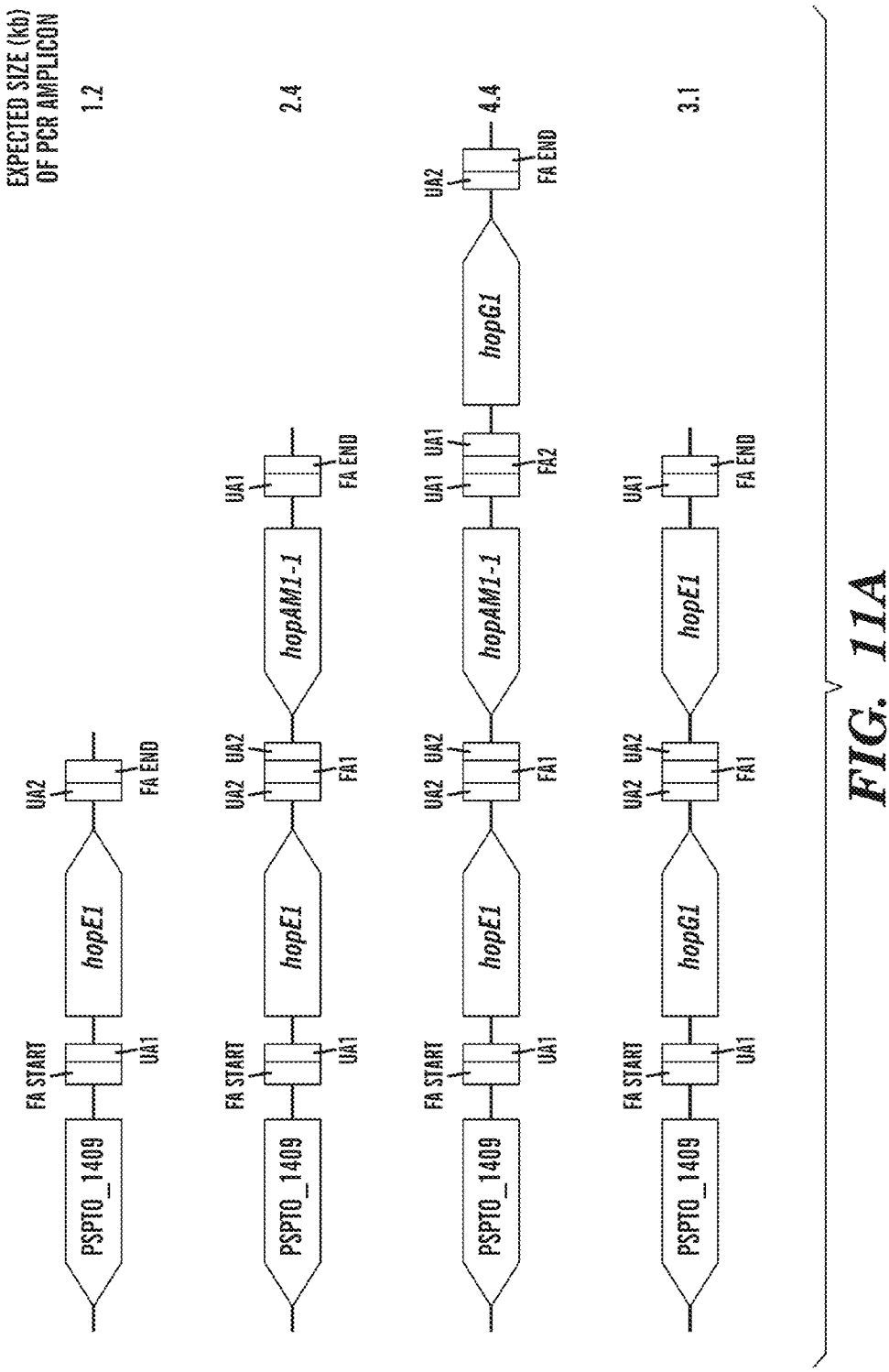
Figure 11B:
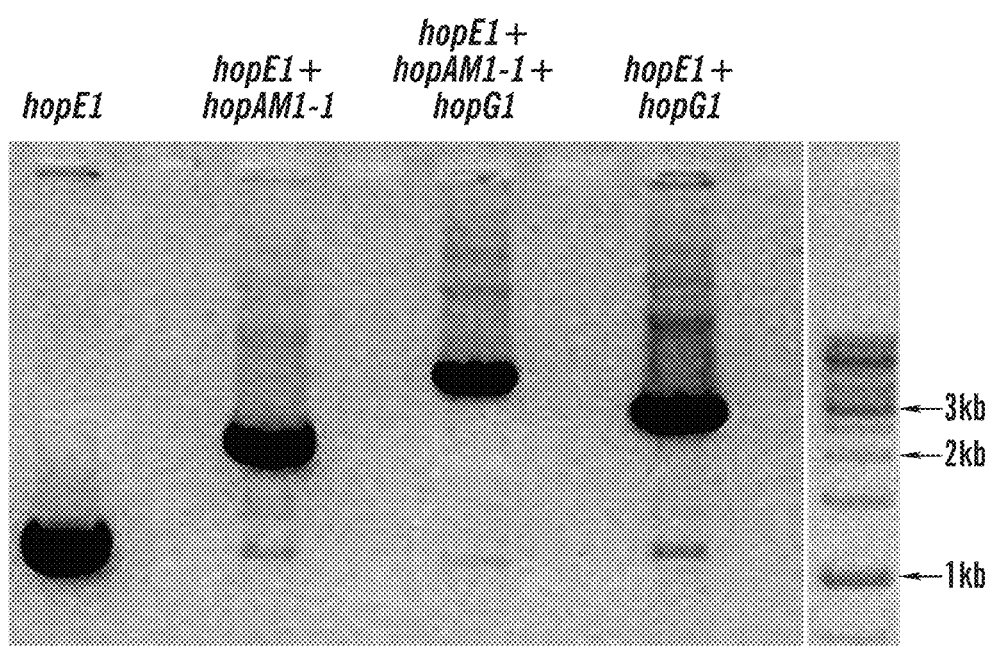

FIGS. 11A-11B show the configuration and colony PCR verification of the programmed clusters harboring various combinations of the hopE1, hopAM1-1 or hopG1 T3E genes. FIG. 11A is a graphical representation of the configuration of the programmed T3E gene clusters integrated in the *P. syringae* strains of FIG. 9. The colored arrows symbolize genes. Their orientation indicates the direction of the transcription of the corresponding operons. The invariable PSPTO_1409 arrow corresponds to the region of the pCPP6218 shuttle vector undergoing homologous recombination for genomic integration. The expected sizes of the colony PCR amplicons of the gene clusters are provided on the right. Critical DNA features used in assemblies are color coded and the color keys are provided in the box below. FIG. 11B shows an ethidium bromide-stained agarose gel of the gene clusters described above amplified by colony PCR. The size of the relevant bands of the DNA ladder run on the right hand side is indicated.

Figure 12A:
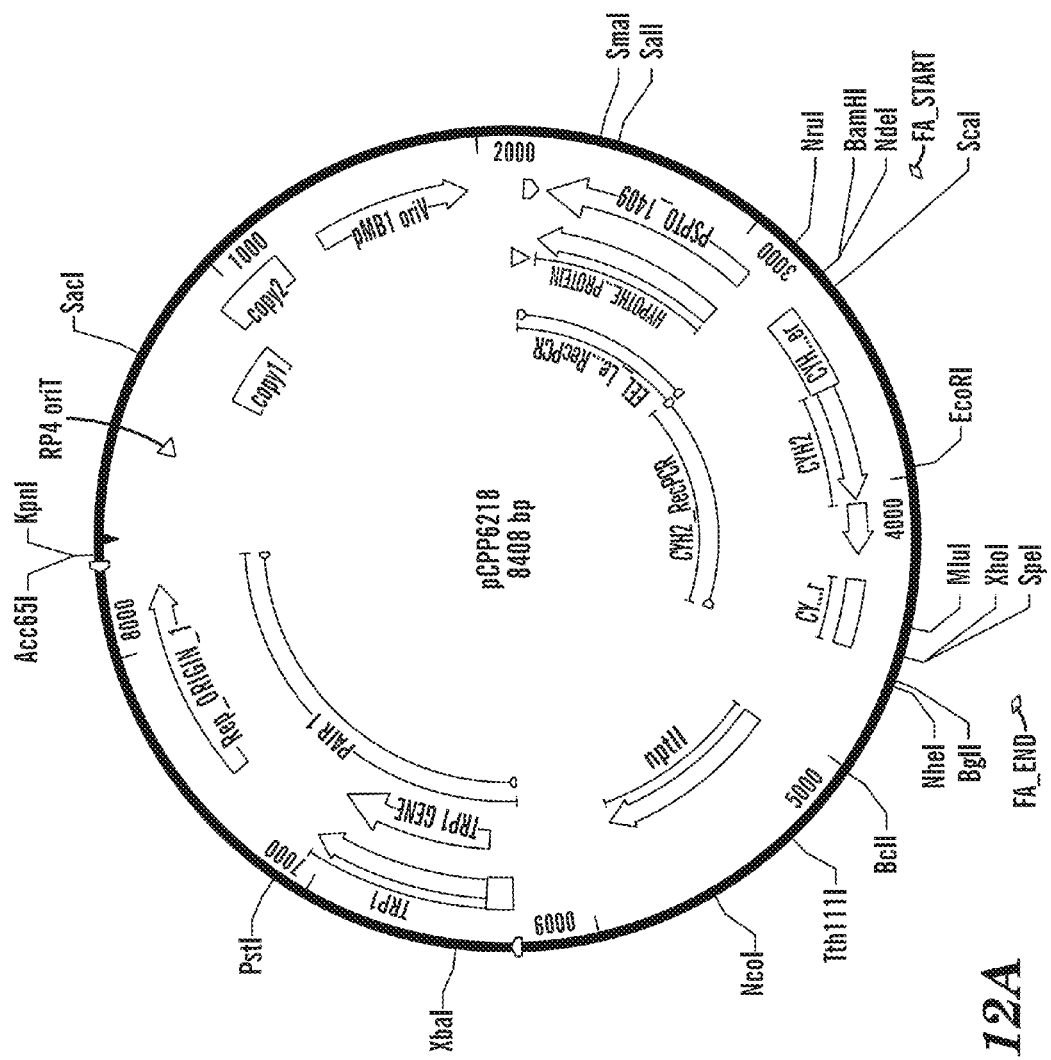
Figure 12B:
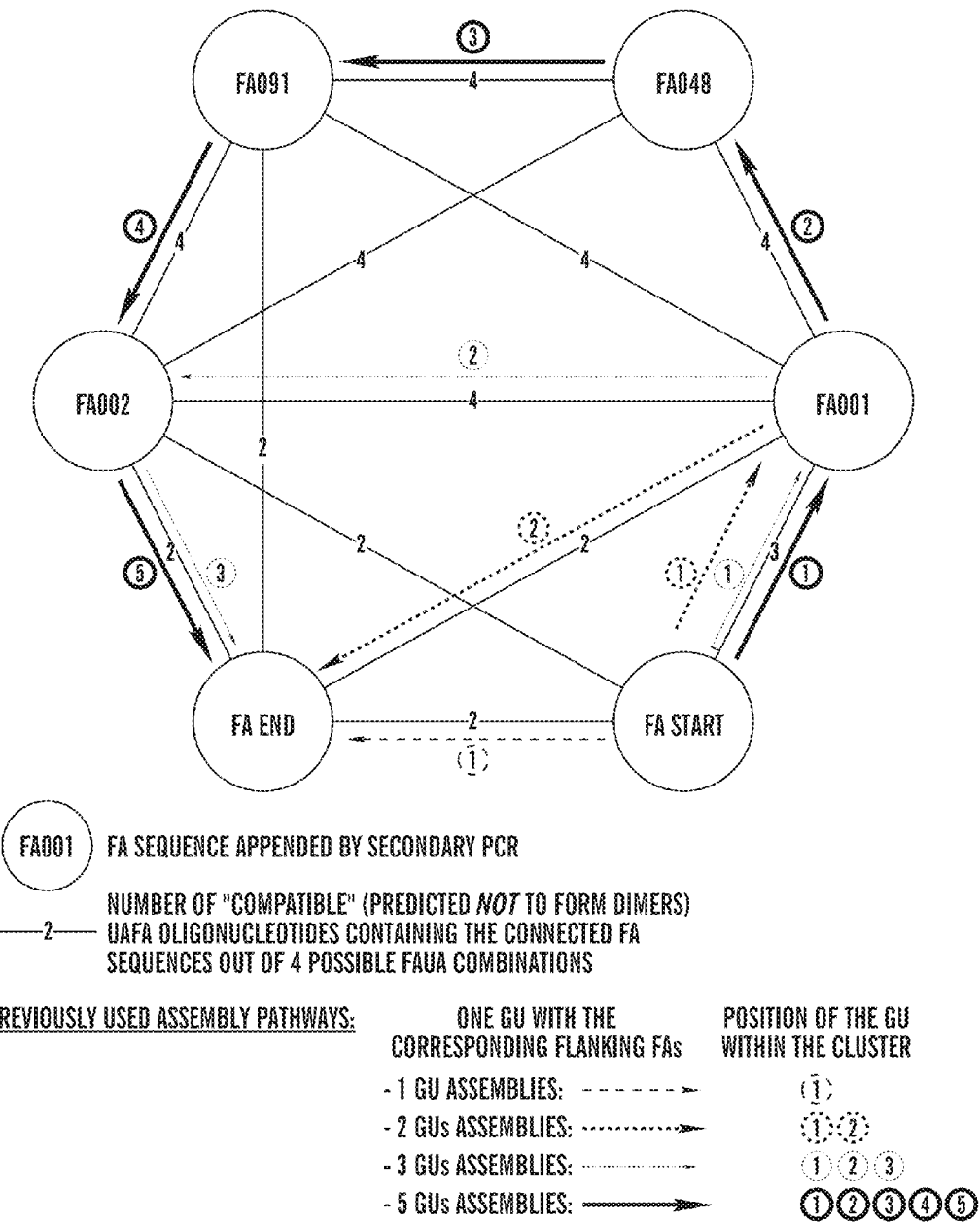
Figure 12C:
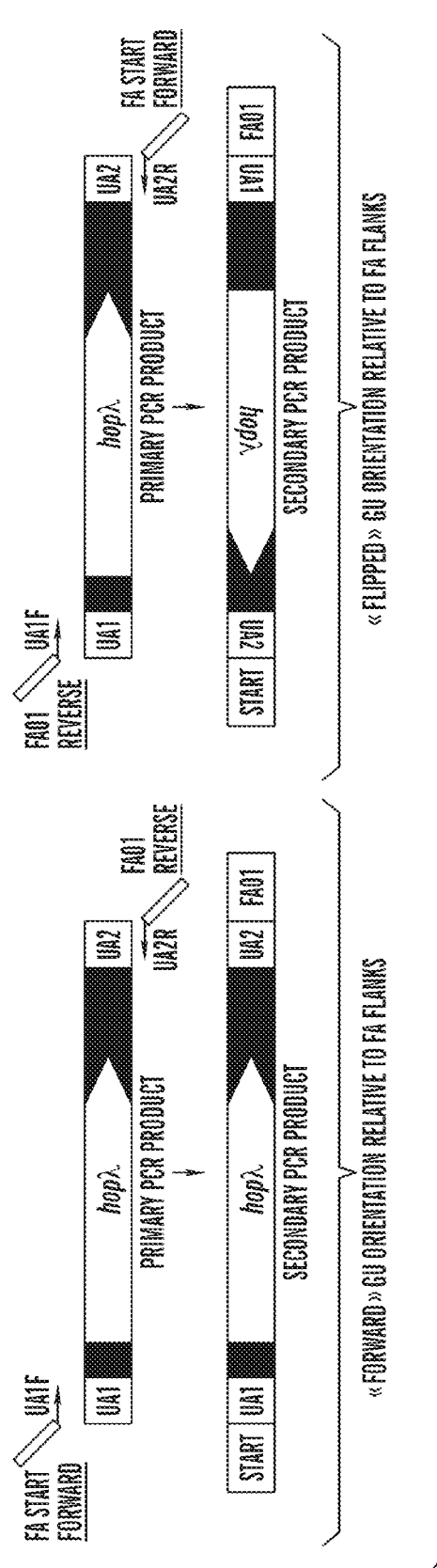

FIGS. 12A-12C show the PRIVAS vector and pathways for genetic unit (GU) assembly and orientation flipping. FIG. 12A is a map of PRIVAS vector cPP6218, which carries replication origins and selectable markers for bacteria and yeast, sites for recombination in yeast with FA-flanked Gus, and PSPT01409 sequences enabling recombination with the exchangeable effector locus (EEL) of *P. syringae* pv. *tomato* DC300. FIG. 12B shows assembly pathways in the secondary PCR compatibility space of selected UAFA oligonucleotides. FIG. 12C is an illustration of the ability of UA1 and UA2 swaps in UAFA oligonucleotides to flip GU orientations in assemblies.

DETAILED DESCRIPTION OF THE INVENTION

A first aspect of the present invention relates to a method of assembling synthetic genetic constructs comprising a plurality of genetic units. This method involves providing a plurality of separate genetic units, each having 5' and 3' ends, and appending universal adapter oligonucleotides to the 5' and 3' ends of each separate genetic unit to form separate extended genetic units each having 5' and 3' ends. This method further involves attaching a set of flexible adapter oligonucleotides to the 5' and 3' ends of separate extended genetic units to form separate dual extended genetic units, and assembling together the separate dual extended genetic units via homologous recombination between the flexible adapter oligonucleotides of the dual extended genetic units to form the synthetic genetic constructs In accordance with this and all aspects of the present invention a separate genetic unit refers to a fragment or segment of genetic nucleic acid material (e.g., a DNA fragment). The genetic unit may comprise deoxyribonucleotides, ribonucleotides, nucleotide analogs, peptide nucleotides, or combinations thereof that encode at least a portion of a gene, one or more function domains and/or modules of a single multi-domain gene, a complete gene, a chimeric gene, or two or more genes. The genetic unit can be double stranded or single stranded and preferably comprises appropriate upstream promoter and/or enhancer regions and downstream transcription termination regions. The nucleotide sequence of the genetic unit can be completely artificial or it can be derived from any living, natural or synthetic organism including, but not limited to, animals, plants, archaebacteria, eubacteria, fungi, protists and viruses, or any combination thereof. Genetic units can originate from any source, including a cellular or tissue nucleic acid sample, cloned fragments or subclones thereof, chemically synthesized nucleic acids, genomic nucleic acid samples, cDNAs, nucleic acid molecules obtained from nucleic acid libraries, etc. The genetic units may comprise a wildtype, i.e., normal nucleotide sequence, or a modified, variant, or optimized (e.g., codon optimized) nucleotide sequence. In one embodiment of the present invention, the separate genetic units are modified or mutated prior to assembly. The separate genetic units of the invention can vary in size from each other, each unit ranging in size from between about 1 nucleotide base (b) to about 1 Megabase (Mb). For example, genetic units of the invention may be 1 b, 5 bs, 10 bs, 15 bs, 20 bs, 30 bs, 40 bs, 60 bs, 80 bs, 100 bs, 500 bs, 1 kilobase (kb), 3 kb, 5 kb, 10 kb, 15 kb, 20 kb, 40 kb, 60 kb, 80 kb, 100 kb, 250 kb, 500 kb, 750 kb, or 1 Mb.

In accordance with this aspect of the present invention, the universal adapter (UA) oligonucleotides are short adapter or linker sequences, e.g., between about 4-33 nucleotides in length, more preferably between 18-20 nucleotides length, that are appended to both ends of each separate genetic unit to form separate extended genetic units. A universal adapter oligonucleotide set of the present invention comprises a first universal adapter oligonucleotide that is appended to one end of a genetic unit (i.e., either the 5' or the 3' end), and a second universal adapter oligonucleotide, having a different nucleotide sequence than the first universal adapter oligonucleotide, that is attached to the opposite end of the same genetic unit. In carrying out the method of assembling genetic units of the invention, it is preferable to append one set of universal adapter oligonucleotides (i.e., UA1 and UA2) to each genetic unit to be assembled; however, in some embodiments of the invention, it may be desirable to use more than one set of universal adapter oligonucleotides. Exemplary adapter oligonucleotide sequences are disclosed herein (see e.g., SEQ ID NOs: 21 and 22); however, a wide variety of universal adapter oligonucleotide sequences can be utilized, and the design and generation of such universal adapter oligonucleotides is well within the level of skill of one in the art.

The universal adapter oligonucleotides can be appended to the 5' and 3' ends of each separate genetic unit using methods known in the art. For example, in one embodiment of the present invention, universal adapter oligonucleotides are appended to genetic units using a polymerase enzyme, for example, a DNA polymerase enzyme, and carrying out a polymerase chain reaction. In accordance with this embodiment, a plurality of universal adapter oligonucleotide primer sets are provided where each primer set comprises a first oligonucleotide primer comprising a genetic unit specific portion and a 5' universal adapter specific portion, and a second oligonucleotide primer comprising a genetic unit specific portion and a 5' universal adapter specific portion. A polymerase is provided and the universal adapter oligonucleotide primer sets, the polymerase and the one or more separate genetic units are blended to form a polymerase chain reaction mixture. The mixture is subject to one or more polymerase chain reaction cycles to append the universal adapter oligonucleotides to 5' and 3' ends of each genetic unit in the sample. Alternatively, where the genetic units comprise ribonucleic acids, a reverse transcriptase enzyme is used to append the universal adapter oligonucleotides to the genetic units in a reverse transcription reaction.

In another embodiment of the present invention the universal adapter oligonucleotides are appended to the separate genetic units to form extended genetic units using an exonuclease digestion followed by ligation as described in U.S. Patent Publication No. US2010/0035768 to Gibson et al., which is hereby incorporated by reference in its entirety. In accordance with this method the universal adapters comprise a genetic unit-specific region and a universal adapter specific portion and are provided as double-stranded adapter units. The exonuclease digestion chews back a sufficient number of nucleotides on each end of a double stranded genetic unit and universal adapter to allow for specific annealing of the exposed single-stranded regions of homology between the genetic units and universal adapter oligonucleotides. The exonuclease digestion may be carried out by a polymerase in the absence of dNTPs (e.g., T5 polymerase) or by an exonuclease, such as exonuclease III. Following annealing, single stranded gaps left by the exonuclease are filled in using a suitable thermostable non-strand-displacing DNA polymerase and nicks are sealed with a thermostable ligase.

In another embodiment of the present invention the adapter oligonucleotides are appended to the separate genetic units to form extended genetic units using a restriction enzyme digestion followed by ligation using a ligase. A particularly suitable method for appending the adapter oligonucleotides to the genetic units involves the use of Type II restriction enzymes as described by Engler et al., "Golden Gate Shuffling: A One Pot DNA Shuffling Method Based on Type IIs Restriction Enzymes," PLOS One 4(5):e5553 (2009) (which is hereby incorporated by reference in its entirety). In accordance with this method, ends of the genetic units and double stranded universal adapters are designed to include type II restriction sites such that digestion with a type II restriction enzyme removes the enzyme recognition sites and generates end with complementary four nucleotide overhangs that can than be ligated seamlessly.

In yet another embodiment of the present invention, separate extended genetic units comprising a genetic unit and universal adapter oligonucleotides can be chemically synthesized.

The flexible adapter oligonucleotides utilized in the methods of the present invention are also short terminal adapters or linkers that comprise a universal adapter specific portion (i.e., a portion that is complementary to a segment of a universal adaptor oligonucleotide sequence) and a flexible adapter specific portion. The flexible adapter specific portion of the flexible adapter oligonucleotide can range in length from between about four nucleotides to about 40 nucleotides, preferably about 35 nucleotides long and the universal adapter specific portion of the flexible adapter oligonucleotide is about 4-33 nucleotides preferably about 18-20 nucleotides long.

A flexible adapter oligonucleotide set of the present invention comprises a first flexible adapter oligonucleotide that is appended to one end of an extended genetic unit (i.e., either the 5' or the 3' end), and a second flexible adapter oligonucleotide, having the same or a different nucleotide sequence than the first flexible adapter oligonucleotide, that is attached to the opposite end of the same extended genetic unit. In carrying out the method of assembling genetic units of the invention, various sets of flexible adapter oligonucleotides are utilized, with the various sets comprising flexible adapter oligonucleotides that have the same and different flexible adapter specific sequences as other sets of flexible adapter oligonucleotides.

The flexible adapter oligonucleotides are attached to the separate extended genetic units (i.e., genetic units containing universal adapter oligonucleotides) to form dual extended genetic units. The flexible adapters are attached to the 5' and 3' ends of the extended genetic units using methods well known in the art, including the use of a polymerases, exonucleases, restriction enzymes, and ligases as described above for the attachment of universal adapter oligonucleotides. Alternatively, separate extended genetic units comprising a genetic unit with universal adapter oligonucleotides and flexible adapter oligonucleotides can be chemically synthesized.

In one embodiment of the present invention, the flexible adapter oligonucleotides are attached to the separate extended genetic units using a polymerase chain reaction. In accordance with this embodiment, a plurality of flexible adapter oligonucleotide (FA) primer sets are provided, each primer set comprising a first oligonucleotide primer comprising an universal adapter specific portion and a 5' flexible adapter specific portion, and a second oligonucleotide primer comprising an universal adapter specific portion and a 5' flexible adapter specific portion. A polymerase is provided and the flexible adapter oligonucleotide primer sets, the polymerase and the one or more separate extended genetic units are blended to form a polymerase chain reaction mixture. The mixture is subject to one or more polymerase chain reaction cycles to attach the flexible adapter oligonucleotides to 5' and 3' ends of each separate extended genetic unit to form separate dual extended genetic units.

Assembly of the dual extended genetic units to form a synthetic genetic construct occurs via homologous recombination directed by the flexible adapter oligonucleotide sequences that are appended to each end of the dual extended units. The flexible adapter oligonucleotides are "flexible" in that they provide the ability to direct random (i.e., shuffled), semi-random, or programmed assembly of the genetic units. FIG. 6B illustrates the programmed assembly of genetic units, where identical flexible adapter oligonucleotides are appended to the ends of genetic units that are to be joined together. In contrast, random assembly is achieved by creating pools of dual extended genetic units sharing the same pair of flanking flexible adapter oligonucleotides which, assuming equivalent recombination efficiencies will form a variety of constructs containing any of the competing dual extended genetic units as illustrated in FIG. 6C. This method allows for the creation of libraries of random clusters. It is also possible to program the position of some dual extended genetic units in a construct, while shuffling others (i.e., semi-random assembly). In addition to directing the position of a genetic unit in a resulting construct, the flexible adapter oligonucleotide sequences can also be used to direct the orientation of the genetic units within a construct as shown in FIG. 12C and described infra.

In accordance with the method of the present invention, the separate genetic units can be assembled together using in vitro (i.e., cell free environment) or in vivo (i.e., within a host cell) homologous recombination.

Methods and protocols for carrying out in vivo homologous recombination are known in the art. Basically, suitable competent host cells (i.e., cells that support homologous recombination) are transformed with the separate dual extended genetic units under conditions suitable for in vivo homologous recombination to occur between identical flexible adapter oligonucleotide portions of the dual extended genetic units thereby assembling the separate genetic units into a synthetic genetic construct (e.g., a linear synthetic genetic construct). In one embodiment of the present invention, the host cells are also transformed with a linearized nucleic acid vector comprising flexible adapter oligonucleotide portions at its terminal or free 3' and 5' ends. In accordance with this embodiment, homologous recombination occurs between identical flexible adapter oligonucleotides of separate dual extended genetic units and identical flexible adapter oligonucleotides of the dual extended genetic units and the linearized vector to form a re-circularized vector comprising the synthetic genetic construct. Any suitable vector (e.g., shuttle vector, plasmid vector, cloning vector, expression vector, etc.) can be used. In vivo methods of recombination that are suitable for use in the present invention include those described in U.S. Pat. Nos. 6,355,412 and 6,509,156 to Stewart et al. Zhang et al., "A New Logic for DNA Engineering using Recombination in *E. coli*," *Nature Genetics* 20:123-128 (1998) and Zhang et al., "DNA Cloning by Homologous Recombination in *E. coli*," *Nature Biotech.* 18:1314-17 (2000), which are hereby incorporated by reference in their entirety.

Suitable hosts for in vivo homologous recombination include prokaryotes such as *Bacillus, E. coli* and other species of Enterobacteriaciae bacteria, *Deinococcus radiodurans, Pseudomonas, Corynebacteria, Lactobacilli, Streptomycedes*, and *Agrobacterium*, eukaryotes such as *Saccharomyces cerevisia* and other yeast, animal cells, synthetic cells, as well as bacteriophages. To minimize background or unwanted recombination in the host, it may be advantageous to mutate or delete genes that are known to perform non-homologous enjoining. For example, in *S. cerevisiae*, Ku, DNA ligase IV, as well as Rad 50, Mre11 and Xrs2 are genes involved in non-homologous recombination. Accordingly, deletion and/or mutation of one or more of these genes in *S. cerevisiae* is advantageous. Suitable host cells also include synthetic cells that have been engineered to carry out homologous recombination with maximal efficiency.

In an in vivo method of the assembly, a mixture of all of the dual extended genetic units to be assembled is used to transfect the host recombination and assembly cell using standard transfection techniques (e.g., microinjection, electroporation, calcium phosphate transfection, or ultra-short pulses (see WO2009/140710 to Zieler et al., which is hereby incorporated by reference)). The ratio of the number of dual extended genetic units in the mixture to the number of cells in the culture to be transfected must be high enough to permit at least some of the cells to take up more genetic units than there are different units in the mixture.

In certain embodiments of the present invention, it may be desirable to include in one or more genetic units to be assembled in vivo, an origin of replication, a centromere, and/or a selectable marker. It is convenient, but not necessary, to include one or more of these elements in a genetic unit of the resulting genetic construct.

The origin of replication may be operable only in the initial, or in an alternate type of cell intended to carry out replication. It may be included in one of the genetic units whose assembly is desired or it may be included on a separate vector fragment included in the assembly. Shuttle vectors may be used permitting, for example, both replication in the initial host and subsequent transfection of assembled sequences in an alternative host, such as *E. coli* or *Bacillus*.

The presence of a centromere is an important element of an artificial chromosome, which can be constructed using the methods of the present invention, because it assures that replicated DNA will be distributed between the mother and daughter cells during replication. In some embodiments, multiple copies of the assembled DNA may be permitted to remain in the same cell and still be recovered effectively. Thus, although the presence of a centromere is preferable, it is not completely necessary. Suitable centromere sequences and their use in constructing artificial chromosomes is described in WO/2009134814 to Zieler et al, which is hereby incorporated by reference in its entirety.

Similarly, the presence of a selectable marker is optional; however, it facilitates recovery of successful transformants in those cells where the DNA has been assembled into a circular pattern. Selectable markers known and used in the art are suitable for use in the methods of the present invention. These selectable markers include, for example and without limitation, antibiotic resistance genes such as ampicillin-resistance genes and kanamycin resistance genes, and selectable markers, such as the HIS3, TRP, and URA3 yeast selectable markers.

Homologous recombination can also be achieved in vitro using cell extracts containing proteins involved in recombination or the purified proteins (i.e., recombinases) themselves. Several proteins or purified extracts having the property of promoting homologous recombination (i.e., having recombinase activity) have been identified in prokaryotes and eukaryotes (see e.g., Cox and Lehman, *Ann. Rev. Biochem.*, 56:229 (1987), Radding et al., *Ann. Rev. Genet.*, 16:405 (1982), Madiraju et al., PNAS USA. 6592 (1988). McCarthy et al., *Proc. Natl. Acad. Sci. USA*, 85: 5854 (1988), and Lopez et al., *Nucleic Acids Res.*, 15:5643 (1987), which are hereby incorporated by reference in their entirety). These general recombinases promote one or more steps in the formation of homologously-paired intermediates, strand-exchange, gene conversion, and/or other steps in the process of homologous recombination. In particular, the frequency of homologous recombination in prokaryotes is significantly enhanced by the presence of recombinase activities. Several purified proteins catalyze homologous pairing and/or strand exchange in vitro, including but not limited to: *E. coli* RecA protein and RecA-like recombinases (see U.S. Patent Application Publication No. 2003/0228608, which is hereby incorporated by reference in its entirety), T4 UvsX protein, Rec1 protein from *Ustilago maydis*, Redβ from lambda bacteriophage (Kowalczykowski et al., *Microbiol. Rev.* 58:40) (1994), which is hereby incorporated by reference in its entirety), RecT from the cryptic Rac prophage of *E. coli* (Kowalczykowski et al., *Microbiol. Rev.* 58:401 (1994), which is hereby incorporated by reference in its entirety), Rad51 protein from *S. cerevisiae* (Sung et al., *Science* 265:1241 (1994), which is hereby incorporated by reference in its entirety), radA from *Archaeoplobus fulgidus* and human cells (McIlwraith et al, *Nucleic Acids Research* 29(22): 4509 (2001) and Baumann et al., *Cell* 87: 757 (1996), which are hereby incorporated by reference in their entirety). Methods of carrying out in vitro homologous recombination reactions are know in the art and are described in, e.g., U.S. Patent Application Publication Nos. 2003/0228608 to Friedman-Ohana and U.S. Pat. No. 7,723,077 to Young et al. and U.S. Pat. No. 7,776,532 to Gibson et al, which are hereby incorporated by reference in their entirety.

In one embodiment of the present invention, the dual extended genetic units are recombinantly assembled to form a linear synthetic genetic construct. In accordance with this embodiment, it is preferable that two of the genetic units, i.e., the genetic units that will comprise the 3' and 5' ends of the linear synthetic genetic construct are provided with telomeres. Using this design approach, the assembled linear synthetic genetic construct contains telomeres on both ends to protect against degradation.

Alternatively, the extended genetic units are assembled in the presence of a linearized nucleic acid vector that comprises flexible adapter oligonucleotide portions at its terminal or free 3' and 5' ends. In accordance with this method, joining the separate dual extended genetic units with the linearized nucleic acid vector. e.g., a DNA vector, forms a re-circularized vector containing the synthetic genetic construct. Suitable nucleic acid vectors include, but are not limited to, plasmid vectors, shuttle vectors, cloning vectors, and expression vectors. The vector can be derived from any organism and may include, for example and without limitation, a bacterial vector, yeast vector, insect vector, mammalian vector, or viral vector. Selection of the appropriate vector may be guided by the origination of the genetic units (i.e., bacterial, yeast, mammalian, viral), the type of homologous recombination reaction (e.g., in vivo vs. in vitro, yeast vs. bacteria), and subsequent use of the synthetic genetic construct. The use of shuttle vectors that replicate in two different host organisms, such as yeast and bacteria as described herein, are particularly useful vectors for the assembly of genetic units in one host cell and subsequent replication, transformation, and expression of the resulting synthetic genetic construct in an alternative host cell. Various shuttle vectors are known in the art and are commercially available. In a preferred embodiment of the present invention, the nucleic acid vector comprises one or more selection markers or selection cassettes as described above that allow for selection and isolation of only recirculated vectors containing the synthetic genetic construct.

Following recombination and assembly, the synthetic genetic construct can be expressed in the host cell of assembly or isolated and transformed into an alternative host cell for expression.

The method of the present invention can be used to join two or more genetic units, for example, 2, 5, 10, 15, 20, 25, 30, 40, 50, 60, 70, 80, 90, 100 genetic units. In one embodiment of the invention, the method of assembly is repeated sequentially to assemble larger and larger synthetic constructs. For example, the method can be carried out to join single genetic units to form small synthetic genetic constructs which are then assembled in a subsequent assembly to form larger synthetic genetic constructs (e.g., a whole genome). The synthetic genetic constructs formed in accordance with the methods of the present invention may be at least about 500 bs, 1 kb, 3 kb, 5 kb, 6 kb, 10 kb, 18 kb, 20 kb, 25 kb, 32 kb, 50 kb, 65 kb, 75 kb, 150 kb, 300 kb, 500 kb, 600 kb, 1 Mb, or larger, for example in the range of 1 Mb to 20 Mb. In one embodiment of the present invention, small genetic units are assembled, through several rounds of assembly, into cassettes of about 6 kb, and then 100 such cassettes are assembled into a synthetic genetic construct of about 600 kb-1 Mb.

The resulting synthetic genetic construct of the present invention may comprise one or more domains within a gene or one or more functional genes, preferably more than one functional gene, a collection of genes that comprises one or more partial or complete biological pathways (e.g., signaling or metabolic pathway), or a partial or complete genome. In one embodiment of the invention the synthetic genetic construct comprises a collection of genetic units encoding domains and/or modules in proteins such as polyketide synthases and non-ribosomal peptide synthetases, which may contain multiple domains and/or modules separated by linker sequences and which synthesize a variety of biological active small molecules. In accordance with this embodiment of the present invention, the dual adapter sequences are designed to encode functional linkers between the domains and modules in the final protein.

Following assembly, the synthetic genetic construct of the present invention is preferably isolated and transformed into a suitable host cell under conditions suitable for expression of the synthetic genetic construct by the host cell. Suitable host cells include any natural cell derived from an animal, plant, archaebacteria, eubacteria, fungi, protest, or synthetic cell.

Another aspect of the present invention relates to a method of DNA barcoding. DNA barcoding is a taxonomic method of identifying a species or strain of an organism using a short genetic sequence located in a standard position in the genome. DNA barcoding is particularly useful in identifying and tracking synthetic genetic constructs, e.g., synthetic genomes, that will create new or modified cells and organisms. In one embodiment of this aspect of the invention, the combinatorial potential of the dual adapter recombination method of the present invention is exploited to generate designed or random barcodes. In this aspect, the bar code itself is composed of a combination of several "genetic units", each one corresponding to an "elementary letter or code building block". Thus, in principle one or several positions (i.e., genetic units) could constitute the code Various alternative embodiments of the methodology of the present invention are envisioned for DNA barcoding. In one embodiment, barcoding is achieved by providing, in addition to the genetic units to be assembled, an artificial genetic unit representing the barcode sequence. This genetic "barcode" unit can essentially be any desired length, e.g., 1-1000 nucleotides in length and will be assembled in a random or programmed location of the genetic construct along with the other genetic units. In an alternative embodiment, the flexible adapter oligonucleotides constitute the "barcode" and the universal adapters, in either an intact or altered form (e.g. truncated or elongated), function to join the flexible adapters (e.g., by overlap extension PCR). This barcode can then be incorporated into a specified position of the genetic construct along with the other dual extended genetic units using in vitro or in vivo homologous recombination.

Another aspect of the present invention relates to a synthetic genetic construct comprising a plurality of assembled separate genetic units. Each separate genetic unit comprises a gene specific portion, a pair of universal adapter oligonucleotides appended to the 5' and 3' ends of the gene specific portion, and a pair of flexible adapter oligonucleotides attached to the 5' and 3' ends of the universal adapter oligonucleotides appended to the gene specific portion. Preferably, the synthetic genetic construct is made in accordance with the methods of the present invention.

The separate genetic units that make up the synthetic genetic construct are described supra, i.e., the genetic units can be artificial or derived from one or more genomic sequences of an animal, plant, archaebacterium, *eubacterium*, fungus, protist, virus, or any combination thereof; the genetic units can comprise one or more functional domains or modules of a gene, one or more genes, etc. In one embodiment of the present invention, the synthetic genetic construct comprises one or more functional domains and/or modules of a gene or genes encoding proteins like polyketide synthases or non-ribosomal peptide synthetases that are comprised of multiple functional domains and/or modules separated by linkers. In accordance with this embodiment, the domains are shuffled or combined to optimize polyketide or non-ribosomal peptide synthesis or to create an artificial multi-domain and/or modular protein with novel biosynthesis abilities. In another embodiment of the present invention, the synthetic genetic construct comprises one or more genes involved in one or more partial or complete biological pathways (e.g., signaling pathways, metabolic, detoxification, or transformation pathways, etc.). In another embodiment of the present invention, the combination of genetic units assembled into a synthetic genetic construct encodes a synthetic, modified, optimized, or artificial biological pathway (i.e., a biological pathway that does not exist in nature). Alternatively, the synthetic genetic construct may contain genetic units encoding a minimal, partial, or complete, wildtype or modified, artificial or optimized, genome (e.g., an animal genome, plant genome, archaebacterial genome, eubacterial viral genome, fungal genome, or any combination thereof).

The present invention also encompasses nucleic acid vectors comprising the synthetic genetic construct of the present invention. Suitable vectors include any vector that capable of transferring or carrying the synthetic genetic construct and/or vectors suitable for expressing the synthetic genetic construct in a host cell. The present invention further encompasses bacteriophages comprising the synthetic genetic construct of the present invention.

The present invention also encompasses host cells transformed with the synthetic genetic construct of the present invention. Suitable host cells are described supra. In accordance with this aspect of the present invention, host cells expressing the synthetic genetic construct may exhibit a modified phenotype. In one embodiment of the present invention, expression of the synthetic genetic construct by the host cell provides a gain-of-function to the host cell. For example, the gain-of-function to the host cell may involve enhanced growth, metabolism, detoxification, or transformation of endogenous or exogenous biological molecules, immunity, pathogen resistance, protein production, small molecule production and other useful phenotypes. The gain-of-function may be an enhancement of a normal cell function or a completely new function (e.g., the synthetic genetic construct encodes a novel metabolic pathway imparting the ability of the cell or organism to metabolize or transform exogenous molecules). A gain-of-function resulting from expression of the synthetic genetic construct by the host cell may also result in the production of a biological product that is exogenous to the host cell. For example, the expression of the synthetic genetic construct may result in the production of one or more exogenous proteins (e.g., therapeutically useful proteins, peptides, or antibodies), a pharmaceutical (e.g., antibiotics), small-molecules, an agricultural chemical, biological energy source, or organic compounds, e.g., polyketides, ribosomal and non-ribosomal peptides (see e.g., "Doekel et al., "Non-ribosomal Peptide Synthetase Module Fusions to Produce Derivatives of Daptomycin in *Streptomyces roseosporus,*" *Microbiol.* 154: 2872-80 (2008), which is hereby incorporated by reference in its entirety), fatty alcohols and fatty alcohol derivatives (see WO2011/019858 to Roessler et al., which is hereby incorporated by reference in its entirety), fatty acids and fatty acid derivatives (see WO/2011/019858 to Roessler et al., which is hereby incorporated by reference in their entirety), branched-chain alcohols (see WO2010/068821 to Roessler et al., which is hereby incorporated by reference in its entirety), and methyl butanol and other compounds from renewable feedstocks (see e.g., WO2009/076480 to Picataggio et al., which is hereby incorporated by reference in its entirety).

In another embodiment of the present invention, the synthetic genetic construct encodes one or more silencing molecules (e.g., microRNA, short hairpin RNA, or RNAi) that are effective for silencing the expression of pathogenic or virulent genes in a bacterium, virus, or other pathogen. In accordance with this embodiment, the host cell gains or loses defense mechanisms against pathogenic invasion.

In another embodiment of the present invention, expression of the synthetic genetic construct by the host cell may result in a loss-of-function to the host cell. For example, expression of a synthetic genetic construct encoding one or more silencing molecules (e.g., one or more RNAi molecules) that are suitable for silencing expression of one or more genes of the host cell.

The present invention further encompasses transgenic organisms, including animals, plants, archaebacteria, eubacteria, fungi, and protists, comprising a host cell expressing a synthetic genetic construct of the present invention.

Another aspect of the present invention relates to a kit for assembling a plurality of genetic units that contains a collection of flexible adapter oligonucleotides.

As described supra, flexible adapter oligonucleotides comprise a universal adapter specific portion and a flexible adapter specific portion. An exemplary collection of flexible adapter oligonucleotides are described herein (see Table 6. SEQ ID NOs:139-158). The flexible adapter specific portions of the oligonucleotides in this collection were derived from a computer generated random 100-kb DNA sequence having 52% GC nucleotide content. The resulting ~35-36 bp oligonucleotides were screened and chosen on the bases of having no predicted secondary structure and not likely to undergo self-annealing, but having homogenous annealing temperatures and GC content. The nucleotide sequences of the flexible adaptor specific portions are shown in Table 1 below as SEQ ID NOs: 1-20.

TABLE 1

Flexible adapter oligonucleotide sequences

| Name | Sequence | SEQ ID NO: |
|---|---|---|
| oSC481 | TACGATGCCAGGATTGTGCGATCTTCACGCTCAGG | 1 |
| oSC482 | TACGATGCCAGGATTGTGCGATCTTCACGCTCAGG | 2 |
| oSC483 | CCTGAGCGTGAAGATCGCACAATCCTGGCATCGTA | 3 |
| oSC484 | CCTGAGCGTGAAGATCGCACAATCCTGGCATCGTA | 4 |
| oSC485 | ACATCTGGCTCACGATATGCCAAACTGCCTCGCCT | 5 |
| oSC486 | ACATCTGGCTCACGATATGCCAAACTGCCTCGCCT | 6 |
| oSC487 | AGGCGAGGCAGTTTGGCATATCGTGAGCCAGATGT | 7 |
| oSC488 | AGGCGAGGCAGTTTGGCATATCGTGAGCCAGATGT | 8 |
| oSC489 | TGGGAAGGGCGATCGGTGCGGGCCTCTTCGCTCTCG | 9 |
| oSC490 | TGGGAAGGGCGATCGGTGCGGGCCTCTTCGCTCTCG | 10 |

TABLE 1-continued

Flexible adapter oligonucleotide sequences

| Name | Sequence | SEQ ID NO: |
|---|---|---|
| oSC491 | ACGTGTCATCGGTTGCGTCATCGGCTGGGAGCATC | 11 |
| oSC492 | ACGTGTCATCGGTTGCGTCATCGGCTGGGAGCATC | 12 |
| oSC531 | GAGTGGACGTTTACAACATCGATCGCCTCGAACCCA | 13 |
| oSC532 | GAGTGGACGTTTACAACATCGATCGCCTCGAACCCA | 14 |
| oSC533 | TGGGTTCGAGGCGATCGATGTTGTAAACGTCCACTC | 15 |
| oSC534 | TGGGTTCGAGGCGATCGATGTTGTAAACGTCCACTC | 16 |
| oSC535 | GCAGTGTTGGAGTTTTGTACCTCCAGTTGCGGCGA | 17 |
| oSC536 | GCAGTGTTGGAGTTTTGTACCTCCAGTTGCGGCGA | 18 |
| oSC537 | TCGCCGCAACTGGAGGTACAAAACTCCAACACTGC | 19 |
| oSC538 | TCGCCGCAACTGGAGGTACAAAACTCCAACACTGC | 20 |

The flexible adapter specific portions of Table 1 can be appended to the universal adaptor oligonucleotides of the present invention (as shown in Table 6) to form a suitable collection of flexible adapter oligonucleotides. Alternatively, the flexible adapter specific portions of Table 1 can be appended to the 5' end of other universal adapter specific sequences or complements thereof that are known in the art.

The kit of the present invention may further include a computer readable storage medium (e.g., a CD or web or internet-based application) that has stored thereon instructions and design parameters for assembling genetic units comprising flexible adapter oligonucleotides. This computer readable storage medium comprises machine executable code which when executed by at least one processor, causes the processor to produce instructions and design parameters for appending flexible adapter oligonucleotides to genetic units having universal adapter oligonucleotides attached thereto, to achieve random, semi-random, or non-random assemble of the genetic units. The instructions and parameters may also aid users design adapters based on properties of their genome of interest and protocol improvements based on multiple user results.

The kit of the present invention may further include one or more sets of universal adapter oligonucleotides. Exemplary universal adapter nucleotide sequences comprises AACAGGGAGAGGGTGGTGGT (SEQ ID NO:21) and (GGTGGTAGCGGTGCGTAAGT (SEQ ID NO: 22). These adapter sequences can be appended to genetic unit specific sequences to facilitate the attachment of the universal adapter oligonucleotides to the genetic units using a DNA polymerase based reaction (e.g., PCR). In accordance with this aspect of the present invention, the kit may also contain components for appending the universal adapter oligonucleotides to genetic units.

The kit of the present invention may further contain reagents suitable for carrying out in vivo and/or in vitro homologous recombination reactions, e.g., appropriate nucleic acid vectors, host cells, recombination enzymes as described supra, etc.

EXAMPLES

The following examples are provided to illustrate embodiments of the present invention but they are by no means intended to limit its scope

Example 1

Bacterial Strains, Culture Conditions, and Virulence Assays

Bacterial strains and plasmids are described in more detail below Mutations and restorations of complementing genes to native loci were performed with the suicide-eviction vector pK18mobsacB and then confirmed by PCR (Wei et al., "A *Pseudomonas syringae* pv. *tomato* DC3000 Mutant Lacking the Type III Effector HopQ1-1 Is Able to Cause Disease in the Model Plant *Nicotiana benthamiana*," *Plant J.* 51:32-46 (2007), which is hereby incorporated by reference in its entirety). Primers for plasmid and mutant construction are given in Table 2. Culture conditions, plant virulence assays, and Cya reporter translocation assays have been previously described (Kvitko et al., "Deletions in the Repertoire of *Pseudomonas syringae* pv. *tomato* DC3000 Type III Secretion Effector Genes Reveal Functional Overlap Among Effectors," *PLoS Pathogens* 5:e1000388 (2009) and Kvitko et al., "Identification of harpins in *Pseudomonas syringae* pv. *Tomato* DC3000, Which Are Functionally Similar to HrpK1 in Promoting Translocation of Type III Secretion System Effectors," *J. Bacteriol.* 189:8059-8072 (2007), which are hereby incorporated by reference in their entirety).

TABLE 2

Primers for Plasmid and Mutant Construction

| Primer Name | 5'->3' Sequence |
|---|---|
| oSC453 | TTAGGTCTTTTTTTATTGTGCGTAACTAACTTGCCCGAGGCCCTTTCGTCTTCAAG (SEQ ID NO: 23) |
| oSC454 | CTCGGTACCCATCGGCATTTTCTTTTGCGTTTTTATTTCTGATTATCAACCGGGGTGG (SEQ ID NO: 24) |
| oSC457 | GGAACAACAGCACACACAGG (SEQ ID NO: 25) |
| oSC458 | CAGCCAAGAGGGAAATAAGG (SEQ ID NO: 26) |
| oSC459 | GATACTGGCTCGGGGTCTG (SEQ ID NO: 27) |
| oSC460 | ACGGCTCTGGATGGTCG (SEQ ID NO: 28) |
| oSC461 | CCGTTTGTTATTGGGCG (SEQ ID NO: 29) |
| oSC462 | AGAGCGATTTGTTGCGA (SEQ ID NO: 30) |
| oSC463 | CAGGCGTATCAATCAACCAG (SEQ ID NO: 31) |
| oSC464 | CGTTATCTTCGTCACCCGAG (SEQ ID NO: 32) |
| oSC467 | TGGGAAGGGCGATCGGTGCGGGCCTCTTCGCTCTCGAGACTAGTAAAGCCTTCGAGCGTCC (SEQ ID NO: 33) |
| oSC468 | ATGCATTCGGATCCATATGTGCTAACAACCATTTTGGAGATTC (SEQ ID NO: 34) |
| oSC469 | ATGGTTGTIAGCACATATGGATCCGAATGCATTGCCAACTGATG (SEQ ID NO: 35) |
| oSC470 | ATTAATGCAGCTGGCACGACAGGTTTCCCGACTACACAGGGATCGAGCAGAACGC (SEQ ID NO: 36) |
| oSC473 | GCTCTAGAGTTCCTTTTTTTATATGCCCAACCAACG (SEQ ID NO: 37) |
| oSC474 | GCTCTAGAGTTAAAACAGCATGAAGCATGCCGGA (SEQ ID NO: 38) |
| P0158 | TGCGGCAGATCAAACCTT (SEQ ID NO: 39) |
| P0242 | CGAACAACACAGAGGCTTGG (SEQ ID NO: 40) |
| P0242 | CGAACAACACAGAGGCTTGG (SEQ ID NO: 41) |
| P0355 | TTCAGCGATGGCAAGATAA (SEQ ID NO: 42) |
| P1296 | CACCATGATGATTCGTAGCCTAAC (SEQ ID NO: 43) |
| P1576 | AGAAAGCTGGGTATCATCGCAAGTGAAAGT (SEQ ID NO: 44) |
| P2203 | CACCATGACCGCACCGATCAAAA (SEQ ID NO: 45) |
| P2257 | ATTAACTAGTGTGTAGGCTGGAGCTGCTTC (SEQ ID NO: 46) |
| P2258 | ATTAACTAGTCATATGAATATCCTCCTTA (SEQ ID NO: 47) |

TABLE 2-continued

Primers for Plasmid and Mutant Construction

| Primer Name | 5'->3' Sequence |
|---|---|
| P2259 | ATTACCCGGGGTGTAGGCTGGAGCTGCTTC (SEQ ID NO: 48) |
| P2260 | ATTACCCGGGCATATGAATATCCTCCTTA (SEQ ID NO: 49) |
| P2366 | ATTAACTAGTAAAATTACGGTGCAGGAGCAGG (SEQ ID NO: 50) |
| P2367 | TAATTCTAGATCAAGCCGAAGACGACAGAC (SEQ ID NO: 51) |
| P2368 | CACCTCTAGATCTATTCCCCGATTGAGCTA (SEQ ID NO: 52) |
| P2369 | TAATACTAGTGGTACCTGGTCAGATTCAGTGC (SEQ ID NO: 53) |
| P2456 | CTGCGAATTCGAGCCCAACG (SEQ ID NO: 54) |
| P2457 | TAATTCTAGAGCTCATCAGCCTGCTCATCAACGGGG (SEQ ID NO: 55) |
| P2458 | TAATTCTAGAAAATGAAAGCAGCGTTCGGCGTAAGTG (SEQ ID NO: 56) |
| P2459 | CGGCGAATTCGAGTTCTGGTTT (SEQ ID NO: 57) |
| P2464 | ATCTCTAGAGTGCGCGGCCAGAGAATATC (SEQ ID NO: 58) |
| P2465 | GCCTCGAATTCTCACACCTTTCCCTATACAC (SEQ ID NO: 59) |
| P2466 | ATAGAATTCCCGCGCTGACAGCTAAAAGCCCAT (SEQ ID NO: 60) |
| P2467 | TAATATCTAGAGGACAGGCCGGACTCGATCT (SEQ ID NO: 61) |
| P2468 | TAATGGATCCTCTGGATGCTGGGTATGT (SEQ ID NO: 62) |
| P2469 | TAATTCTAGACCCCATGACGGTTCTCTCTTT (SEQ ID NO: 63) |
| P2470 | TAATTCTAGACAATAATTCAATAAAGCGCT (SEQ ID NO: 64) |
| P2471 | TAATCTGCAGAAAACTCTACCTCTACG (SEQ ID NO: 65) |
| P2474 | CTAACCAGATGGCTGTATGCATCC (SEQ ID NO: 66) |
| P2475 | CTGGGCTTCGATAAAGCGATTC (SEQ ID NO: 67) |
| P2479 | TAATGAATTCCGGAAATTCGCACCTGATCCAGCAGC (SEQ ID NO: 68) |
| P2480 | TAATTCTAGAATTCATGCTGATTGCACCCCTA (SEQ ID NO: 69) |
| P2481 | TAATTCTAGAGACTGAATCCTAGGCTCTGTACGA (SEQ ID NO: 70) |
| P2482 | TAATGCATGCTCGACCACTTCTCGGTCACGGTCATT (SEQ ID NO: 71) |
| P2485 | GTGTTCTGCGTCATAGCCTTTGTC (SEQ ID NO: 72) |
| P2486 | CGATCCAGITCTCCACAGGCAC (SEQ ID NO: 73) |
| P2494 | TCCTAGAATTCCTTGGTCGAGACCGCCAAGG (SEQ ID NO: 74) |
| P2495 | TAATGAATTCGCAGCGTAGAACGACAAT (SEQ ID NO: 75) |
| P2496 | TAATACTAGTTCCCATTCGTATACCCTCTTTAGT (SEQ ID NO: 76) |
| P2497 | TAATACTAGTCAATGATGTCAAGCCGTGTGTGG (SEQ ID NO: 77) |
| P2501 | CAGCGCCACCTACGATGAGT (SEQ ID NO: 78) |
| P2587 | AACTCACTGAAGCAGCGCCTTG (SEQ ID NO: 79) |
| P2588 | CAGGACTGGGGCTCTGGTTTCA (SEQ ID NO: 80) |
| P2590 | TAATGCTAGCCGGGCAACGCATGCCTTCAATCAGAA (SEQ ID NO: 81) |
| P2591 | TAATCCCGGGATGAGGCTGGTAATAGGGCATGAGTA (SEQ ID NO: 82) |
| P2592 | CTTCCCCGGGAACTGATATCGC (SEQ ID NO: 83) |
| P2593 | GCCTGAATTCACGGCACTGAAT (SEQ ID NO: 84) |
| P2609 | TAATGAATTCTACTGGAGAGGTTGCCACTT (SEQ ID NO: 85) |

TABLE 2-continued

Primers for Plasmid and Mutant Construction

| Primer Name | 5'->3'Sequence |
|---|---|
| P2610 | TAATTCTAGAGACTAAAAAACTCAAATCAGAGTGC (SEQ ID NO: 86) |
| P2611 | TAATTCTAGAGTGCATGTATGCCTCCAGACGT (SEQ ID NO: 87) |
| P2612 | CGGAAAGCTTCAAGCCTTTCTCTTCCAG (SEQ ID NO: 88) |
| P2613 | CCCACCAAGCTGGCTGCATCAT (SEQ ID NO: 89) |
| P2615 | GTCAACGGCCAGGAGCCCTATA (SEQ ID NO: 90) |
| P2616 | CCGCAAGCGTTCAAGGGTCT (SEQ ID NO: 91) |
| P2619 | GCGCTCTGTCGCACTAAAGGCA (SEQ ID NO: 92) |
| P2620 | ATCCTCGCGCGGCATTTGAG (SEQ ID NO: 93) |
| P2625 | GACGGCCCAAAGAGTCGGTGAA (SEQ ID NO: 94) |
| P2626 | AGATCGGCCCGATGATGCTC (SEQ ID NO: 95) |
| P2633 | TAATGGTACCCTGAGTGCGGTGCGGAGCA (SEQ ID NO: 96) |
| P2675 | CCGTTTGTTATTGGGCGCAA (SEQ ID NO: 97) |
| P2676 | GCGTATCAATCAACCAGGGC (SEQ ID NO: 98) |
| P2677 | GCTCGAAGTCAGCGTCAATG (SEQ ID NO: 99) |
| P2678 | CGGTGAAGTCATCCAGCACT (SEQ ID NO: 100) |
| P2679 | AGCGCTGCAGACTGATATGGAC (SEQ ID NO: 101) |
| P2680 | TAATTCTAGATCTCATGATTGAATCTC (SEQ ID NO: 102) |
| P2681 | TAATTCTAGAGTCTGAGCGCTTGAAC (SEQ ID NO: 103) |
| P2682 | TAATGAATTCGGCGTACAGCAGGTCG (SEQ ID NO: 104) |
| P2685 | AAAGGCAGTCGTCGAGCAGA (SEQ ID NO: 105) |
| P2686 | CATGGCGTGATACAAGCGG (SEQ ID NO: 106) |

Example 2

Construction and Usage of the Vectors for Genomic Gene Replacement and Complementation For the construction of the vectors used in this study, the sequences of DNA fragments amplified by PCR and used for cloning were systematically verified to ensure the absence of introduced mutations. Table 3 below summarizes the strains and plasmids used in these Examples.

The $\Delta hrcQ_b$-hrcU deletion construct pCPP6201 was obtained by first amplifying the genomic $\Delta hrcQ_b$-hrcU deletion from CUCPB5113 with P1296/P2203 and cloning the resulting PCR product digested with BsrBI into the SmaI site of pK18mobsacB. The $\Omega$-$Sp^R$ cassette was cloned out of this intermediate construct with an XmnI and EcoRV digest and the FRTGm$^R$ cassette from pCPP5209 (GenBank accession number: EU024549, which is hereby incorporated by reference in its entirety) amplified using P2259/P2260 was inserted as a SmaI fragment. pCPP6201 was used to delete hrcQ$_b$-hrcU from CUCPB5585 and create CUCPB5589.

pCPP5893 was created by PCR amplification of hopI1 flanking regions with P2590/P2591 and P2592/P2593 primer pairs. The PCR fragments were digested with XmaI and ligated with T4 ligase. The ligation product was gel purified, digested with EcoRI and NheI, and cloned into EcoRI and NheI digested pK18mobsacB. pCPP5610 was used to delete hopI1 and create CUCPB5513. The deletion was confirmed by PCR with P2587/P2588.

pCPP5913 was created by PCR amplification of hopB1 flanking regions with P2679/P2680 and P2681/P2682 primer pairs. The PCR fragments were digested with XbaI and ligated with T4 ligase. The ligation product was gel purified, digested with PstI and EcoRI, and cloned into PstI and EcoRI digested pK18mobsacB. pCPP5913 was used to delete hopB1 from CUCPB5560 and create CUCPB5565. The deletion was confirmed by PCR with P2685/P2686.

pCPP5914 was created by PCR amplification of hopAM1-1 flanking regions with P2609/P2610 and P2611/P2612 primer pairs primer pairs. The PCR fragments were digested with XbaI and ligated with T4 ligase. The ligation product was gel purified, digested with EcoRI and HindIII, and cloned into EcoRI and HindIII digested pK18mobsacB. pCPP5914 was used to delete hopAM1-1 and create CUCPB5520. The deletion was confirmed by PCR with P2615/P2616.

pCPP5920 was created by PCR amplification of avrPtoB flanking regions with P2464/P2465 and P2466/P2467 primer pairs. The PCR fragments were digested with EcoRI and ligated with T4 ligase. The ligation product was gel purified, digested with BamHI (using a natural recognition sequence present on the flank) and XbaI, and cloned into BamHI and XbaI digested pK18mobsacB. pCPP5920 was used to delete avrPtoB from CUCPB5534 and create CUCP5537. The deletion was confirmed by PCR with P2677/P2678.

pCPP5923 was created in two steps. First hopAF1 flanking regions were PCR amplified with P2468/P2469 and P2470/P2471 primer pairs. The PCR fragments were digested with XbaI and ligated with T4 ligase. The ligation product was gel purified, digested with PstI and BamHI, and cloned into PstI and BamHI digested pK18mobsacB. The resulting intermediate construct was subsequently digested with XbaI and a SpeI digested FRT Sp/Sm$^R$ cassette amplified from pCPP5242 (GenBank accession number: EUO24551, which is hereby incorporated by reference in its entirety) with P2257/P2258 was inserted. pCPP5923 was used to delete hopAF1 from CUCPB5520. The FRT flanked antibiotic resistance cassettes was removed from the intermediate deletion strains by transformation and curing of the unstable FLP expression vector pCPP5264 (Kvitko et al., "Deletions in the Repertoire of *Pseudomonas syringae* pv. *tomato* DC3000 Type III Secretion Effector Genes Reveal Functional Overlap Among Effectors," *PLoS Pathogens* 5:e1000388 (2009), which is hereby incorporated by reference in its entirety) to create CUCP5534. The deletion was confirmed by PCR with P2474/P2475.

pCPP5934 was created by PCR amplification of hopE1 flanking regions with P2479/P2480 and P2481/P2482 primer pairs. The PCR fragments were digested with XbaI and ligated with T4 ligase. The ligation product was gel purified, digested with SphI and partially digested with EcoRI, and the full length product was cloned into EcoRI and SphI digested pK18mobsacB. pCPP5934 was used to delete hopE1 from CUCPB5565 and create CUCP5571. The deletion was confirmed by PCR with P2485/P2486.

pCPP5952 was created by PCR amplification of avrPto flanking regions with P2495/P2496 and P2497/P2494 primer pairs. The PCR fragments were digested with SpeI and ligated with T4 ligase. The ligation product was gel purified, digested with EcoRI and PstI (using a natural recognition sequence present on the flank), and cloned into EcoRI and PstI digested pK18mobsacB. pCPP5952 was used to delete avrPto from CUCPB5537 and create CUCP5546. The deletion was confirmed by PCR with P2675/P2676.

pCPP5953 was created by PCR amplification of a first hopK1 flanking region with P2369/P2368 which was subsequently digested with SpeI and XbaI and cloned into the NheI site of pK18mobsacB to yield an intermediate construct. The second hopK1 flanking region was amplified with P2367/P2366, digested with XbaI and PstI and cloned into XbaI and PstI digested intermediate construct. pCPP5953 was used to delete hopK1 from CUCPB5546 and create CUCP5560. The deletion was confirmed by PCR with P2619/P2620.

pCPP5919 was created by PCR amplification of hopA1 flanking regions with P2456/P2457 and P2458/P2459 primer pairs. The PCR fragments were digested with XbaI and ligated with T4 ligase. The ligation product was gel purified, digested with EcoRI, and cloned into EcoRI digested pK18mobsacB. pCPP5919 was used to delete hopA1 from CUCPB5571 and create CUCP5573. The deletion was confirmed by PCR with P2462/P2463.

For deletion of hopY1, the hopY1 interruption construct pCPP5983 was created. A FRT Sp/Sm$^R$ cassette was PCR amplified from pCPP5242 with P2259/P2260, digested with SmaI and cloned into FspI digested pCPP3417 (pENTR/D/SD::hopY1 ORF). The resulting vector was digested with EcoRV and NheI and the hopY1::FRTSp/Sm$^R$ region was subcloned into SmaI and XbaI digested pK18mobsacB to obtain pCPP5983. pCPP5983 was used to interrupt hopY1 in CUCPB5573 and create DC3000D28E (CUCP5585). The deletion was confirmed by PCR with P2625/P2626. All 15 previous mutations were re-confirmed to be intact by PCR and no inversions between FRT sites could be detected.

pCPP6214, the native avrPto gene restoration construct was built by amplifying an avrPto PCR product encompassing the deleted region and extending within the recombination flanks of pCPP5952 deletion construct from DC3000 genomic DNA. This fragment was digested with AgeI and XbaI and cloned in pCPP5952 digested with AgeI and XbaI to recreate a wild type avrPto locus with bordering regions for recombination. pCPP6214-mediated restoration in *P. syringae* strains was systematically confirmed on both sides by colony PCR with primers pairs oSC461/oSC462 and oSC463/oSC464 designed to anneal on the restored region and a sequence bordering the locus but external to the neighboring recombination flank.

Similarly, pCPP6215 the native avrPtoB gene restoration construct was built by cloning a DraIII and EcoNI digested PCR product of the wild type avrPtoB locus in the pCPP5920 deletion construct digested with DraIII and EcoNI. avrPtoB locus restoration was colony PCR verified with oSC458/oSC457 and oSC460/oSC459.

pCPP6216, the CEL/clusterVI genomic restoration construe was obtained by digesting pCPP3139, which contains the DC3000 genomic region covering the CEL, hrp and EEL clusters, with XbaI and SpeI to release a sub-genomic fragment covering the entire CEL and flanking sequences for recombination. The digestion products were gel purified and cloned into XbaI digested pK18mobsacB. Identity of the insert was verified by three digests with different enzymes. CEL/clusterVI genomic restoration was confirmed by colony PCR with P0242/P0158 and P1576/P0355.

pCPP6217, the shcM-hopM1 genomic restoration construct was obtained by cloning a PCR product encompassing the promoter and 3'-end sequence of the operon amplified from DC3000 genomic DNA with oSC473/oSC474 and digested with XbaI in the CEL deletion construct pCPP5734 digested with SpeI. In this vector the shcM-hopM1 operon is oriented opposite to the hrpH gene. shcM-hopM1 genomic restoration was confirmed by colony PCR with P2613/P2501 and P2633/P0242.

pCPP6218 was assembled in yeast by homologous recombination between a KpnI digested pK18mobsacB and a pool of PCR products composed of: (i) an amplicon encompassing the yeast 2μ a origin of replication and the TRP1 selectable marker gene from the pYESTrp2 (Invitrogen) plasmid amplified with oSC453 and oSC454 that replaced the sacB gene, (ii) the CYH2 counter selectable marker gene amplified from pDEST32 (Invitrogen) with oSC467 and oSC468 and (iii) the EEL homologous recombination region spanning the PSPTO_1409 CDS and amplified from DC3000 genomic DNA with primers oSC469 and oSC470. The CYH2 and PSPTO_1409 regions in pCPP6218 were sequence verified. The empty shuttle vector pCPP6219 was obtained by removing the CYH2 cassette of pCPP6218 by digestion with XhoI and BamHI followed by T4 polymerase filling and self-ligation.

TABLE 3

Strains and Plasmids Used in Examples

| Designation | Genotype | Relevant Features | Source |
|---|---|---|---|
| *Pseudomonas syringae* STRAINS | | | |
| DC3000 | Wild type *P. syringae* pv. tomato strain DC3000 | Rf$^R$, Ap$^R$ | Buell et al., PNAS 100: 10181-10186 (2003) |
| CUCPB5113 | ΔhrcQ$_B$-hrcU::ΩSpR | T3SS$^-$, Sp$^R$ | Badel et al., Mol. Plant Microbe Interact. 19: 99-111 (2006) |
| CUCPB5440 | ΔhopD1-hopR1::FRT | ΔIV | Wei et al., Plant J. 51: 32-46 (2007) |
| CUCPB5459 | ΔhopU1-hopF2 ΔhopC1-hopH1::FRT ΔhopD1-hopR1::FRT ΔhopAA1-2-hopG1::FRT pDC3000A$^-$ pDC3000B$^-$ | ΔIΔIIΔIVΔIXΔX | Wei et al., Plant J. 51: 32-46 (2007) |
| CUCPB5460 | ΔhopQ1-1 | ΔQ | Wei et al., Plant J. 51: 32-46 (2007) |
| CUCPB5500 | ΔhopU1-hopF2 ΔhopC1-hopH1::FRT ΔhopD1-hopR1::FRT ΔavrE-shcN ΔhopAA1-2-hopG1::FRT pDC3000A$^-$ pDC3000B$^-$ | ΔIΔIIΔIVΔCELΔIXΔX | Kvitko et al., PLoS Pathogens 5: e1000388 (2009) |
| CUCPB5513 | ΔhopU1-hopF2 ΔhopC1-hopH1::FRT ΔhopD1-hopR1::FRT ΔavrE-shcN ΔhopAA1-2-hopG1::FRT ΔhopI1 pDC3000A$^-$ pDC3000B$^-$ | ΔIΔIIΔIVΔCELΔIXΔXΔII | This study |
| CUCPB5515 | ΔhopD1-hopR1::FRT ΔavrE-shcN | ΔIVΔCEL | Kvitko et al., PLoS Pathogens 5: e1000388 (2009) |
| CUCPB5520 | ΔhopU1-hopF2 ΔhopC1-hopH1::FRT ΔhopD1-hopR1::FRT ΔavrE-shcN ΔhopAA1-2-hopG1::FRT ΔhopI1 ΔhopAM1-1 pDC3000A$^-$ pDC3000B$^-$ | ΔIΔIIΔIVΔCELΔIXΔXΔI1ΔAM1-1 | This study |
| CUCPB5534 | ΔhopU1-hopF2 ΔhopC1-hopH1::FRT ΔhopD1-hopR1::FRT ΔavrE-shcN ΔhopAA1-2-hopG1::FRT ΔhopI1 ΔhopAM1-1 ΔhopAF1:FRT pDC3000A$^-$ pDC3000B$^-$ | ΔIΔIIΔIVΔCELΔIXΔXΔI1ΔAM1-1ΔAF1 | This study |
| CUCPB5537 | ΔhopU1-hopF2 ΔhopC1-hopH1::FRT ΔhopD1-hopR1::FRT ΔavrE-shcN ΔhopAA1-2-hopG1::FRT ΔhopI1 ΔhopAM1-1 ΔhopAF1:FRT ΔavrPtoB pDC3000A$^-$ pDC3000B$^-$ | ΔIΔIIΔIVΔCELΔIXΔXΔI1ΔAM1-1ΔAF1ΔPtoB | This study |
| CUCPB5546 | ΔhopU1-hopF2 ΔhopC1-hopH1::FRT ΔhopD1-hopR1::FRT ΔavrE-shcN ΔhopAA1-2-hopG1::FRT ΔhopI1 ΔhopAM1-1 ΔhopAF1:FRT ΔavrPtoB ΔavrPto pDC3000A$^-$ pDC3000B$^-$ | ΔIΔIIΔIVΔCELΔIXΔXΔI1ΔAM1-1ΔAF1ΔPtoBΔPto | This study |
| CUCPB5560 | ΔhopU1-hopF2 ΔhopC1-hopH1::FRT ΔhopD1-hopR1::FRT ΔavrE-shcN ΔhopAA1-2-hopG1::FRT ΔhopI1 ΔhopAM1-1 ΔhopAF1::FRT ΔavrPtoB ΔavrPto ΔhopK1 pDC3000A$^-$ pDC3000B$^-$ | ΔIΔIIΔIVΔCELΔIXΔXΔI1ΔAM1-1ΔAF1ΔPtoBΔPtoΔK1 | This study |
| CUCPB5565 | ΔhopU1-hopF2 ΔhopC1-hopH1::FRT ΔhopD1-hopR1::FRT ΔavrE-shcN ΔhopAA1-2-hopG1::FRT ΔhopI1 ΔhopAM1-1 ΔhopAF1:FRT ΔavrPtoB ΔavrPto ΔhopK1 ΔhopB1 pDC3000A$^-$ pDC3000B$^-$ | ΔIΔIIΔIVΔCELΔIXΔXΔI1ΔAM1-1ΔAF1ΔPtoBΔPtoΔK1ΔB1 | This study |
| CUCPB5571 | ΔhopU1-hopF2 ΔhopC1-hopH1::FRT ΔhopD1-hopR1::FRT ΔavrE-shcN ΔhopAA1-2-hopG1::FRT ΔhopI1 ΔhopAM1-1 ΔhopAF1:FRT ΔavrPtoB ΔavrPto ΔhopK1 ΔhopB1 ΔhopE1 pDC3000A$^-$ pDC3000B$^-$ | ΔIΔIIΔIVΔCELΔIXΔXΔI1ΔAM1 1ΔAF1ΔPtoBΔPtoΔK1ΔB1ΔE1 | This study |
| CUCPB5573 | ΔhopU1-hopF2 ΔhopC1-hopH1::FRT ΔhopD1-hopR1::FRT ΔavrE-shcN ΔhopAA1-2-hopG1::FRT ΔhopI1 ΔhopAM1-1 ΔhopAF1:FRT ΔavrPtoB ΔavrPto ΔhopK1 ΔhopB1 ΔhopE1 ΔhopA1::FRT pDC3000A$^-$ pDC3000B$^-$ | ΔIΔIIΔIVΔCELΔIXΔXΔI1ΔAM1-1ΔAF1ΔPtoBΔPtoΔK1ΔB1ΔE1ΔA1 | This study |
| CUCPB5585 | ΔhopU1-hopF2 ΔhopC1-hopH1::FRT ΔhopD1-hopR1::FRT ΔavrE-shcN ΔhopAA1-2-hopG1::FRT ΔhopI1 ΔhopAM1-1 ΔhopAF1::FRT ΔavrPtoB ΔavrPto ΔhopK1 ΔhopB1 ΔhopE1 ΔhopA1::FRT hopY1:FRTSpR pDC3000A$^-$ pDC3000B$^-$ | DC3000D28E: ΔIΔIIΔIVΔCELΔIXΔXΔI1ΔAM1-1ΔAF1ΔPtoBΔPtoΔK1ΔB1ΔE1ΔA1Y1::Sp$^R$ | This study |

TABLE 3-continued

Strains and Plasmids Used in Examples

| Designation | Genotype | Relevant Features | Source |
|---|---|---|---|
| CUCPB5589 | ΔhopU1-hopF2 ΔhopC1-hopH1::FRT ΔhopD1-hopR1::FRT ΔavrE-shcN ΔhopAA1-2-hopG1::FRT ΔhopI1 ΔhopAM1-1 ΔhopAF1::FRT ΔavrPtoB ΔavrPto ΔhopK1 ΔhopB1 ΔhopE1 ΔhopA1:FRT hopY1::FRTSpR ΔhrcQ$_{B-}$hrcU::FRTGmR pDC3000A$^-$ pDC3000B$^-$ | T3SS$^-$ DC3000D28E, Sp$^R$, Gm$^R$ | This study |
| CUCPB6011 | ΔhopU1-hopF2 ΔhopC1-hopH1::FRT ΔhopD1-hopR1::FRT ΔavrE-shcN ΔhopAA1-2-hopG1::FRT ΔhopI1 ΔhopAM1-1 ΔhopAF1::FRT ΔavrPtoB ΔhopK1 ΔhopB1 ΔhopE1 ΔhopA1::FRT hopY1::FRTSpR pDC3000A$^-$ PDC3000B$^-$ | DC3000D28E+Pto, Sp$^R$ | This study |
| CUCPB6012 | ΔhopU1-hopF2 ΔhopC1-hopH1::FRT ΔhopD1-hopR1::FRT ΔavrE-shcN ΔhopAA1-2-hopG1::FRT ΔhopI1 ΔhopAM1-1 ΔhopAF1:FRT ΔavrPto ΔhopK1 ΔhopB1 ΔhopE1 ΔhopA1::FRT hopY1::FRTSpR pDC3000A$^-$ PDC3000B$^-$ | DC3000D28E+PtoB, Sp$^R$ | This study |
| CUCPB6013 | ΔhopU1-hopF2 ΔhopC1-hopH1::FRT ΔhopD1-hopR1::FRT ΔavrE-shcN ΔhopAA1-2-hopG1::FRT ΔhopI1 ΔhopAM1-1 ΔhopAF1::FRT ΔhopK1 ΔhopB1 ΔhopE1 ΔhopA1::FRT hopY1::FRTSpR pDC3000A$^-$ pDC3000B$^-$ | DC3000D28E+Pto+PtoB, Sp$^R$ | This study |
| CUCPB6014 | ΔhopU1-hopF2 ΔhopC1-hopH1::FRT ΔhopD1-hopR1::FRT ΔavrE-shcN::shcM-hopM1 ΔhopAA1-2-hopG1::FRT ΔhopI1 ΔhopAM1-1 ΔhopAF1::FRT ΔavrPtoB ΔavrPto ΔhopK1 ΔhopB1 ΔhopE1 ΔhopA1::FRT hopY1:FRTSpR pDC3000A$^-$ pDC3000B$^-$ | DC3000D28E+M1, Sp$^R$ | This study |
| CUCPB6015 | ΔhopU1-hopF2 ΔhopC1-hopH1::FRT ΔhopD1-hopR1::FRT ΔhopAA1-2-hopG1::FRT ΔhopI1 ΔhopAM1-1 ΔhopAF1::FRT ΔavrPtoB ΔavrPto ΔhopK1 ΔhopB1 ΔhopE1 ΔhopA1::FRT hopY1::FRTSpR pDC3000A$^-$ pDC3000B$^-$ | DC3000D28E+CEL, Sp$^R$ | This study |
| CUCPB6016 | ΔhopU1-hopF2 ΔhopC1-hopH1::FRT ΔhopD1-hopR1::FRT ΔavrE-shcN::shcM-hopM1 ΔhopAA1-2-hopG1::FRT ΔhopI1 ΔhopAM1-1 ΔhopAF1::FRT ΔavrPtoB ΔhopK1 ΔhopB1 ΔhopE1 ΔhopA1::FRT hopY1::FRTSpR pDC3000A$^-$ pDC3000B$^-$ | DC3000D28E+M1+Pto, Sp$^R$ | This study |
| CUCPB6017 | ΔhopU1-hopF2 ΔhopC1-hopH1::FRT ΔhopD1-hopR1::FRT ΔavrE-shcN::shcM-hopM1 ΔhopAA1-2-hopG1::FRT ΔhopI1 ΔhopAM1-1 ΔhopAF1::FRT ΔavrPto ΔhopK1 ΔhopB1 ΔhopE1 ΔhopA1::FRT hopY1::FRTSpR PDC3000B$^-$ | DC3000 D28E+M1+Pt B, Sp$^R$ | This study |
| CUCPB6018 | ΔhopU1-hopF2 ΔhopC1-hopH1::FRT ΔhopD1-hopR1::FRT ΔhopAA1-2-hopG1::FRT ΔhopI1 ΔhopAM1-1 ΔhopAF1::FRT ΔavrPtoB ΔhopK1 ΔhopB1 ΔhopE1 ΔhopA1::FRT hopY1::FRTSpR pDC3000A$^-$ pDC3000B$^-$ | DC3000D28E+CEL+Pto, Sp$^R$ | This study |
| CUCPB6019 | ΔhopU1-hopF2 ΔhopC1-hopH1::FRT ΔhopD1-hopR1::FRT ΔhopAA1-2-hopG1::FRT ΔhopI1 ΔhopAM1-1 ΔhopAF1::FRT ΔavrPto ΔhopK1 ΔhopB1 ΔhopE1 ΔhopA1::FRT hopY1::FRTSpR pDC3000A$^-$ pDC3000B$^-$ | DC3000D28E+CEL+PtoB, Sp$^R$ | This study |
| CUCPB6020 | ΔhopU1-hopF2 ΔhopC1-hopH1::FRT ΔhopD1-hopR1::FRT ΔavrE-shcN::shcM-hopM1 ΔhopAA1-2-hopG1::FRT ΔhopI1 ΔhopAM1-1 ΔhopAF1::FRT ΔhopK1 ΔhopB1 ΔhopE1 ΔhopA1::FRTSpR pDC3000A$^-$ pDC3000B$^-$ | DC3000D28E+M1+Pto+PtoB, Sp$^R$ | This study |
| CUCPB6021 | ΔhopU1-hopF2 ΔhopC1-hopH1::FRT ΔhopD1-hopR1::FRT ΔhopAA1-2-hopG1::FRT ΔhopI1 ΔhopAM1-1 ΔhopAF1::FRT ΔhopK1 ΔhopB1 ΔhopE1 ΔhopA1:FRT hopY1::FRTSpR pDC3000A$^-$ pDC3000B$^-$ | DC3000D28E+CEL+Pto+PtoB, Sp$^R$ | This study |
| CUCPB6022 | ΔhopU1-hopF2 ΔhopC1-hopH1::FRT ΔhopD1-hopR1::FRT ΔavrE-shcN::shcM-hopM1 EEL::[pCPP6219] ΔhopAA1-2-hopG1::FRT ΔhopI1 ΔhopAM1-1 ΔhopAF1::FRT ΔavrPtoB ΔhopK1 ΔhopB1 ΔhopE1 ΔhopA1::FRT hopY1::FRTSpR pDC3000A$^-$ pDC3000B$^-$ | DC3000D28E+M1+Pto+EEL (Ø), Sp$^R$, Km$^R$ | This study |
| CUCPB6023 | ΔhopD1-hopR1::FRT ΔavrE-shcN EEL::[pCPP6219] | ΔIVΔCEL+EEL(Ø), Sp$^R$, Km$^R$ | This study |
| CUCPB6024 | ΔhopD1-hopR1::FRT ΔavrE-shcN EEL::[pCPP6219 shcM-hopM1] | ΔIVΔCEL+EEL(M1), Sp$^R$, Km$^R$ | This study |
| CUCPB6025 | ΔhopU1-hopF2 ΔhopC1-hopH1::FRT ΔhopD1-hopR1::FRT ΔavrE-shcN EEL::[pCPP6219] ΔhopAA1-2-hopG1::FRT ΔhopI1 ΔhopAM1-1 ΔhopAF1::FRT ΔavrPtoB ΔavrPto ΔhopK1 ΔhopB1 ΔhopE1 ΔhopA1::FRT hopY1:FRTSpR pDC3000A$^-$ pDC3000B$^-$ | DC3000D28E+EEL(Ø), Sp$^R$, Km$^R$ | This study |
| CUCPB6026 | ΔhopU1-hopF2 ΔhopC1-hopH1::FRT ΔhopD1-hopR1::FRT ΔavrE-shcN EEL::[pCPP6219 avrPtoB] ΔhopAA1-2-hopG1::FRT ΔhopI1 ΔhopAM1-1 ΔhopAF1::FRT ΔavrPtoB ΔavrPto ΔhopK1 ΔhopB1 ΔhopE1 ΔhopA1::FRT hopY1::FRTSpR pDC3000A$^-$ pDC3000B$^-$ | DC3000D28E+EEL(PtoB), Sp$^R$, Km$^R$ | This study |

TABLE 3-continued

Strains and Plasmids Used in Examples

| Designation | Genotype | Relevant Features | Source |
|---|---|---|---|
| CUCPB6027 | ΔhopU1-hopF2 ΔhopC1-hopH1::FRT ΔhopD1-hopR1::FRT ΔavrE-shcN EEL::[pCPP6219 avrPtoB shcM-hopM1] ΔhopAA1-2-hopG1::FRT ΔhopI1 ΔhopAM1-1 ΔhopAF1::FRT ΔavrPtoB ΔavrPto ΔhopK1 ΔhopB1 ΔhopE1 ΔhopA1::FRT hopY1::FRTSpR pDC3000A⁻ pDC3000B⁻ | DC3000D28E+EEL(PtoB+M1), Sp$^R$, Km$^R$ | This study |
| CUCPB6028 | ΔhopU1-hopF2 ΔhopC1-hopH1::FRT ΔhopD1-hopR1::FRT ΔavrE-shcN::shcM-hopM1 EEL::[pCPP6219 hopE1] ΔhopAA1-2-hopG1::FRT ΔhopI1 ΔhopAM1-1 ΔhopAF1::FRT ΔavrPto ΔhopK1 ΔhopB1 ΔhopE1 ΔhopA1::FRT hopY1::FRTSpR pDC3000A⁻ pDC3000B⁻ | DC3000D28E+M1+PtoB+EEL (E1), Sp$^R$, Km$^R$ | This study |
| CUCPB6029 | ΔhopU1-hopF2 ΔhopC1-hopH1::FRT ΔhopD1-hopR1::FRT ΔavrE-shcN::shcM-hopM1 EEL::[pCPP6219 hopE1] hopAM1-1] ΔhopAA1-2-hopG1::FRT ΔhopI1 ΔhopAM1-1 ΔhopAF1::FRT ΔavrPto ΔhopK1 ΔhopB1 ΔhopE1 ΔhopA1::FRT hopY1::FRTSpR pDC3000A⁻ pDC3000B⁻ | DC3000D28E+M1-PtoB+EEL (E1+AM1-1), Sp$^R$, Km$^R$ | This study |
| CUCPB6030 | ΔhopU1-hopF2 ΔhopC1-hopH1::FRT ΔhopD1-hopR1::FRT ΔavrE-shcN::shcM-hopM1 EEL::[pCPP6219 hopE1 hopG1] ΔhopAA1-2-hopG1::FRT ΔhopI1 ΔhopAM1-1 ΔhopAF1::FRT ΔavrPto ΔhopK1 ΔhopB1 ΔhopE1 ΔhopA1::FRT hopY1::FRTSpR pDC3000A⁻ pDC3000B3⁻ | DC3000D28E+M1+PtoB+EEL (E1+G1), Sp$^R$, Km$^R$ | This study |
| CUCPB6031 | ΔhopU1-hopF2 ΔhopC1-hopH1::FRT ΔhopD1-hopR1::FRT ΔavrE-shcN::shcM-hopM1 EEL::[pCPP62I9 hopE1 hopAM1-1 hopG1] ΔhopAA1-2-hopG1::FRT ΔhopI1 ΔhopAM1-1 ΔhopAF1::FRT ΔavrPto ΔhopK1 ΔhopB1 ΔhopE1 ΔhopA1::FRT hop Y1::FRTSpR pDC3000A⁻ pDC3000B⁻ | DC3000D28E+M1+PtoB+EEL (E1+G1+AM1-1), Sp$^R$, Km$^R$ | This study |
| CUCPB6032 | ΔhopU1-hopF2 ΔhopC1-hopH1::FRT ΔhopD1-hopR1::FRT EEL::[pCPP6219 hopAM1-1 hopE1 hopG1] ΔhopAA1-2-hopG1::FRT ΔhopI1 ΔhopAM1-1 ΔhopAF1::FRT ΔavrPto ΔhopK1 ΔhopB1 ΔhopE1 ΔhopA1::FRT hopY1::FRTSpR pDC3000A⁻ pDC3000B⁻ | DC3000D28E+CEL+PtoB+EEL (E1+G1+AM1-1), Sp$^R$, Km$^R$ | This study |

PLASMIDS

| Designation | Genotype | Relevant Features | Source |
|---|---|---|---|
| pK18mobsacB | pMB1 mob nptII sacB | Suc$^S$, Km$^R$ | Schafer et al., Gene 145: 69-73 (1994) |
| pCPP5702 | pUCP26::ΩKm P$_{avrpto}$ avrPto-cya | Gm$^R$ Km$^R$ | Kvitko et al., J. Bacteriol. 189: 8059-72 (2007) |
| pCPP5893 | pK18mobsacB::ΔhopI1 | Suc$^S$, Km$^R$ | This study |
| pCPP5913 | pK18mobsacB::ΔhopB1 | Suc$^S$, Km$^R$ | This study |
| pCPP5914 | pK18mobsacB::ΔhopAM1-1 | Suc$^S$, Km$^R$ | This study |
| pCPP5919 | pK18mobsacB::ΔhopA1 | Suc$^S$, Km$^R$ | This study |
| pCPP5920 | pK18mobsacB::ΔavrPtoB | Suc$^S$, Km$^R$ | This study |
| pCPP5923 | pK18mobsacB::ΔhopAF1::FRTSp$^R$ | Suc$^S$, Km$^R$, Sp$^R$ | This study |
| pCPP5934 | pK18mobsacB::ΔhopE1 | Suc$^S$, Km$^R$ | This study |
| pCPP5952 | pK18mobsacB::ΔavrPto | Suc$^S$, Km$^R$ | This study |
| pCPP5953 | pK18mobsacB::ΔhopK1 | Suc$^S$, Km$^R$ | This study |
| pCPP5983 | pK18mobsacB::hopY1::FRTSp$^R$ | Suc$^S$, Km$^R$, Sp$^R$ | This study |
| pCPP6201 | pK18mobsacB::ΔhrcQ$_b$-hrcU | Suc$^S$, Km$^R$, Gm$^R$ | This study |
| pCPP6214 | pK18mobsacB::avrPto | Suc$^S$, Km$^R$ | This study |
| pCPP6215 | pK18mobsacB::avrPtoB | Suc$^S$, Km$^R$ | This study |
| pCPP6216 | pK18mobsacB::CEL | Suc$^S$, Km$^R$ | This study |
| pCPP6217 | pK18mobsacB::shcM hopM1 | Suc$^S$, Km$^R$ | This study |
| pCPP6218 | pMB1 mob nptII PSPTO_1409 2μORI TRP2 CYH2(Cycloheximide$^S$) | PRIVAS shuttle vector | This study |
| pCPP6219 | pMB1 mob nptII PSPTO_1409 2μORI TRP2 | Empty PRIVAS shuttle vector | This study |

All references cited in Table 3 are hereby incorporated by reference in their entirety.

Example 3

Conception and Experimental Design of the Dual Adapter Recombination and Programmable or Random In Vivo Assembly Shuttle (PRIVAS) System Overview of the Use of Flexible, Dual Adapters, which are Central to the PRIVAS System.

PRIVAS exploits the ability of short, terminal adapters to direct recombination of unrelated DNA fragments in vivo or in vitro. The novel principle of the method is to use a system of dual adapters enabling each unique DNA fragment in a set of interest to be flanked by a pair of hybrid universal-flexible adapters. Universal adapters (UAs) are first attached to the DNA fragments by PCR or other suitable method, such that all fragments in the set are flanked on one end by UA1 and the other by UA2. The flexible adapters (FAs) carry homology to UA1 or UA2, and they also carry unique sequences designed to support recombination among themselves and/or with vectors carrying recombination sites for FA1 and FAn (in a set involving FA1, FA2 . . . FAn). Because the DNA fragments of interest have been universalized with UA1 and UA2 and because FAs from a separately maintained panel of oligonucleotides can be easily attached by PCR, a small number of starting reagents (the set of universalized DNA fragments and the set of FA oligonucleotides) can be used to generate infinitely complex random or programmed arrangements of concatenated products using any of a variety of recombination methods. These recombination methods could involve, for example, recombinases functioning in vivo or restriction enzymes functioning in vitro (Raymond et al., "General Method for Plasmid Construction Using Homologous Recombination," *Biotechniques* 26:134-8, 140-1 (1999); Li and Elledge, "Harnessing Homologous Recombination in vitro to Generate Recombinant DNA Via SLIC," *Nat. Methods* 4:251-6 (2007); Engler et al., "Golden Gate Shuffling: A One-Pot DNA Shuffling Method Based on Type IIs Restriction Enzymes," *PLoS One* 4:e5553 (2009); and Sleight et al., "In-Fusion BioBrick Assembly and Re-Engineering," *Nucleic Acids Res.* 38:2624-36 (2010), which are hereby incorporated by reference in their entirety). Dual adapter recombination is used here to support concatenation of T3E genes via recombination in yeast as a key component of the PRIVAS system.

Outline of the PRIVAS System.

Dual adapter recombination and PRIVAS are a solution to the need for versatile multi-gene complementation in various *P. syringae* pv. *tomato* DC3000 polymutant backgrounds and for potentially a wide variety of other uses with complex biological systems. It enables the assembly of engineered artificial genetic islands containing several (1 to 5 as shown herein, but between 10-20 genetic units or more can be assembled) genes or Genetic Units (GU). The configuration of the islands or clusters can be randomly or fully specified before construction. For its implementation, the system exploits homologous recombination through short (~35 bp) artificial flexible adapters (FA). In this version of the system yeast was used to perform the recombination reactions for the custom assembly of several DNA fragments. The first step of the procedure involves PCR amplification of DNA regions of interest using oligonucleotide primers that are chimeric in that their 3' end carries GU-specific homology and their 5' end carries a short (18-20 bp) universal adapter region (UA). In this work a total of 16 GUs from the DC3000 genome were amplified. The sequences of the gene specific primers used are provided in Table 4 below. Graphical representations of the corresponding regions in their genomic context are available in FIG. 10.

TABLE 4

Gene Specific Primers Containing Universal Adapter Oligonucleotide Sequences

| GU label | Genbank accession number of the template molecule | Coordinates of the amplified fragments on the template | | Size of amplified genomic region (bp) | Sense primer sequence | Antisense primer sequence |
|---|---|---|---|---|---|---|
| hopA1 | NC_004578 | 6085532 | 6087577 | 2090 | aacagggagagggtggtggtCGGACAGGTCA TCGTGCAG (SEQ ID NO: 107) | ggtggtagcggtgcgtaagtCGAGCG GTTCTGTTTAGCCTT (SEQ ID NO: 108) |
| hopAF1 | NC_004578 | 1730162 | 1731665 | 1540 | aacagggagagggtggtggtTGCAGTATGTA GGCTTTTTGGAGACGA (SEQ ID NO: 109) | ggtggtagcggtgcgtaagtTCGGGG CGTTTGCTTGGGCCTT (SEQ ID NO: 110) |
| hopAM1-1 | NC_004578 | 1115371 | 1116506 | 1160 | aacagggagagggtggtggtCGATGGCGGCG TTTATGTGGA (SEQ ID NO: 111) | ggtggtagcggtgcgtaagtGCGGGC TATTGTTGAAGGTGA (SEQ ID NO: 112) |
| hopAO1 | NC_004578 | 5345062 | 5348677 | 3660 | aacagggagagggtggtggtGCCTTGTGGCG GGCTTGGTGGT (SEQ ID NO: 113) | ggtggtagcggtgcgtaagtTCAGAC CCTCCCTATACATTTACTTTC TATCC (SEQ ID NO: 114) |
| vhopC1 | NC_004578 | 648655 | 649879 | 1270 | aacagggagagggtggtggtGCTTTGCCGTC TTGGCCTACTGA (SEQ ID NO: 115) | ggtggtagcggtgcgtaagtTCCGAT CTCAGGCGATGCAATCCT (SEQ ID NO: 116) |
| hopE1 | NC_004578 | 4880997 | 4881927 | 950 | aacagggagagggtggtggtGCAACCTGCTT TCATTCCGCT (SEQ ID NO: 117) | ggtggtagcggtgcgtaagtCGCTCG GTGATGCTGCGTT (SEQ ID NO: 118) |
| hopF2 | NC_004578 | 548241 | 550769 | 2580 | aacagggagagggtggtggtGCCCCTTCGTT ACCTTCCAGCGT (SEQ ID NO: 119) | ggtggtagcggtgcgtaagtGGATGC GTTTTGGCGGATGAC (SEQ ID NO: 120) |
| hopG1 | NC_004578 | 5353481 | 5355333 | 1870 | aacagggagagggtggtggtACCGTCCAGAG CGTCGGCAA (SEQ ID NO: 121) | ggtggtagcggtgcgtaagtACGAGG AGCGGCCAAGCGGGTA (SEQ ID NO: 122) |
| hopH1 | NC_004578 | 647504 | 648619 | 1130 | aacagggagagggtggtggtCCTCGCGTTTT GCGATAGTGA (SEQ ID NO: 123) | ggtggtagcggtgcgtaagtCGGCGT TTGTCTTAATTCCTTC (SEQ ID NO: 124) |
| hopI1 | NC_004578 | 5416567 | 5418354 | 1800 | aacagggagagggtggtggtAGGCTGAAGAT TTGTGACGCAGAG (SEQ ID NO: 125) | ggtggtagcggtgcgtaagtACGCAT TTTTCCGAGGCAGTGGA (SEQ ID NO: 126) |

TABLE 4-continued

Gene Specific Primers Containing Universal Adapter Oligonucleotide Sequences

| GU label | Genbank accession number of the template molecule | Coordinates of the amplified fragments on the template | | Size of amplified genomic region (bp) | Sense primer sequence | Antisense primer sequence |
|---|---|---|---|---|---|---|
| hopK1 | NC_004578 | 60025 | 61636 | 1630 | aacagggagagggtggtggtCGCATAAGTGGCAATCGGT (SEQ ID NO: 127) | ggtggtagcggtgcgtaagtTCAATCGTACCTGCCTGTGG (SEQ ID NO: 128) |
| hopM1 | NC_004578 | 1510850 | 1513658 | 2808 | aacagggagagggtggtggtAGTTCCTTTTTTTATATGCCCAACCAACG (SEQ ID NO: 129) | ggtggtagcggtgcgtaagtTAAAACAGCATGAAGCATGCCGGA (SEQ ID NO: 130) |
| hopO1-1 | AE016855 | 19413 | 22550 | 3200 | aacagggagagggtggtggtGGAAGGCGACAACATGCAGAG (SEQ ID NO: 131) | ggtggtagcggtgcgtaagtTGCGGATTGATAGGTATTTTCACT (SEQ ID NO: 132) |
| hopX1 | AE016855 | 14710 | 16308 | 1600 | aacagggagagggtggtggtGGGGTCGCCTCAGAAAACGGA (SEQ ID NO: 133) | ggtggtagcggtgcgtaagtAGCCAAGGCCAAGGGCGTGA (SEQ ID NO: 134) |
| hopY1 | NC_004578 | 82161 | 83593 | 1470 | aacagggagagggtggtggtGCCAATGCGTTTCTCGATCT (SEQ ID NO: 135) | ggtggtagcggtgcgtaagtGCGCTGCTGATGGGTATCTT (SEQ ID NO: 136) |
| avrPtoB | NC_004578 | 3468369 | 3470377 | 2100 | aacagggagagggtggtggtCCGTATTCTTATGGAAGGGCA (SEQ ID NO: 137) | ggtggtagcggtgcgtaagtCAGGTGCGAAGTCCGTGA (SEQ ID NO: 138) |

Subsequent secondary PCR reactions with UAFA oligonucleotides that are chimeric in that their 3' end carries homology to UA1 or UA2 and their 5' end is rationally designed to yield FA-flanked GUs that are used as the basic cluster building block in a homologous recombination reaction. The term UAFA (rather than simply 'FA') is used here to emphasize that the choice of UA1 or UA2 is a design feature in these oligonucleotides. The FA sequences serve as the recombination reaction DNA substrates for joining separate GUs. In line with the specific goal of integrating these clusters in the genome of *P. syringae* pv. *tomato*, the homologous recombination reactions also contain the linearized shuttle vector pCPP6218 (FIG. 12A). The end product of these reactions is a circular DNA molecule that includes an artificial gene cluster as well as additional functions allowing replication and selection in yeast and *E. coli* and selection of single crossover recombination events at a defined location of the EEL region of a *P. syringae* pv. *tomato* DC3000 or derivative cell.

Two elementary parameters guide the configuration of artificial clusters: (1) The relative orientation and position of the FA at the extremities of the GUs as encoded by the UAFA oligonucleotides employed in the secondary PCR. (2) The composition of the mix of DNA fragments (GUs) which are the substrates of the recombination reaction. Note that if ≥2 distinct GUs sharing the same pair of flanking FAs are included in the assembly reaction, assuming equivalent recombination efficiencies, the resulting clusters will contain, with equal probability, any of these competing GUs. This property allows the creation of libraries of random clusters.

As long as the FA flanks of the GUs are designed to ensure that there is at least one accessible combination of homologous recombination events that allows circular closure of the growing recombinant DNA molecule, all arrangements of GUs and FA units at any position and in any orientation are theoretically possible. In order to simplify the practical design and implementation of the assemblies a small set of simple conventions has been adopted: (1) The FA at one extremity of the linearized pCPP6218 vector has been designated "START" (FIG. 12A). The 3' end strand of this extremity is referred to as the 'Forward' strand. Consequently, a UAFA oligonucleotide whose 5' sequence is identical to the sequence of this strand at the "Start" FA will be described as "Forward". This FA is defined as the origin of the assembly and the corresponding DNA strand is viewed as the reference strand. (2) Likewise, the other extremity of the pCPP6218 linearized vector, on the same strand (5' end of this extremity), has been designated "END" and the corresponding FA has been named "END", this FA is defined as the end of the assembly. (3) Beside these "external" FAs (specified by the vector's sequence), other artificial FA sequences were computationally created. One strand of each of these sequences has been designated as the "Forward" strand. (4) All assemblies were done such that the Forward strand of all the internal FAs was on the same strand as the "reference" strand of the vector.

Primary PCR: Generating Genetic Units with Universal Adapter (UA) Extensions on Both Ends.

Oligonucleotide primers employed for primary amplification of genetic elements of interest are composed of a 3'-end specific for the sequence of this element and a 5'-end with the sequence of one of two invariant UA regions. FIG. 6 summarizes the main features of the oligonucleotide pairs and target genetic units as typically implemented in the current version of the PRIVAS system. One specification requires that the forward strand of the UA1 element (AACAGGGAGAGGGTGGTGGT; SEQ ID NO:21) be appended to the coding strand of the first downstream coding sequence, about 150 bp upstream of predicted promoter regions (hrp box). The UA2 reverse strand (GGTGGTAGCGGTGCGTAAGT; SEQ ID NO:22) is appended on the other side, to the 5'-end of the non-coding strand, about 150 bp after the end of the last ORF of the genetic unit (to include potential transcription terminator sequences).

Secondary PCR: Obtaining Genetic Units Flanked with Flexible Adapter (FA) Homology Regions for DNA Assembly by Recombination.

Oligonucleotide primers used for secondary amplification are composed of a UA-specific segment in their 3'-end and a ~35 bp homology region in their 5'-end. The sequences of internal FAs were derived from a computer generated random 100 kb DNA sequence of 52% GC content. The "FastPCR" software (5) by PrimerDigital was used to generate a list of the best quality, i.e., no predicted secondary structures, no self annealing, homogenous annealing temperature and GC content, candidate 35-36 bp FA sequences drawn from this "random" molecule. Both UA sequences were in turn systematically appended to the 3'-end of this set of candidate FAs and their reverse complement sequence. The resulting oligonucleotides that exhibited more than 65% identity with the DC3000 genome were excluded from the resulting set. Again they were tested for quality and all possible pairs were inspected for potential dimer formation. This provided a sense of how UAFA oligonucleotide sets, composed of combinations of a FA sequence (forward or reverse strands) and a UA sequence (UA1 or UA2) were likely to perform in PCR reactions with other UAFA oligonucleotide sets (compatibility). From the in silico analysis and selection process of candidate UAFA oligonucleotides was derived the FA connection FIG. 12B, which can be used as a guide for the setup of assemblies of up to 5 GUs in size. An arbitrary strand of each FA has been designated the "forward" strand and is always located on the forward strand of the construct. In addition to assembly paths deemed "accessible", the network also depicts the paths that were successfully implemented in this version of PRIVAS.

In addition to programming the position of GUs inside a designed cluster, the system also offers the option to "flip" the genetic units relative to their bordering FAs by using a pair of oligonucleotides with the appropriate combinations of UA and FA strand sequences. In cases where, for example, the transcriptional isolation of individual GUs is to be maximized to avoid downstream effects, it is possible to assemble GUs in a "head to head"/"tail to tail" pattern so that transcription of two neighboring GUs proceeds in opposite directions. Based on inspection of natural effector gene clusters on the DC3000 genome and on preliminary tests, the assemblies were systematically programmed to achieve this type of configuration with flanking GUs in opposite orientation and with the GU at position 1 (immediately after FA_START) in the same orientation as the nptII gene of the vector. Conversely, if a given GU needs to be placed under the transcriptional control of a promoter belonging to another GU, an artificial operon can be created (this is contingent upon negligible transcription termination activity of UAFA sequence bridging those GUs, which is likely since these sequences were selected for minimal secondary structure formation potential).

FIG. 12C gives an illustration of how the choice of the UAFA oligonucleotide pair used in secondary PCR impacts the orientation of the targeted GU in subsequent assembly.

Tables 5 and 6 list the UAFA oligonucleotide pairs used in secondary PCR reactions and their respective sequence. It also indicates the FA flanks of the resulting GU and its orientation in assemblies.

TABLE 5

UAFA Oligonucleotide Pairs Used in Secondary PCR Reactions

| Flanking forward strand Fas ('-') indicates that GU is flipped) | Primer name | FA | FA strand | UA |
|---|---|---|---|---|
| FA START+FA001 | oSC491 | FA START | F | UA1F |
| | oSC484 | FA001 | R | UA2R |
| FA START-FA001 | oSC492 | FA START | F | UA2R |
| | oSC483 | FA001 | R | UA1F |
| FA START+FA END | oSC490 | FA END | R | UA2R |
| | oSC491 | FA START | F | UA1F |
| FA START-FA END | oSC492 | FA START | F | UA2R |
| | oSC489 | FA END | R | UA1F |
| FA001+FA048 | oSC534 | FA048 | R | UA2R |
| | oSC481 | FA001 | F | UA1F |
| FA001-FA048 | oSC533 | FA048 | R | UA1F |
| | oSC482 | FA001 | F | UA2R |
| FA001+FA002 | oSC488 | FA002 | R | UA2R |
| | oSC48I | FA001 | F | UA1F |
| FA001-FA002 | oSC482 | FA001 | F | UA2R |
| | oSC487 | FA002 | R | UA1F |
| FA001+FA END | oSC481 | FA001 | F | UA1F |
| | oSC490 | FA END | R | UA2R |
| FA001-FA END | oSC482 | FA001 | F | UA2R |
| | oSC489 | FA END | R | UA1F |
| FA048+FA091 | oSC538 | FA091 | R | UA2R |
| | oSC531 | FA048 | F | UA1F |
| FA048-FA091 | oSC537 | FA091 | R | UA1F |
| | oSC532 | FA048 | F | UA2R |
| FA091+FA002 | oSC488 | FA002 | R | UA2R |
| | oSC535 | FA091 | F | UA1F |
| FA091-FA002 | oSC536 | FA091 | F | UA2R |
| | oSC487 | FA002 | R | UA1F |
| FA002+FA END | oSC490 | FA END | R | UA2R |
| | oSC485 | FA002 | F | UA1F |
| FA002-FA END | oSC486 | FA002 | F | UA2R |
| | oSC489 | FA END | R | UA1F |

TABLE 6

Sequence of UAFA oligonucleotide pairs used in secondary PCR reactions.

| Primer name | Sequence | SEQ ID NO: |
|---|---|---|
| oSC481 | TACGATGCCAGGATTGTGCGATCTTCACGCTCAGGaacagggagagggtggtggt | 139 |
| oSC482 | TACGATGCCAGGATTGTGCGATCTTCACGCTCAGGggtggtagcggtgcgtaagt | 140 |
| oSC483 | CCTGAGCGTGAAGATCGCACAATCCTGGCATCGTAaacagggagagggtggtggt | 141 |
| oSC484 | CCTGAGCGTGAAGATCGCACAATCCTGGCATCGTAggtggtagcggtgcgtaagt | 142 |

TABLE 6-continued

Sequence of UAFA oligonucleotide pairs used in secondary PCR reactions.

| Primer name | Sequence | SEQ ID NO: |
|---|---|---|
| oSC485 | ACATCTGGCTCACGATATGCCAAACTGCCTCGCCTaacagggagagggtggtgt | 143 |
| oSC486 | ACATCTGGCTCACGATATGCCAAACTGCCTCGCCTggtggtagcggtgcgtaagt | 144 |
| oSC487 | AGGCGAGGCAGTTTGGCATATCGTGAGCCAGATGTaacagggagagggtggtggt | 145 |
| oSC488 | AGGCGAGGCAGTTTGGCATATCGTGAGCCAGATGTggtggtagcggtgcgtaagt | 146 |
| oSC489 | TGGGAAGGGCGATCGGTGCGGGCCTCTTCGCTCTCGaacagggagagggtggtggt | 147 |
| oSC490 | TGGGAAGGGCGATCGGTGCGGGCCTCTTCGCTCTCGggtggtagcggtgcgtaagt | 148 |
| oSC491 | ACGTGTCATCGGTTGCGTCATCGGCTGGGAGCATCaacagggagagggtggtggt | 149 |
| oSC492 | ACGTGTCATCGGTTGCGTCATCGGCTGGGAGCATCggtggtagcggtgcgtaagt | 150 |
| oSC531 | GAGTGGACGTTTACAACATCGATCGCCTCGAACCCAaacagggagagggtggtggt | 151 |
| oSC532 | GAGTGGACGTTTACAACATCGATCGCCTCGAACCCAggtggtagcggtgcgtaagt | 152 |
| oSC533 | TGGGTTCGAGGCGATCGATGTTGTAAACGTCCACTCaacagggagagggtggtggt | 153 |
| oSC534 | TGGGTTCGAGGCGATCGATGTTGTAAACGTCCACTCggtggtagcggtgcgtaagt | 154 |
| oSC535 | GCAGTGTTGGAGTTTTGTACCTCCAGTTGCGGCGAaacagggagagggtggtgt | 155 |
| oSC536 | GCAGTGTTGGAGTTTTGTACCTCCAGTTGCGGCGAggtggtagcggtgcgtaagt | 156 |
| oSC537 | TCGCCGCAACTGGAGGTACAAAACTCCAACACTGCaacagggagagggtggtgt | 157 |
| oSC538 | TCGCCGCAACTGGAGGTACAAAACTCCAACACTGCggtggtagcggtgcgtaagt | 158 |

Random Assemblies in Yeast: Design Methodology.

As used herein, an "assembly or cluster size" refers to the number of GUs that make up the cluster or the clusters derived from a specifically designed assembly process. A "bin" is defined as a set of GUs sharing the same pair of flanking FAs corresponding to a position within a random cluster.

In the random mode of PRIVAS, the primary parameter driving the configuration of the resulting clusters is the composition of the pool of GUs transferred into yeast. Hence, the assembly design scheme aims at rationally selecting the GUs (and their flanking FAs) participating in the recombination reaction so as to achieve specific objectives relative to the properties of the assembled random islands (size, prototypic configuration, degree of complexity, etc.). For the construction of the cluster libraries screened in this work, the main goals were to minimize cluster configuration biases and maximize the exploration of the available cluster space.

In preliminary experiments it was realized that if DNA molecules participating in the in vivo assembly reaction share extensive identity outside of the FA sequences, these regions frequently undergo homologous recombination as well, and cause the permutation of flanking FAs. This phenomenon can markedly interfere with the specified assembly path and one of its main effects is the formation of clusters with a size deviating from the assembly size specified by design. Although this process can further increase the diversity of cluster configurations, it is not desirable as it decreases control over assembly size and may introduce major biases in favor of a few genetic elements. Therefore, to restrict the potential for "internal" recombination, pools of GUs in random assemblies were set up so that a given GU was assigned to one and only one bin.

The random assembly strategy involved multiple independent parallel assemblies of equal size and different bin compositions and attempted to meet the following requirements: (1) For a given assembly, all available primary PCR products must be included, each assigned to a unique bin. (2) Across the set of parallel assemblies, two primary PCR products should have the same overall probability to fall together in a bin or conversely to appear simultaneously on a random cluster. (3) To randomize positional effects, a mechanism ensuring that a given GU is not always located at the same position across assemblies should be developed. (4) Ideally, as many parallel assemblies as necessary should be performed so that a large fraction of the possible combinations of primary PCR products is accessible.

In order to follow the guidelines stated above, the existing algorithmic toolbox of the discipline of design of experiments was utilized. The problem of deciding on bins composition in parallel assemblies can be reformulated in terms of finding a near-optimal balanced incomplete block design where the number of treatments v is given the value of the number of distinct primary PCR products included in the experiment (in this study v=15); the number of blocks b is equivalent to the assembly size (i.e., number of bins, in this study, 3 or 5); the block size k is an integer equal to v/k and equivalent to the constant size of the bins; r the number of complete replicates of v treatments is equivalent to the number of parallel assemblies (restricted to 4 in this study). The adopted design plans were obtained using the RRCD module (Nguyen and Williams, "An Algorithm for Constructing Optimal Resolvable Row-Column Designs," *Australian and New Zealand Statistics* 35:363 (1993), which is hereby incorporated by reference in its entirety) of the Gendex software (DesignComputing). Two sets of assemblies, of sizes 3 and 5 GUs, are reported herein. Each set consisted in 4 parallel recombination reactions whose compositions followed the design proposed by the software. Following assembly, transfer into *E. coli* and conjugation into a *P. syringae* pv. *tomato* DC3000 derivative for recombination, colonies on selection media were transferred in microplates to generate the libraries that were subsequently partially screened on *N. benthamiana*.

Inferring Random Cluster Configuration.

In cases where the system is used to produce libraries of random clusters for functional assays, the problem of inferring the configuration of clusters of interest inevitably arises. Here the "configuration" is taken as an accurate description of the identity and orientation of the genetic elements at each position of the cluster. The "composition" on the other hand can be defined as an unordered list of genetic elements regardless of the orientation and position. The ideal way to elucidate the cluster configurations would be to have access to the error-free, complete DNA sequence of the clusters. As this was not feasible in practice for more than a handful of strains, a strategy was conceived to infer the cluster configuration of several dozens of strains with acceptable confidence.

Considering the primary PCR products that were included in the construction of the libraries of random clusters of size 3 or 5, it is clear that the theoretical maximal length of a size 5 cluster is less than 15 kb which is within the capabilities of current commercial high performance PCR kits. Therefore the entire clusters were directly PCR amplified using oligonucleotide primers annealing on the conserved external borders of the clusters. The resulting amplicons were subsequently used as templates in several sequencing reactions primed with oligonucleotides specific for the sequence of the FAs known to be upstream of the various positions as specified in the corresponding assembly design. The experimental DNA sequence obtained subsequently was used to infer the identity and orientation of the primary PCR product at this position in the examined cluster. This procedure is relatively easy to perform on dozens or even hundreds of strains but it is likely that the largest clusters will be amplified with low efficiency, thereby restricting an exhaustive unbiased analysis. Moreover, because only a ~200-900 bp segment of the primary PCR products is actually available, downstream rearrangements cannot be formally ruled out. Despite the above limitations, this procedure was satisfactorily employed to elucidate the hypothetical configuration of the clusters from 56 strains.

The inference methodology is based on a simple unambiguous mapping between (i) the experimental sequences obtained with (ii) a specific FA-specific sequencing oligonucleotide, from the cluster PCR product of (iii) a specific strain to (iv) a specific individual GU. This mapping was obtained by systematically querying a custom BLAST database containing the sequences of the amplified primary PCR derived from the DC3000 genome with the experimental sequences. A few experimental sequences failed to produce a hit after this search (see FIG. 8), but in all cases they aligned with unspecific regions when used to run a BLAST on the DC3000 genome and probably originated from unspecific amplification at the primary PCR stage Example 4

Laboratory Protocols Used in PRIVAS

Overview.

Primers employed in primary and secondary PCRs were synthesized by Integrated DNA Technologies (Coralville, Iowa). PCR reactions were performed with the high fidelity PrimeSTAR HS DNA Polymerase from Takara Bio Inc. For programmed assembly of clusters of size 1-3 or 5 GUs, a pool of FA-flanked GUs (~100 ng of each) obeying one of the paths presented in FIGS. 12A-12C, together with 75 ng of the linearized pCPP6218 plasmid, were transformed into yeast strain MaV203 from Invitrogen (Carlsbad, Calif.) using the standard lithium acetate/polyethylene glycol procedure, and the resulting recombinant circular shuttle vectors were selected over re-circularized empty vector using cycloheximide counterselection. Plasmids purified from yeast were introduced into *E. coli* S17-1 strain and then conjugated into *P. syringae* (Kvitko et al., "Deletions in the Repertoire of *Pseudomonas syringae* pv. *tomato* DC3000 Type III Secretion Effector Genes Reveal Functional Overlap Among Effectors," *PLoS Pathogens* 5:e1000388 (2009), which is hereby incorporated by reference in its entirety). Similar to the procedure for the analysis of random clusters, the configurations of the programmed clusters assembled with PRIVAS were checked by *P. syringae* colony PCR amplification (FIG. 1B). The proper nature and orientation of the GUs were verified by sequencing of the amplified DNA region immediately downstream of the FAs. For the creation of random cluster libraries, the composition of the pools of competing GUs in parallel assemblies followed a near-optimal balanced incomplete block design where the positions within the clusters represent blocks and the set of 15 tested GUs is equivalent to treatment levels. The PRIVAS system and GU genomic contexts are further described infra (see also FIG. 10).

Primary PCR (Amplify and Append Universal Adapter Sequences).

To minimize the introduction of mutations, the PCR reactions were performed with the high fidelity PrimeSTAR HS DNA Polymerase from Takara Bio Inc. The primary PCR reaction mix contained 20 µl of 5× PrimStart Buffer, 8 µl of the provided dNTPs, 2 µl of each GU-specific UA primer synthesized by Integrated DNA Technologies (Coralville, Iowa) at 10 µM, ~50 ng of *P. syringae* pv. *tomato* DC3000 genomic DNA and 2.5 units of PrimeSTAR HS DNA polymerase. Table 4 (above) shows the sequences of the gene-specific primer containing universal adapter oligonucleotides. This 100 μl reaction mix was split into two tubes to carry out independent reactions and decrease the chances that early mutations predominate after amplification. A typical thermal program included an initial denaturation of 1.5 min at 94° C. followed by a first segment of 7 cycles utilizing a touch-down procedure: denaturation at 98° C. for 10 s, annealing at 72° C.-2° C./cycle for 5 sec and extension at 72° C. for 2.5 min. The second segment consisted in 23 cycles of 98° C. for 10 s, 56° C. for 5 sec and 72° C. for 4 min. The replicate reactions were pooled and a 30 μl aliquot was run on an agarose gel. The band at the expected specific size was purified with the DNA Recovery Kit and Clean-up and Concentrator Kit from Zymo Research (Orange, Calif.). An aliquot was sequenced at the Cornell University Biotechnology Resource Center to verify the identity of the amplified DNA fragment.

Secondary PCR (Append Flexible Adapter Sequences).

Secondary PCR reactions were performed as above except that the second segment involved only 16 cycles. A 1/100 dilution of the purified primary PCR fragment was used as a template and the appropriate pair of UAGS primers also synthesized by Integrated DNA Technologies was included in the amplification mix. To verify amplification and specificity, 3 μl aliquots were systematically run on an agarose gel and the rest was stored at −20° C. and used without further purification for yeast transformation and cluster assemblies.

Yeast Transformation for Recombinational Assembly of Clusters.

The yeast transformation procedure essentially followed the protocol from Clontech's Yeastmaker transformation system (Mountain View, Calif.). The yeast strains MaV203 (Genotype: MATα; leu2-3, 112; trp1-901; his3Δ200; ade2-101; cyh2$^R$; can1$^R$; gal4Δ; gal80Δ; GAL1::lacZ; HIS3$_{UASGAL1}$::HIS3@LYS2: SPAL10$_{UASGAL1}$::URA3) from Invitrogen (Carlsbad, Calif.) was used as a recipient and allows counterselection of re-circularized pCPP6218 vector that carries the wild type dominant cycloheximide susceptibility allele of the CYH2 gene (Raymond et al., "Linker-Mediated Recombinational Subcloning of Large DNA Fragments Using Yeast," Genome Res. 12:190-7 (2002), which is hereby incorporated by reference in its entirety). For a small scale transformation in a 1.5 ml tube, 75 ng of the XhoI/SpeI-linearized and gel purified pCPP6218 shuttle vector and 1.5 μl (50-100 ng) of each secondary PCR product where included in the transformation mix together with the carrier DNA. Directly after heat treatment at 42° C. the cell pellet was suspended in sterile water and plated on SD selection media lacking tryptophan with glucose and 5 μg/ml cycloheximide. After 3-4 days at 28° C., a small scale transformation produced more than 2×10$^4$ colonies on selection plates.

Recovery of Plasmid DNA from Yeast.

The OD$_{600}$ of yeast cells resuspended from the selection plate or grown overnight in liquid SD media was adjusted to approximately 3-4 in 250 μl of the P1 buffer from the QIAprep Spin Miniprep Kit of Qiagen (Valencia, Calif.) and 5 mg/ml lyticase from Sigma-Aldrich (St. Louis, Mo.). After one hour incubation at 37° C. and occasional mixing, cells were disrupted through two cycles of incubation in liquid nitrogen for 30 s followed by 10 min at 65° C. After the final heat-shock, tubes were allowed to cool down to room temperature and buffer P2 (250 μl) was added. The rest of the procedure followed the protocol provided in the kit and included the endonuclease wash step. Plasmid DNA was eluted in 30 μl water.

E. coli S17-1 Electroporation.

Electrocompetent E. coli S17-1 cells were transformed with 10 μl of the DNA preparation extracted from yeast according to standard protocols.

Conjugation of Pseudomonas syringae pv. tomato DC3000 Derivatives for Single Cross-Over Insertion of the Clusters at the EEL.

Bacterial conjugations between the donor E. coli S17-1 cells and recipient DC3000 derivatives were performed essentially as described in (Kvitko et al., "Deletions in the Repertoire of Pseudomonas syringae pv. tomato DC3000 Type III Secretion Effector Genes Reveal Functional Overlap Among Effectors," PLoS Pathogens 5:e1000388 (2009), which is hereby incorporated by reference in its entirety). For generation of random cluster libraries, E. coli S17-1 cells growing on selection plates were resuspended in liquid LB media and the OD$_{600}$ was adjusted to 2.0 and 200 μl of this suspension was mixed with an equal volume of an overnight culture of the recipient strain. The remainder was stored at −80° C. in 15% glycerol. After 3 days on kanamycin selection plates, more than 5000 colonies were obtained per transformation.

Colony PCR Amplification of Integrated Clusters.

Amplification of entire clusters integrated at the EEL used the Premix Taq (Ex Taq Version) PCR kit of Takara Bio, Inc with primers GCTGCTCCATTCCTTCGAGATGC (SEQ ID NO:159) and GCTTTCTACGTGTTCCGCTTCCTTTAG (SEQ ID NO:160) annealing outside of the external FAs (START and END). Thermal cycling conditions were as follow: a single step at 94° C. for 2 min; denaturation for 10 s at 98° C. annealing at 60° C. for 30 s and extension at 72° C. for 13 min, for a total of 35 cycles and 20 min final extension at 72° C.

ExoSap Clean-Up of Cluster PCR Products for Sequencing.

Prior to sequencing, 5 μl of the PCR reactions containing the cluster amplicons were treated with 0.25 μl Exonuclease I (20 U/μl) and 0.5 μl Antartic Phosphatase (5 U/μl) from New England Biolabs (Ipswich, Mass.) at 37° C. for 30 min followed by heat inactivation for 15 min at 80° C. to degrade remaining primers and neutralize unincorporated dNTPs. An appropriate sequencing primer from Table 7 was combined with the resulting DNA solution and sequenced at the Cornell University Biotechnology Resource Center.

TABLE 7

Oligonucleotide Primers Used for Sequencing.

| Anneals on reverse strand of | Primer Sequence | SEQ ID NO: |
|---|---|---|
| FA START | ACGTGTCATCGGTTGCGTC | 161 |
| FA001 | TACGATGCCAGGATTGTGCG | 162 |
| FA002 | TCACGATATGCCAAACTGCC | 163 |
| FA048 | GAGTGGACGTTTACAACATCGATC | 164 |
| FA091 | GCAGTGTTGGAGTTTTGTACCTC | 165 |

Example 5

Construction of *P. syringae* pv. *tomato* DC3000D28E, a Functionally Effectorless Polymutant Many proteobacterial pathogens of plants and animals disarm and infect their hosts by injecting 20-50 or more effector proteins via the type III secretion system (T3SS) (Kenny and Valdivia, "Host-Microbe Interactions: Bacteria," *Curr. Opin. Microbiol.* 12:1-3 (2009), which is hereby incorporated by reference in its entirety). Studies focused on a few individual type III effectors (T3Es) in the repertoires of model pathogens have yielded seminal insights into host targets and T3E activities, but they also suggest that T3Es in a given repertoire, such as that of enteropathogenic *E. coli* E2348/69, function in a "multifunctional, cooperative, and redundant" manner (Dean and Kenny, "The Effector Repertoire of Enteropathogenic *E. coli*: Ganging Up on the Host Cell" *Curr Opin Microbial* 12:101-9 (2009), which is hereby incorporated by reference in its entirety). That is, T3E repertoires may function as systems with properties beyond those of individual effectors.

The T3E repertoire of *Pseudomonas syringae* pv. *tomato* DC3000, which can cause disease in tomato and the model plants *Arabidopsis thaliana* and *Nicotiana benthamiana*, is particularly amenable to systems-level study (Buell et al., "The Complete Sequence of the *Arabidopsis* and Tomato Pathogen *Pseudomonas syringae* pv. *tomato* DC3000," *Proc. Nat'l. Acad. Sci. USA* 100:10181-10186 (2003), which is hereby incorporated by reference in its entirety). The DC3000 T3Es, which are designated as Hop (Hrp outer protein) or Avr (avirulence) proteins, have been comprehensively identified, and 28 T3Es have been shown to be well-expressed and deployed during infection (Chang et al., "A High-Throughput, Near-Saturating Screen for Type III Effector Genes From *Pseudomonas syringae*," *Proc. Nat'l. Acad. Sci. USA* 102:2549-2554 (2005); Vinatzer et al., "Bioinformatics Correctly Identifies Many Type III Secretion Substrates in the Plant Pathogen *Pseudomonas syringae* and the Biocontrol Isolate *P. fluorescens* SBW25," *Mol. Plant Microbe Interact.* 18:877-888 (2005); Schechter et al., "Multiple Approaches to a Complete Inventory of *Pseudomonas syringae* pv. *tomato* DC3000 Type III Secretion System Effector Proteins," *Mol. Plant-Microbe Interact.* 19:1180-1192 (2006); and Lindeberg et al., "Closing the Circle on the Discovery of Genes Encoding Hrp Regulon Members and Type III Secretion System Effectors in the Genomes of Three Model *Pseudomonas syringae* Strains," *Mol. Plant Microbe Interact.* 19:1151-1158 (2006), which are hereby incorporated by reference in their entirety). The activities and targets in plants of several of these T3Es have been determined (Cunnac et al., "*Pseudomonas syringae* Type III Secretion System Effectors: Repertoires in Search of Functions," *Curr. Opin. Microbiol.* 12:53-60 (2009), which is hereby incorporated by reference in its entirety).

According to a current model for plant-pathogen interactions (Jones and Dangl, "The Plant Immune System," *Nature* 444:323-9 (2006), which is hereby incorporated by reference in its entirety), the primary function of *P. syringae* T3Es is to suppress PAMP (pathogen-associated molecular pattern)-triggered immunity (PTI), which is elicited by common bacterial factors, such as flagellin, interacting with pattern recognition receptors (PRRs) on plant cell surfaces. Plants have a defense against T3Es that is based on detection inside plant cells of their presence or activity by resistance (R) proteins, which results in effector-triggered immunity (ETI). Pathogens may evade ETI by eliminating effectors that have become avirulence determinants or by deploying other effectors that suppress ETI. This model predicts a coevolutionary process that would generate the observed amplification and polymorphism in genes encoding effectors in pathogens and PTI components and R proteins in plants. Determining general properties of these complex interaction systems, which also occur with many pathogenic fungi, oomycetes, and nematodes and their comparable effectors, has practical potential because of the widespread use of resistance breeding for crop protection and the frequent failure of resistance in the face of pathogen variation in the field (Poland et al., "Shades of Gray: The World of Quantitative Disease Resistance," *Trends Plant Sci.* 14:21-9 (2009), which is hereby incorporated by reference in its entirety).

The majority of the well-expressed DC3000 T3Es are encoded within six clusters in the DC3000 genome (Wei et al., "A *Pseudomonas syringae* pv. *tomato* DC3000 Mutant Lacking the Type III Effector HopQ1-1 Is Able to Cause Disease in the Model Plant *Nicotiana benthamiana*," *Plant J.* 51:32-46(2007), which is hereby incorporated by reference in its entirety). Deletions of individual clusters revealed HopQ1-1 to function as the sole avirulence determinant for DC3000 in *N. benthamiana*, a plant that is particularly amenable to high-throughput genetic manipulation and bacterial growth assays (Wei et al., "A *Pseudomonas syringae* pv. *tomato* DC3000 Mutant Lacking the Type III Effector HopQ1-1 Is Able to Cause Disease in the Model Plant *Nicotiana benthamiana*," *Plant J.* 51:32-46 (2007) and Goodin et al., "*Nicotiana benthamiana*: Its History and Future as a Model for Plant-Pathogen Interactions," *Mol. Plant Microbe Interact.* 21:1015-26 (2008), which are hereby incorporated by reference in their entirety). Combinatorial deletions revealed only a small reduction in growth in *N. benthamiana* with the loss of 15 T3E genes in 5 clusters but a stronger reduction with the loss of just two or three T3E genes in either of two redundant effector groups (REGs). For example, a strong reduction in growth accompanied the combined loss of avrPto and avrPtoB, which comprise one REG. These observations suggest that the composition of T3E repertoires is functionally structured (Kvitko et al., "Deletions in the Repertoire of *Pseudomonas syringae* pv. *tomato* DC3000 Type III Secretion Effector Genes Reveal Functional Overlap Among Effectors," *PLoS Pathogens* 5:e1000388 (2009), which is hereby incorporated by reference in its entirety), but the difficulty of constructing alternative combinatorial polymutants has limited further exploration of interplay and redundancy in the DC3000 T3E repertoire.

As described herein, using the dual adapter recombination method of the present invention, a functionally effectorless derivative of DC3000, designated DC3000D28E (deficient in 28 effectors) was constructed. The programmable and random in vivo assembly shuttle (PRIVAS) system of the present invention enabled partial reassembly of the T3E repertoire in DC3000D28E, and identification of a minimal functional repertoire of T3Es that restores near-wild-type growth and symptom production in *N. benthamiana*.

Figure 2:
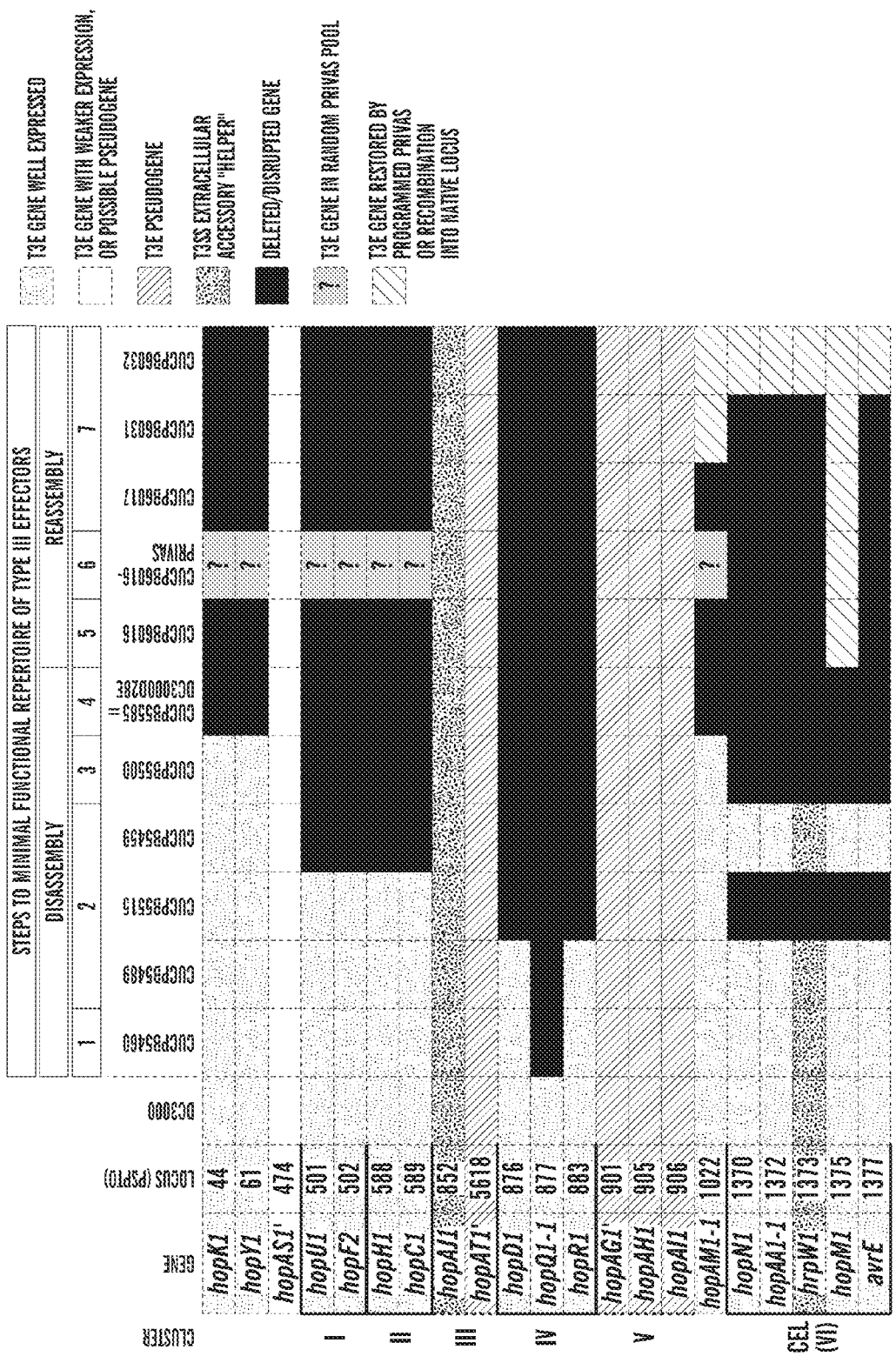
Figure 2:
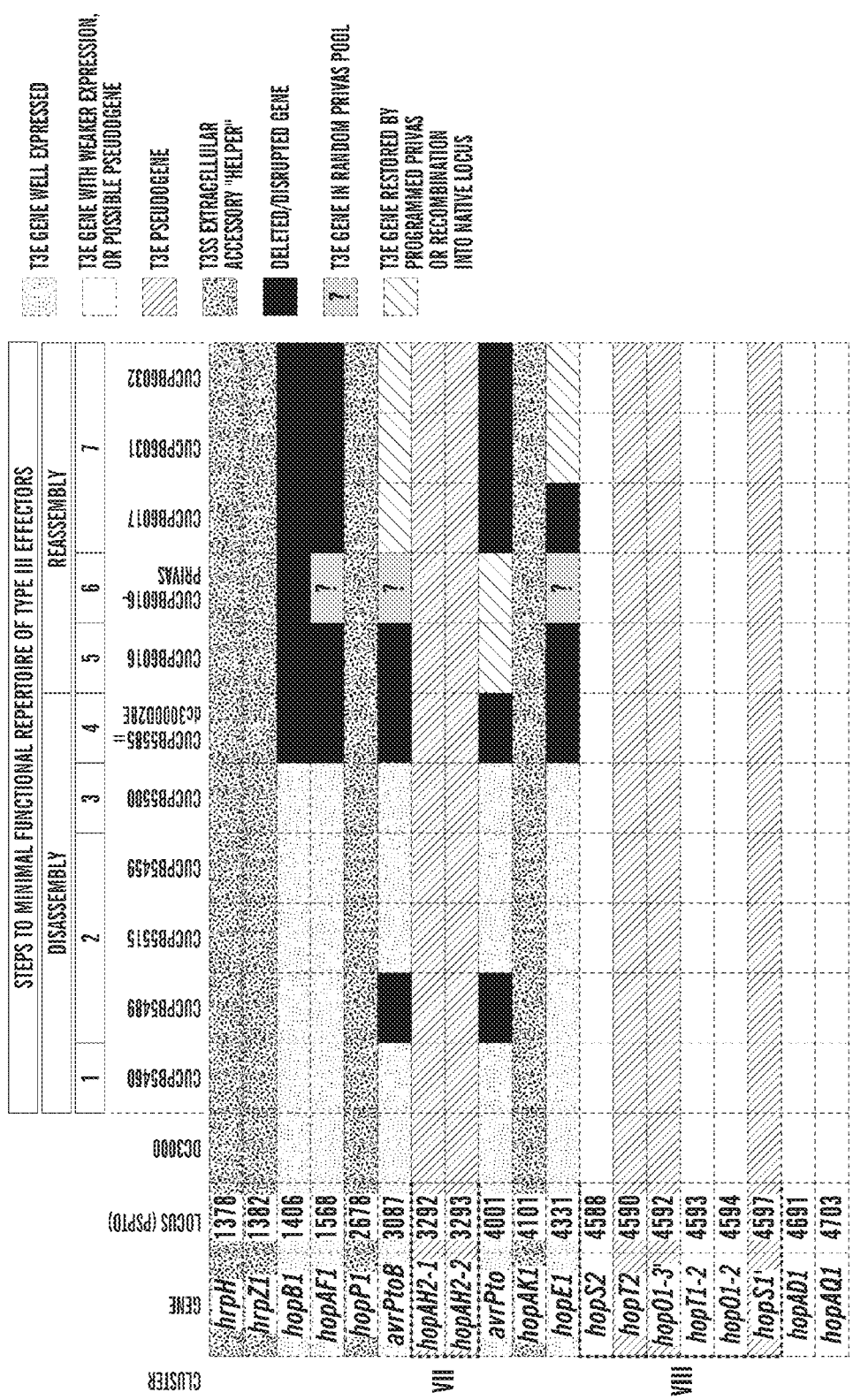
Figure 2:
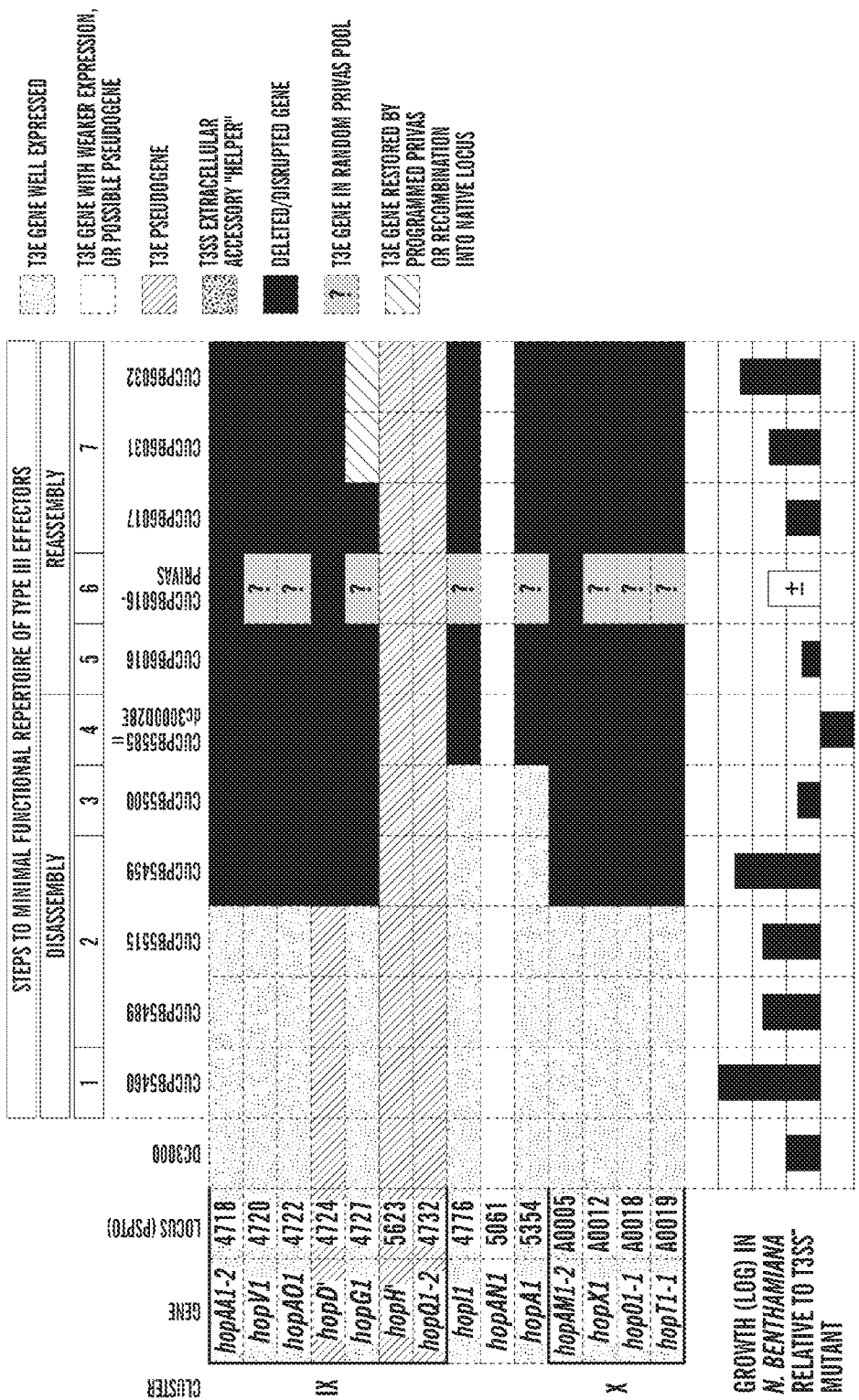

CUCPB5500, which lacks all 18 of the well-expressed T3E genes occurring in clusters, was previously constructed (Kvitko et al., "Deletions in the Repertoire of *Pseudomonas syringae* pv. *tomato* DC3000 Type III Secretion Effector Genes Reveal Functional Overlap Among Effectors," *PLoS Pathogens* 5:e1000388 (2009), which is hereby incorporated by reference in its entirety). Here the remaining 10 well-expressed T3E genes were deleted, again using pK18mobsacB (Wei et al., "A *Pseudomonas syringae* pv. *tomato* DC3000 Mutant Lacking the Type III Effector HopQ1-1 Is Able to Cause Disease in the Model Plant *Nicotiana benthamiana*," *Plant J.* 51:32-46 (2007), which is hereby incorporated by reference in its entirety), to produce polymutant DC3000D28E (CUCPB5585 in FIG. 1). FIG. 2 provides an overview of the genetic manipulations of DC3000 and depicts relevant genes and clusters, as well as T3E pseudogenes and genes that appear to be only weakly expressed (Chang et al., "A High-Throughput, Near-Saturating Screen for Type III Effector Genes From *Pseudomonas syringae*," *Proc. Nat'l. Acad. Sci. USA* 102:2549-2554 (2005); Vinatzer et al., "Bioinformatics Correctly Identifies Many Type III Secretion Substrates in the Plant Pathogen *Pseudomonas syringae* and the Biocontrol Isolate *P. fluorescens* SBW25," *Mol. Plant Microbe Interact.* 18:877-888 (2005); Schechter et al., "Multiple Approaches to a Complete Inventory of *Pseudomonas syringae* pv. *tomato* DC3000 Type III Secretion System Effector Proteins," *Mol. Plant-Microbe Interact.* 19:1180-1192 (2006); and Lindeberg et al., "Closing the Circle on the Discovery of Genes Encoding Hrp Regulon Members and Type III Secretion System Effectors in the Genomes of Three Model *Pseudomonas syringae* Strains," *Mol. Plant Microbe Interact.* 19:1151-1158 (2006), which are hereby incorporated by reference in their entirety).

Example 6

Analysis of the Ability of DC3000D28E and Progenitors to Grow in *N. benthamiana*

CUCPB5500, DC3000D28E, and intermediate polymutants with successive T3E gene deletions were analyzed for their ability to grow in *N. benthamiana*. Leaves were inoculated with test strains at $3 \times 10^4$ colony-forming units (CFU)/ml by infiltration with a blunt syringe and assayed 6 days post-inoculation (dpi) for bacterial population levels (FIG. 1). Notably strong reductions in bacterial growth were observed with the successive deletions of avrPtoB and avrPto. The population levels of DC3000D28E were approximately 4 logs lower than that of DC3000ΔhopQ1-1, and lower than that of CUCPB5113, a T3SS-deficient DC3000 ΔhrcQ$_b$-hrcU (hereafter hrcQ-U) mutant. This observation prompted the construction of CUCPB5589, which is a ΔhrcQ-U derivative of DC3000D28E. Population levels of CUCPB5589 and CUCPB5113 were indistinguishable (FIG. 1)). These observations suggested that DC3000D28E was functionally effectorless and revealed a potential for the DC3000 T3SS machinery to stimulate plant defenses.

Example 7

Functional Analysis of DC3000D28E

To determine whether DC3000D28E met key criteria for being functionally effectorless but otherwise wild type in planta, the ability of the mutant to grow robustly in apoplast-mimicking minimal media, deliver a translocation reporter into plant cells, be strongly reduced in its ability to elicit cell death in plants, and grow to high levels in planta in the presence of another strain that is able to defeat plant immunity was tested. DC3000D28E grew similar to DC3000ΔhopQ1-1 in mannitol-glutamate minimal medium (Bronstein et al., "Global Transcriptional Responses of *Pseudomonas syringae* DC3000 to Changes in Iron Bioavailability in vitro," *BMC Microbiol.* 8:209 (2008), which is hereby incorporated by reference in its entirety) (FIG. 3A) and in Hrp minimal medium (FIG. 4B), but more slowly in rich Kings B medium (FIG. 4A). DC3000D28E carrying pCPP5702, a plasmid expressing avrPto-cya from its native promoter (Kvitko et al., "Identification of harpins in *Pseudomonas syringae* pv. *Tomato* DC3000, Which Are Functionally Similar to HrpK1 in Promoting Translocation of Type III Secretion System Effectors," *J. Bacteriol.* 189: 8059-8072 (2007), which is hereby incorporated by reference in its entirety), translocated the reporter as well as DC3000(pCPP5702) (with two levels of inoculum used to ensure that the assay was not saturated) (Kvitko et al., "Identification of harpins in *Pseudomonas syringae* pv. *Tomato* DC3000, Which Are Functionally Similar to HrpK1 in Promoting Translocation of Type III Secretion System Effectors," *J. Bacteriol.* 189:8059-8072 (2007), which is hereby incorporated by reference in its entirety) (FIG. 3B). DC3000D28E was compared with DC3000 and DC3000ΔhopQ1-1 for its ability to elicit cell death in *N. benthamiana* and nonhost *Nicotiana tabacum* at three inoculum levels chosen to exceed the threshold typically needed for elicitation of cell death associated with ETI. In both plants, 100 times more DC3000D28E was needed to elicit cell death 48 h after inoculation (FIG. 3C). Finally, DC3000D28E was compared with the DC3000 ΔhrcQ-U T3SS⁻ mutant for its ability to grow in *N. benthamiana* when co-inoculated with DC3000ΔhopQ1-1 and found to grow 4 logs better than without DC3000ΔhopQ1-1 (FIG. 1) and at least as well in this test as the ΔhrcQ-U mutant (FIG. 3D). Collectively, these observations suggest that DC3000D28E is functionally effectorless, and although inexplicably growing more slowly in a rich medium, does not appear to have second site mutations that impair its ability to grow in planta and therefore is suitable for testing T3Es for their ability to restore bacterial growth and induction of plant responses.

Example 8

Recombination into Native Loci of Genes Representing Two REGs Reveals that AvrPto and AvrPtoB Act at an Early Phase of the Plant Immune Response Previous work highlighted the importance of the AvrPto/AvrPtoB and AvrE/HopM1/HopR1 REGs (Kvitko et al., "Deletions in the Repertoire of *Pseudomonas syringae* pv. *tomato* DC3000 Type III Secretion Effector Genes Reveal Functional Overlap Among Effectors," *PLoS Pathogens* 5:e1000388 (2009), which is hereby incorporated by reference in its entirety). Experimental reassembly of the DC3000 T3E repertoire began by integrating avrPto, avrPtoB, hopM1, and the entire conserved effector locus (CEL, or cluster VI, comprising avrE, hopM1, hopAA1-1, hopN1) into their native locations in the genome of DC3000D28E by using pK18mobsacB. bAvrPto and AvrPtoB both promoted significant growth, but neither HopM1 nor the entire set of CEL T3Es had this effect (FIG. 5). However, HopM1 was able to promote growth when combined with AvrPto or AvrPtoB, with maximal growth in these experiments occurring when AvrPtoB was combined with the complete CEL. Thus, AvrPto and AvrPtoB differ from members of the AvrE REG in appearing to be "early-acting effectors". Weak additive effects on growth promotion were observed with T3Es from the same REG, but stronger effects were observed when representatives of two REGs were combined, for example, when AvrPtoB was combined with HopM1 rather than AvrPto. These observations suggest a hierarchy in the action of *P. syringae* T3Es, they provide a baseline involving natively restored T3E genes for analyzing subsequent experiments involving engineered assemblies of T3Es, and they reveal that just two T3Es can promote 2 of the 4 logs of growth capacity that distinguishes DC3000D28E and DC3000ΔhopQ1-1.

Example 9

Development of the PRIVAS System

The ability of short, terminal adapters to direct recombination of unrelated DNA fragments in yeast (Raymond et al., "General Method for Plasmid Construction Using Homologous Recombination," *Biotechniques* 26:134-8, 140-1 (1999), which is hereby incorporated by reference in its entirety) was exploited, and a novel system of dual adapters to enable flexible assembly of multigene sets in shuttle vectors was developed. FIG. 6A6C illustrate the application of the PRIVAS system to the assembly of T3E multigene sets and their subsequent integration into the naturally polymorphic exchangeable effector locus (EEL) of *P. syringae* (Alfano et al., "The *Pseudomonas syringae* Hrp Pathogenicity Island Has a Tripartite Mosaic Structure Composed of a Cluster of Type III Secretion Genes Bounded by Exchangeable Effector and Conserved Effector Loci That Contribute to Parasitic Fitness and Pathogenicity in Plants," *Proc. Nat'l. Acad. Sci. USA* 97:4856-4861 (2000), which is hereby incorporated by reference in its entirety) By choosing the desired flexible adapters from a premade panel of adapters and varying the composition of the pool of substrates for DNA assembly, the system can construct programmed or random gene sets. The shuttle vector replicates in yeast and *E. coli* and carries a 1062-bp region of the DC3000 EEL. T3E genes used in this system are all expressed from native promoters and are cloned with their cognate chaperone genes where appropriate. To validate the PRIVAS system, it was used in programmed mode to introduce shcM-hopM1 into mutant CUCPB5515 (ΔIVΔCEL) and also avrPtoB and shcM-hopM1, sequentially, into DC3000D28E to reproduce the early-acting effector phenotype described in FIG. 5. In all cases, growth promotion was equivalent for T3E genes restored by PRIVAS and by homologous recombination into native loci (FIG. 7).

Example 10

Identification of Randomly Assembled T3E Gene Sets that Promote DC3000D28E Growth in *N. benthamiana*

The PRIVAS system was used in random mode to seek T3Es that could enhance bacterial growth of CUCPB6016 (DC3000D28E with avrPto and shcM-hopM1 restored to native loci). CUCPB6016 was chosen because it contains representatives of the AvrPto and AvrE REGs, and the use of AvrPto allowed AvrPtoB, with its stronger growth phenotype, to function as a positive control in the randomized PRIVAS procedure. Fifteen T3E-based genetic units (GUs) were chosen to form a manageable pool for initial construction of randomized T3E sets comprised of 3 or 5 GUs, with the shcF-hopF2-hopU1, hopAO1-shcV-hopV1 and shcO1-hopO1-1-hopT1-1 operons each comprising a single GU. Seven of the DC3000 T3E genes were excluded because they were associated with the CEL and the AvrE REG, whose growth contributions had been partially characterized (avrE, hopN1, hopAA1-1 and its paralog hopAA1-2, and hopR1), or potentially inhibit bacterial growth (hopD1) (Kvitko et al., "Deletions in the Repertoire of *Pseudomonas syringae* pv. *tomato* DC3000 Type III Secretion Effector Genes Reveal Functional Overlap Among Effectors," *PLoS Pathogens* 5:e1000388 (2009), which is hereby incorporated by reference in its entirety), or appear less common among sequenced *P. syringae* strains (hopB1) (Cunnac et al., "*Pseudomonas syringae* Type III Secretion System Effectors: Repertoires in Search of Functions," *Curr. Opin. Microbiol.* 12:53-60 (2009), which is hereby incorporated by reference in its entirety). CUCPB6016-PRIVAS strains were randomly chosen from the library for growth tests in *N. benthamiana*, where they were individually inoculated in four experiments involving 44 strains, each at ~$3\times10^4$ CFU/ml, and compared with CUCPB6022 (CUCPB6016 empty integrated PRIVAS vector control) and CUCPB5459 (ΔIΔIIΔIVΔIXΔX) for growth at 6 dpi. The strains tested included 92 from the libraries with 3-GU sets and 84 with 5-GU sets. As shown for a representative experiment, the 44 strains in each batch produced a continuum of population levels (FIG. 8A). DNA sequencing was then used to identify the introduced T3E genes in 56 strains chosen to represent the extremes of the phenotypic continuum in the 4 batches and the two classes of GU set size. This analysis yielded several key findings (FIG. 8B). avrPtoB was present in all of the strains with the strongest growth. hopE1 was also prevalent in these strains and in strains lacking avrPtoB that showed intermediate growth. Chlorosis was observed with some strains showing at least intermediate growth, and all of these strains contained hopG1.

In summary, the PRIVAS procedure permits facile introduction of random, small sets of T3Es into the genome of DC3000D28E, and it suggests that a few of the 18 T3Es present in the experimental pool may be particularly important in pathogenesis, although no combination restored virulence to near wild-type levels and alternative T3E gene combinations could produce relatively strong growth.

Example 11

Identification of a Minimal Functional T3E Repertoire for Virulence in *N. benthamiana*

The PRIVAS system was used in programmable mode to introduce a series of T3E genes into CUCPB6017 (DC3000D28E with avrPtoB and shcM-hopM1 restored to native loci). CUCPB6017 was chosen because the stronger growth contribution of AvrPtoB supported the goal of identifying a minimal functional repertoire. Three effector genes were chosen to add next because observations with the random PRIVAS experiment or the deletion series leading to DC3000D28E indicated a role in growth (hopE1), chlorosis (hopG1), or lesion cell death (hopAM1). Indeed, introduction of hopE1 into CUCPB6017 produced a small but significant increase in growth (FIG. 9B). Introduction of hopE1+hopG1 or hopE1+hopAM1-1 produced chlorosis and some cell death, respectively, if the inoculum level was raised to $3\times10^5$ (FIG. 9A). Combining these 5 T3E genes yielded an increase in growth that was significantly above the level promoted by avrPtoB+hopM1+hopE1 but substantially below the level of DC3000ΔhopQ1-1 (FIG. 9B). Finally, PRIVAS was used to introduce hopE1+hopG1+hopAM1-1 into CUCPB6019 (DC3000D28E with avrPtoB and the complete CEL restored to native loci). The resulting strain, CUCPB6032, produced robust symptoms in *N. benthamiana* and achieved population levels that were more than 3 logs better than DC3000D28E and within a log of DC3000ΔhopQ1-1 (FIG. 9). Thus, a minimal set of 8 T3Es is sufficient to restore the virulence of DC3000D28E in *N. benthamiana* to near wild-type levels.

Discussion of Examples 1-11

Plant pathogenic bacteria in the genera *Pseudomonas*, *Xanthomonas*, and *Ralstonia* deploy large T3E repertoires that have several systems-level properties regarding their contribution to virulence (Cunnac et al. "*Pseudomonas syringae* Type III Secretion System Effectors: Repertoires in Search of Functions," *Curr. Opin, Microbiol,* 12:53-60 (2009); Kvitko et al., "Deletions in the Repertoire of *Pseudomonas syringae* pv. *tomato* DC3000 Type III Secretion Effector Genes Reveal Functional Overlap Among Effectors," *PLoS Pathogens* 5:e1000388 (2009); Kay and Bonas, "How *Xanthomonas* Type III Effectors Manipulate the Host Plant," *Curr. Opin. Microbiol.* 12:37-43 (2009); and Poueymiro and Genin, "Secreted Proteins from *Ralstonia solanacearum*: A Hundred Tricks to Kill a Plant," *Curr. Opin. Microbiol,* 12:44-52 (2009), which are hereby incorporated by reference in their entirety): (i) T3Es collectively are essential; (ii) no single T3E is essential; (iii) some T3Es can be assigned to REGs that redundantly target distinct processes in plant defense, (iv) T3E repertoires can be highly variable, even among strains pathogenic on the same host; (v) heterologous expression and delivery of effectors from other strains, or even from oomycetes (Sohn et al., "The Downy Mildew Effector Proteins ATR1 and ATR13 Promote Disease Susceptibility in *Arabidopsis thaliana*," *Plant Cell* 19:4077-90 (2007), which is hereby incorporated by reference in its entirety), can increase the virulence of wild-type strains. Here, further properties of the DC3000 T3E repertoire have been discovered in the context of interactions with *N. benthamiana*: (i) no single T3E is sufficient for significant virulence; (ii) some T3Es appear to interfere with an early phase of the plant immune response (i.e., by disrupting PAMP perception) such that other T3Es make a contribution to virulence only in their presence; (iii) early-acting effectors also appear to suppress defenses elicited by the T3SS machinery; (iv) T3Es in small groups with reduced redundancy can contribute in a hierarchical fashion to growth and symptom production; (v) a minimal functional repertoire appears to require several effectors and members of at least two REGs. Before considering these generalizations in the context of specific T3Es and known host targets, the discovery path to the minimal functional repertoire must be discussed.

The search involved iterative introductions of 24 of the 28 well-expressed DC3000 T3E genes (FIG. 2). Growth phenotypes observed during repertoire disassembly led to the initial introduction of members of the AvrPto and AvrE REGs and then to the use of one member of each REG as the foundation for construction of a minimal functional repertoire. The PRIVAS system in random mode enabled the search of a large number of combinations of 18 T3Es not known to be associated with these REGs or the CEL (other than the AvrPtoB positive control). No single T3E gene newly introduced at the random PRIVAS stage made a notably strong contribution to growth, but several different T3E combinations made modest contributions. hopE1, hopG1, and hopAM1 were chosen to explore, and the minimal functional repertoire defined appears to involve some synergy between these three T3Es and the CEL T3Es. as seen by comparing the relative growth of CUCPB6032 with that of CUCPB6019 and CUCPB6031 in FIGS. 5 and 9. Thus, although AvrPtoB and the CEL T3Es are clearly important, they are insufficient for a minimal functional repertoire (and it is possible that not all four of the CEL T3Es are necessary). However, the data strongly suggest that DC3000 requires at least 6 T3Es to grow and cause disease in *N. benthamiana*, a model plant that is not a natural host for wild-type DC3000 and appears to be unusually susceptible to a variety of pathogens (although possessing fully functional PTI and ETI systems) (Goodin et al., "*Nicotiana benthamiana*: Its History and Future as a Model for Plant-Pathogen Interactions," *Mol. Plant Microbe Interact.* 21:1015-26 (2008), which is hereby incorporated by reference in its entirety).

DC3000D28E growth in *N. benthamiana* is symptomless and 4 logs lower than DC3000ΔhopQ1-1. DC3000D28E appears to elicit plant defenses that are T3SS-dependent and additional to basal PTI. In this regard, it is noteworthy that DC3000D28E has the wild-type complement of T3SS helper proteins (except HrpW1), which fall into the overlapping functional classes of harpins, translocators, and lytic transglycosylases, and several of these proteins can elicit plant defenses (Kvitko et al., "Identification of harpins in *Pseudomonas syringae* pv. *Tomato* DC3000, Which Are Functionally Similar to HrpK1 in Promoting Translocation of Type III Secretion System Effectors," *J. Bacteriol.* 189: 8059-8072 (2007), which is hereby incorporated by reference in its entirety). T3Es in the minimal functional repertoire restore virulence to DC3000D28E in the following approximate hierarchy. AvrPtoB partially suppresses T3SS- and PAMP-triggered immunity. Other T3Es then promote further growth (HopM1 and HopE1), chlorosis (HopG1), lesion formation (HopAM1-1), and then near-full growth and symptom production (AvrE, HopAA1-1, and/or HopN1 functioning synergistically with the previous effectors). Introducing more T3E genes would incrementally increase virulence and restore redundancy, with limits to repertoire size in field populations being imposed by interactions with co-evolving host ETI systems.

The limited knowledge of specific T3E functions is consistent with the hierarchy observed in the minimal repertoire. AvrPtoB inhibits PRR co-receptor complexes involved in initial perception of pathogens (Shan et al. "Bacterial Effectors Target the Common Signaling Partner BAK1 to Disrupt Multiple MAMP Receptor-Signaling Complexes and Impede Plant Immunity," *Cell Host Microbe* 4:17-27 (2008), which is hereby incorporated by reference in its entirety). HopM1 destabilizes a plant ADP ribosylation factor (ARF) guanine nucleotide exchange factor (GEF) protein involved in vesicle trafficking and likely important for plant deployment of defense factors (Nomura et al., "A Bacterial Virulence Protein Suppresses Host Innate Immunity to Cause Plant Disease," *Science* 313:220-223 (2006), which is hereby incorporated by reference in its entirety). HopG1 is localized to plant mitochondria and elevates levels of reactive oxygen species (Block et al., "The *Pseudomonas syringae* Type III Effector HopG1 Targets Mitochondria, Alters Plant Development, and Suppresses Plant Innate Immunity," *Cell Microbiol.* 12:318-330 (2009), which is hereby incorporated by reference in its entirety). HopAM1 is thought to manipulate defense-related responses to the hormone abscisic acid and also causes cell death when expressed in yeast cells (Goel et al., "The *Pseudomonas syringae* Type III Effector HopAM1 Enhances Virulence on Water-Stressed Plants," *Mol. Plant Microbe Interact.* 21:361-70 (2008) and Munkvold et al., "A Survey of the *Pseudomonas syringae* pv. *tomato* DC3000 Type III Secretion System Effector Repertoire Reveals Several Effectors That Are Deleterious When Expressed in *Saccharomyces cerevisiae*," *Mol. Plant-Microbe Interact.* 21:490-502 (2008), which are hereby incorporated by reference in their entirety). AvrE may mimic activated G-proteins and thereby functionally overlap with HopM1 in disrupting vesicle trafficking (Ham et al., "Multiple Activities of the Plant Pathogen Type III Effector Proteins WtsE and AvrE Require WxxxE Motifs," *Mol. Plant Microbe Interact.* 22:703-12 (2009), which is hereby incorporated by reference in its entirety). HopAA1-1 elicits cell death when expressed in yeast and plant cells (Munkvold et al., "A Survey of the *Pseudomonas syringae* pv. *tomato* DC3000 Type III Secretion System Effector Repertoire Reveals Several Effectors That Are Deleterious When Expressed in *Saccharomyces cerevisiae*," *Mol. Plant-Microbe Interact.* 21:490-502 (2008), which is hereby incorporated by reference in its entirety). HopN1 is a cysteine protease that can suppress ETI-associated cell death (López-Solanilla et al., "HopPtoN is a *Pseudomonas syringae* Hrp (Type III Secretion System) Cysteine Protease Effector That Suppresses Pathogen-Induced Necrosis Associated With Both Compatible and Incompatible Plant Interactions," *Mol. Microbiol.* 54:353-365 (2004), which is hereby incorporated by reference in its entirety). How these few T3Es function together to form a minimal repertoire may be complex because T3Es can have multiple domains and interfering activities. For example, AvrPtoB also possesses an E3 ubiquitin ligase domain that can suppress ETI (Rosebrock et al., "A Bacterial E3 Ubiquitin Ligase Targets a Host Protein Kinase to Disrupt Plant Immunity." *Nature* 448:370-374 (2007), which is hereby incorporated by reference in its entirety), and HopM1, AvrE, and HopAA1-1 elicit ETI-like cell death in *N. benthamiana* when individually delivered by the nonpathogen *Pseudomonas fluorescens* expressing cloned *P. syringae* T3SS genes (Wei et al., "A *Pseudomonas syringae* pv. *tomato* DC3000 Mutant Lacking the Type III Effector HopQ1-1 Is Able to Cause Disease in the Model Plant *Nicotiana* benthamiana," Plant J. 51:32-46 (2007), which is hereby incorporated by reference in its entirety). An advantage of the DC3000D28E PRIVAS system is that it provides strong phenotypes and facile tools for dissection of T3Es and their interplay in near-native settings.

As explained above, it is possible that a minimal functional repertoire could have been assembled with T3Es other than HopE1, HopG1, and HopAM1. Indeed, the sequenced strains *P. syringae* pv. *syringae* B728a and *P. syringae* pv. *tabaci* 11528 also cause disease in *N. benthamiana*, but their genomes lack hopE1, hopG1, hopAM1, hopAA1-1, and hopN1 (Vinatzer et al., "The Type III Effector Repertoire of *Pseudomonas syringae* pv. *syringae* B728a and Its Role in Survival and Disease on Host and Non-Host Plants," *Mol. Microbiol.* 62:26-44 (2006) and Studholme et al., "A Draft Genome Sequence and Functional Screen Reveals the Repertoire of Type III Secreted Proteins of *Pseudomonas syringae* pathovar *tabaci* 11528,*" BMC Genomics* 10:395 (2009), which are hereby incorporated by reference in their entirety). Clearly, *P. syringae* can defeat plants with alternative T3E repertoires. But the bacteria do not appear able to do so with just one or two T3Es. This presumably is a result of redundancy and consequent robustness in plant PTI/ETI perception and signaling networks, as revealed by recent reports that mutations in multiple signaling components are needed to significantly compromise plant immunity and that exhaustive genetic screens revealed no essential PTI component signaling downstream of PRRs (Tsuda et al., "Network Properties of Robust Immunity in Plants," *PLoS Genet.* 5:e1000772 (2009); Boudsocq et al. "Differential Innate Immune Signalling Via Ca(2+) Sensor Protein Kinases," *Nature* 464:418-U116 (2010); Chakravarthy et al., "Identification of *Nicotiana benthamiana* Genes Involved in PAMP-Triggered Immunity," *Mol. Plant-Microbe Interact.* 23:715-726 (2010); Li et al., "Specific ER Quality Control Components Required for Biogenesis of the Plant Innate Immune Receptor EFR," *Proc. Natl. Acad. Sci. USA* 106: 15973-8 (2009); and Saijo et al., Receptor Quality Control in the Endoplasmic Reticulum for Plant Innate Immunity," *EMBO J* 28(21):3439-49 (2009), which are hereby incorporated by reference in their entirety). In this regard, it is noteworthy that the PRIVAS system, modified for use with *Agrobacterium tumefaciens*-based vectors could be used for random and programmed combinatorial expression and silencing of plant immunity genes. More broadly, the use of flexible, dual adapters for recombination, as exemplified with the PRIVAS system, represents an addition to the growing suite of multigene recombineering tools (Bieniossek et al., "Automated Unrestricted Multigene Recombineering for Multiprotein Complex Production," *Nat. Methods* 6:447-50 (2009), which is hereby incorporated by reference in its entirety that is particularly suited for deconvoluting internal redundancy and exploring functional structure in complex biological systems.

In the case of plant-pathogen interactions, using pathogens with PRIVAS-derived minimal repertoires to defeat plant immunity provides a means to efficiently probe defenses at the systems level and complements studies based on plant genetics. By understanding how the PTI system fails, better plants, having enhanced PTI system robustness, can be bred. Similarly, by understanding how pathogens evolve rapidly adaptable T3E systems, combinations of R genes that confer more durable ETI in the field can be deployed. In summary, DC3000D28E, the PRIVAS system, and minimal functional repertoires provide resources for accelerated study of T3Es and plant immune systems.

Although the invention has been described in detail for the purpose of illustration, it is understood that such detail is solely for that purpose, and variations can be made therein by those skilled in the art without departing froth the spirit and scope of the invention which is defined in the following claims.

What is claimed:

1. A method of assembling synthetic genetic constructs, said method comprising:
providing a plurality of separate genetic units each having opposing ends;
appending first universal adapter oligonucleotides and second universal adapter oligonucleotides to opposing ends of each separate genetic unit to form a plurality of separate extended genetic units each having the first universal adapter oligonucleotide and the second universal adapter oligonucleotide at opposing ends, thereby producing a plurality of universalized genetic units;
attaching flexible adapter oligonucleotides, which have nucleotide sequences that are different from those of said first and second universal adapter oligonucleotides, to the first and second universal adapter oligonucleotides at opposing ends of each of the plurality of universalized genetic units to form a plurality of separate dual extended genetic units each having flexible adapter oligonucleotides at opposing ends, wherein the universal adapter oligonucleotides and the flexible adapter oligonucleotides produce dual extensions at each of the opposing ends that are different from each other and wherein the separate dual extended genetic units each have the same or different combinations of flexible adapter oligonucleotides at opposing ends;
combining a plurality of the separate dual extended genetic units to form a mixture of the plurality of separate dual extended genetic units, wherein the combination of flexible adapter oligonucleotides in the different dual extended genetic units within the mixture are the same or different; and
subjecting the mixture of the plurality of the separate dual extended genetic units to homologous recombination between the flexible adapter oligonucleotides of each of the separate dual extended genetic units in the mixture to form linear synthetic genetic constructs comprising combinations of the plurality of the separate genetic units positioned end-to-end within the linear synthetic genetic construct.

2. The method of claim 1, wherein said appending first universal adapter oligonucleotides and second universal adapter oligonucleotides to the opposing ends of each separate genetic unit involves using one or more enzymes selected from the group consisting of exonucleases, ligases, polymerases, and restriction enzymes.

3. The method of claim 2, wherein said appending first universal adapter oligonucleotides and second universal adapter oligonucleotides to opposing ends of each separate genetic unit to form a plurality of separate extended genetic units involves using a polymerase, said method further comprising:
providing one or more sets of universal adapter oligonucleotide primers, each set comprising (1) a first oligonucleotide primer comprising a genetic unit specific portion and a first universal adapter specific portion and (2) a second oligonucleotide primer comprising a genetic unit specific portion and a second universal adapter specific portion, wherein the first and second universal adapter specific portions of the primers in a primer set comprise different nucleotide sequences;
providing a polymerase;
blending the one or more sets of universal adapter oligonucleotide primers and the polymerase with the plurality of separate genetic units to form a polymerase chain reaction mixture; and
subjecting the polymerase chain reaction mixture to one or more polymerase chain reaction cycles to append the first and second universal adapter oligonucleotides to opposing ends of each separate genetic unit to form a plurality of universalized genetic units each having the first universal adapter oligonucleotides and second universal adapter oligonucleotides at opposing ends.

4. The method of claim 1, wherein said attaching involves using an enzyme selected from the group consisting of exonucleases, polymerases, ligases, and restriction enzymes.

5. The method of claim 4, wherein said attaching comprises using a polymerase, said method further comprising:
providing a plurality of flexible adapter oligonucleotide primer sets, each set comprising (1) a first oligonucleotide primer comprising a first universal adapter specific portion and a flexible adapter specific portion and (2) a second oligonucleotide primer comprising a second universal adapter specific portion and a flexible adapter specific portion;
providing a polymerase;
blending the plurality of flexible adapter oligonucleotide primer sets and the polymerase with the plurality of separate extended genetic units to form a polymerase chain reaction mixture; and subjecting the polymerase chain reaction mixture to two or more polymerase chain reaction cycles to attach the flexible adapter oligonucleotides to opposing ends of each of the plurality of universalized genetic units to form a plurality of separate dual extended genetic units each having flexible adapter oligonucleotides at opposing ends.

6. The method of claim 1, further comprising:
providing a linearized nucleic acid vector comprising flexible adapter oligonucleotides at its opposing ends;
combining the linear synthetic genetic constructs and the linearized nucleic acid vector to form a mixture; and
subjecting the mixture to homologous recombination, where the terminal flexible adapter oligonucleotides of the linearized nucleic acid vector and the linear synthetic genetic constructs are the same, to form a re-circularized vector containing the previously linear synthetic genetic construct.

7. The method of claim 6 further comprising:
isolating the re-circularized nucleic acid vector containing the synthetic genetic construct.

8. The method of claim 6, wherein the nucleic acid vector is selected from the group consisting of a plasmid vector, a shuttle vector, a viral vector, an expression vector, and a cloning vector.

9. The method of claim 1, wherein said subjecting the mixture of the plurality of the separate dual extended genetic units to homologous recombination is carried out by in vitro homologous recombination, said method further comprising:
providing one or more recombinant proteins or cell extracts having the property of promoting homologous recombination and
blending the one or more recombinant proteins or cell extracts with the mixture of the plurality of the separate dual extended genetic units under conditions suitable for homologous recombination and assembly of the plurality of the separate dual extended genetic units to form the linear synthetic genetic construct.

10. The method of claim 1, wherein said subjecting the mixture of the plurality of the separate dual extended genetic units to homologous recombination is carried out by in vivo homologous recombination, said method further comprising:
transforming a competent host cell with the plurality of the separate dual extended genetic units under conditions suitable for in vivo homologous recombination to occur between flexible adapter oligonucleotide portions of the plurality of the separate dual extended genetic units, which are the same, thereby assembling the separate genetic units into the linear synthetic genetic construct.

11. The method of claim 10 further comprising:
isolating the linear synthetic genetic construct from the competent host cell.

12. The method of claim 10, wherein the competent host cell is selected from the group consisting of an animal cell, plant cell, archaebacterial cell, eubacterial cell, fungal cell, protist cell, and synthetic cell.

13. The method of claim 10 further comprising:
transforming the competent host cell with a linearized nucleic acid vector comprising flexible adapter oligonucleotides at its opposing ends, wherein the homologous recombination occurs between flexible adapter oligonucleotides of the plurality of the separate dual extended genetic units and the terminal flexible adapter oligonucleotides of the linearized vector, which are the same, to form a re-circularized nucleic acid vector comprising the previously linear synthetic genetic construct.

14. The method of claim 13, wherein the linearized vector is selected from the group consisting of plasmid vectors, shuttle vectors, cloning vectors, and expression vectors.

15. The method of claim 1, wherein each of the plurality of the separate dual extended genetic units are randomly assembled through the use of multiple, alternative genetic units to which the same flexible adapters have been appended.

16. The method of claim 1, wherein each of the plurality of the separate dual extended genetic units are semi-randomly assembled through the use of multiple, alternative genetic units to which the same flexible adapters have been appended for some, but not all, positions in the genetic units.

17. The method of claim 1, wherein each of the plurality of the separate dual extended genetic units are non-randomly assembled.

18. The method of claim 1, wherein the plurality of separate genetic units comprise artificial nucleotide sequences.

19. The method of claim 1, wherein the plurality of separate genetic units comprise nucleotide sequences derived from a genomic sequence of an animal, plant, archaebacteria, eubacteria, fungus, protist, virus, and combinations thereof.

20. The method of claim 1, wherein each of the plurality of the separate genetic units comprises one or more functional domains and/or modules of a single gene.

21. The method of claim 1, wherein each of the plurality of the separate genetic units comprises one or more functional genes.

22. The method of claim 1, wherein the linear synthetic genetic construct encodes one or more partial or complete biological pathway.

23. The method of claim 1, wherein the linear synthetic genetic construct encodes a partial or complete genome.

24. The method of claim 1 further comprising:
isolating the plurality of linear synthetic genetic constructs;
transforming a plurality of the host cells with one of the plurality of the isolated linear synthetic genetic constructs under conditions suitable to express the linear synthetic genetic construct; and
testing the plurality of linear synthetic genetic constructs for their effect on the host cells.

25. The method of claim 24, wherein the host cell is selected from the group consisting of an animal cell, plant cell, archaebacterial cell, eubacterial cell, fungal cell, protist cell, and synthetic cell.

26. The method of claim 24, wherein the linear synthetic genetic construct provides a loss of function to the host cell.

27. The method of claim 24, wherein the linear genetic construct provides a gain of function to the host cell.

28. The method of claim 1, wherein said subjecting the mixture of the plurality of the separate dual extended genetic units to homologous recombination is carried out by in vitro homologous recombination, said method further comprising:
providing one or more recombinant proteins or cell extracts having the property of promoting homologous recombination when the flexible adapter oligonucleotides at the termini of the linearized nucleic acid vector and the assembled synthetic genetic constructs are the same, to form a re-circularized vector containing the assembled construct of dual extended genetic units.

* * * * *

UNITED STATES PATENT AND TRADEMARK OFFICE
CERTIFICATE OF CORRECTION

PATENT NO. : 9,689,012 B2
APPLICATION NO. : 13/879290
DATED : June 27, 2017
INVENTOR(S) : Cunnac and Collmer It is certified that error appears in the above-identified patent and that said Letters Patent is hereby corrected as shown below:

In the Specification

Column 1 at Lines 13-15, delete "This application claims the benefit of U.S. Provisional Patent Application Ser. No. 61/392,209, filed Oct. 12, 2010, which is hereby incorporated by reference in its entirety." and insert --This invention was made with government support under grant number 0605059 awarded by the National Science Foundation. The government has certain rights in the invention.--

Signed and Sealed this
Third Day of October, 2017

Joseph Matal
*Performing the Functions and Duties of the*
*Under Secretary of Commerce for Intellectual Property and*
*Director of the United States Patent and Trademark Office*